US010570380B2

(12) United States Patent
Jonk et al.

(10) Patent No.: US 10,570,380 B2
(45) Date of Patent: *Feb. 25, 2020

(54) DOWNSTREAM PROCESSING OF AN ALKALINE PHOSPHATASE

(71) Applicant: AM-Pharma B.V., Bunnik (NL)

(72) Inventors: Luigi Johannes Cornelius Jonk, Utrecht (NL); Stephen Edward Connor, Cambridge (GB); Erik Jan Van Den Berg, Vught (NL); Andrea Van Elsas, Oss (NL); Abhinav Alok Shukla, Morrisville, NC (US); Heather Bethea Horne, Raleigh, NC (US); Susan Cook, Flemington, NJ (US); Timothy Martin Kelly, Raleigh, NC (US); Victoria Anne Dowling, Boulder, CO (US); Mialy Fanjamalala Ramaroson, Cary, NC (US)

(73) Assignee: AM-PHARMA B.V., Bunnik (NL)

(*) Notice: Subject to any disclaimer, the term of this patent is extended or adjusted under 35 U.S.C. 154(b) by 88 days.

This patent is subject to a terminal disclaimer.

(21) Appl. No.: 15/113,699

(22) PCT Filed: Jan. 26, 2015

(86) PCT No.: PCT/NL2015/050046
§ 371 (c)(1),
(2) Date: Jul. 22, 2016

(87) PCT Pub. No.: WO2015/112015
PCT Pub. Date: Jul. 30, 2015

(65) Prior Publication Data
US 2017/0009217 A1    Jan. 12, 2017

(30) Foreign Application Priority Data
Jan. 24, 2014 (EP) .................................. 14152542

(51) Int. Cl.
*C12N 9/16* (2006.01)
*A61K 47/10* (2017.01)
*A61K 38/46* (2006.01)
*A61K 47/12* (2006.01)
*A61K 47/22* (2006.01)
*A61K 47/26* (2006.01)
A61K 38/00 (2006.01)

(52) U.S. Cl.
CPC .............. *C12N 9/16* (2013.01); *A61K 38/465* (2013.01); *A61K 47/10* (2013.01); *A61K 47/12* (2013.01); *A61K 47/22* (2013.01); *A61K 47/26* (2013.01); *C12Y 301/03001* (2013.01); A61K 38/00 (2013.01)

(58) Field of Classification Search
CPC ...... A61K 38/465; A61K 38/00; A61K 47/10; A61K 47/12; A61K 47/22; A61K 47/26; C12N 9/16; C12Y 301/03001
See application file for complete search history.

(56) References Cited

U.S. PATENT DOCUMENTS

| | | | |
|---|---|---|---|
| 5,567,724 A | 10/1996 | Kelleher et al. | |
| 5,723,441 A | 3/1998 | Higley et al. | |
| 6,290,952 B1 | 9/2001 | Poelstra et al. | |
| 6,406,899 B1 | 6/2002 | Hoelke et al. | |
| 7,157,260 B2 | 1/2007 | Mori et al. | |
| 7,786,082 B2 | 8/2010 | Kiss | |
| 7,856,139 B2 | 12/2010 | Chen | |
| 7,973,015 B2 | 7/2011 | Van et al. | |
| 8,557,545 B2 | 10/2013 | Velders et al. | |
| 8,574,863 B2 | 11/2013 | Brands et al. | |
| 8,586,032 B2 | 11/2013 | Pickkers et al. | |
| 8,735,087 B2 | 5/2014 | Brands et al. | |
| 9,453,045 B2 | 9/2016 | Gilljam et al. | |
| 2002/0055098 A1 | 5/2002 | Szasz et al. | |
| 2003/0235845 A1 | 12/2003 | Van et al. | |
| 2004/0115185 A1 | 6/2004 | Kiss | |
| 2004/0146907 A1 | 7/2004 | Smith | |
| 2006/0099616 A1 | 5/2006 | Van et al. | |
| 2006/0147952 A1 | 7/2006 | Van et al. | |
| 2007/0059300 A1 | 3/2007 | Kiss | |
| 2008/0044397 A1 | 2/2008 | Kiss et al. | |
| 2008/0209581 A1 | 8/2008 | Van et al. | |
| 2009/0010912 A1 | 1/2009 | Brands et al. | |

(Continued)

FOREIGN PATENT DOCUMENTS

| | | |
|---|---|---|
| CN | 1425766 A | 6/2003 |
| CN | 102858797 A | 1/2013 |

(Continued)

OTHER PUBLICATIONS

Zappa S. et al., "Characterization of a Highly Thermostable Alkaline Phosphatase from the Euryarchaeon Pyrococcus abyssi", Applied and Environmental Microbiology, Oct. 2001, vol. 67, No. 10, pp. 4504-4511. (Year: 2001).*

Berger, J., et al., "Cloning and Sequencing of Human Intestinal Alkaline Phosphatase cDNA," Proceedings of the National Academy of Sciences USA 84:695-698, National Academy of Sciences, United States (1987).

Bernstine, E.G., et al., "Alakaline Phosphatase Activity in Mouse Teratoma," Proceedings of the National Academy of Sciences USA 70(12):3899-3903, National Academy of Sciences, United States (1973).

Beumer, C., et al., "Calf Intestinal Alkaline Phosphatase, a Novel Therapeutic Drug for Lipopolysaccharide (LPS)-mediated Diseases, Attenuates LPS Toxicity in Mice and Piglets," Journal of Pharmacology and Experimental Therapeutics 307(2):737-744, American Society for Pharmacology and Experimental Therapeutics, United States (2003).

(Continued)

*Primary Examiner* — Satyendra K Singh
(74) *Attorney, Agent, or Firm* — Sterne, Kessler, Goldstein & Fox P.L.L.C.

(57) ABSTRACT

The invention relates to the field of downstream processing (DSP) of an alkaline phosphatase (AP). More specifically, it relates to a method for reducing host cell protein content in a composition comprising AP. The invention further relates to a composition comprising an AP and a reduced content of a host cell protein.

19 Claims, 27 Drawing Sheets

Figure 1:
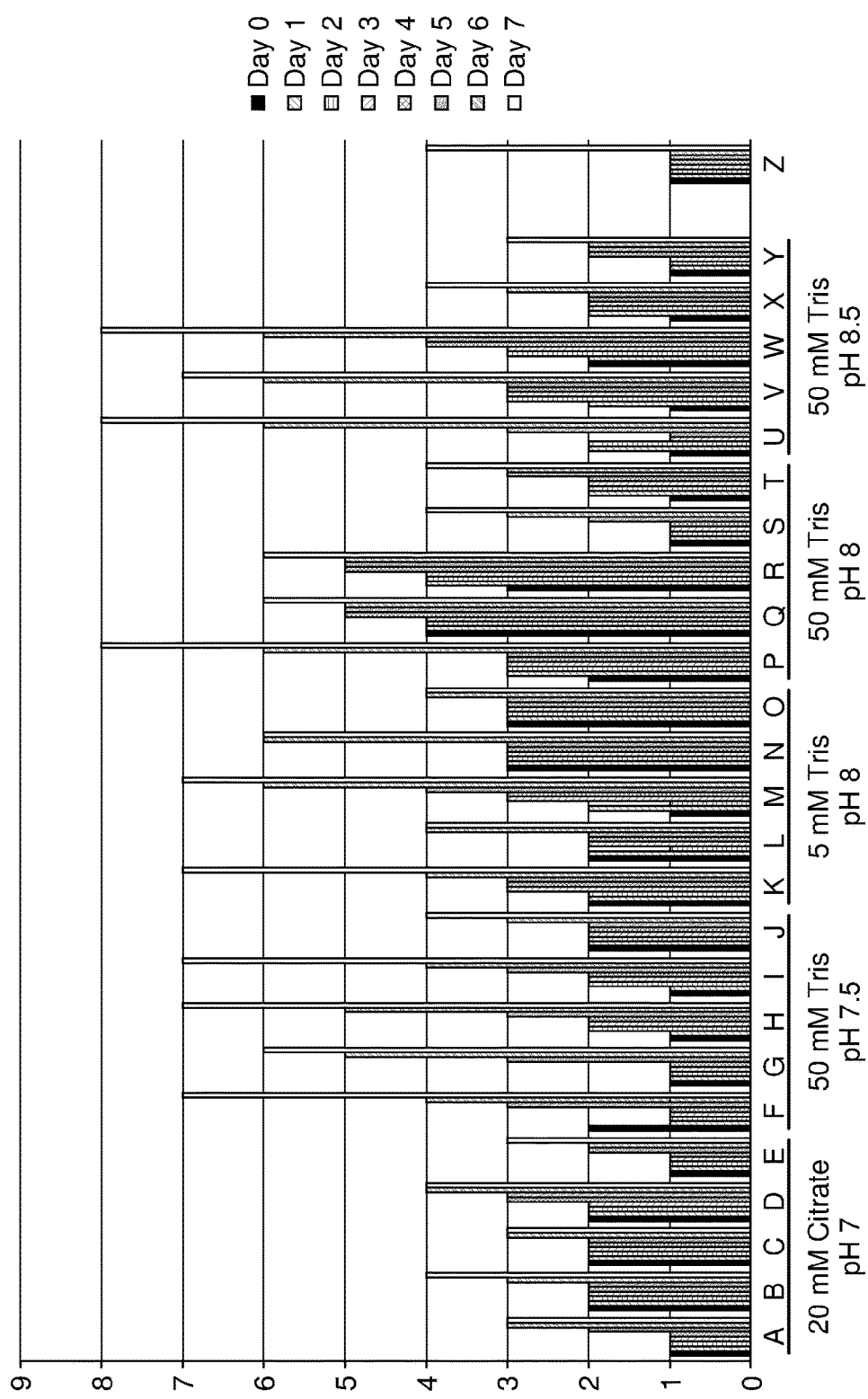

Specification includes a Sequence Listing.

(56) References Cited

U.S. PATENT DOCUMENTS

| | | |
|---|---|---|
| 2009/0069244 A1 | 3/2009 | Brouwer et al. |
| 2009/0228998 A1 | 9/2009 | Van et al. |
| 2010/0016313 A1 | 1/2010 | Millan et al. |
| 2010/0111923 A1 | 5/2010 | Pickkers et al. |
| 2010/0143323 A1 | 6/2010 | Velders et al. |
| 2010/0158888 A1 | 6/2010 | Kiss |
| 2011/0052560 A1 | 3/2011 | Brands |
| 2011/0142817 A1 | 6/2011 | Brands et al. |
| 2011/0206654 A1 | 8/2011 | Hodin et al. |
| 2013/0096279 A1 | 4/2013 | Gilljam et al. |
| 2013/0280232 A1 | 10/2013 | Brands et al. |
| 2014/0193388 A1 | 7/2014 | Velders et al. |
| 2014/0219984 A1 | 8/2014 | Arend et al. |
| 2016/0046913 A1 | 2/2016 | Velders et al. |
| 2016/0250299 A1 | 9/2016 | Arend et al. |
| 2019/0209662 A1 | 7/2019 | Arend et al. |

FOREIGN PATENT DOCUMENTS

| | | | |
|---|---|---|---|
| EP | 0151320 A2 * | 8/1985 | ............... C12Q 1/42 |
| EP | 0 791 658 A1 | 8/1997 | |
| EP | 1132086 A2 | 9/2001 | |
| EP | 1733734 A2 | 12/2006 | |
| EP | 1952823 A1 | 8/2008 | |
| EP | 1985697 A1 | 10/2008 | |
| JP | H04349881 A | 12/1992 | |
| JP | H0998780 A | 4/1997 | |
| JP | H09172962 A | 7/1997 | |
| JP | 2000350596 A | 12/2000 | |
| JP | 2003146888 A | 5/2003 | |
| JP | 2005065564 A | 3/2005 | |
| WO | WO-9318139 A1 | 9/1993 | |
| WO | WO-9505455 A1 | 2/1995 | |
| WO | WO-9505456 A1 | 2/1995 | |
| WO | WO-9639203 A1 | 12/1996 | |
| WO | WO-0037943 A1 | 6/2000 | |
| WO | WO-0206214 A1 | 1/2002 | |
| WO | WO-02056900 A2 | 7/2002 | |
| WO | WO-02057430 A2 | 7/2002 | |
| WO | WO-02098433 A1 | 12/2002 | |
| WO | WO-03015817 A2 | 2/2003 | |
| WO | WO-2004056987 A1 | 7/2004 | |
| WO | WO-2005074978 A1 | 8/2005 | |
| WO | WO-2006096527 A2 | 9/2006 | |
| WO | WO-2008094037 A1 | 8/2008 | |
| WO | WO-2008104199 A1 | 9/2008 | |
| WO | WO-2008133511 A2 | 11/2008 | |
| WO | WO 2009/106368 A1 | 9/2009 | |
| WO | WO-2010025267 A2 | 3/2010 | |
| WO | WO-2011121031 A1 | 10/2011 | |
| WO | WO-2012169892 A2 | 12/2012 | |

OTHER PUBLICATIONS

Bossi, M., et al., "Modifications in a Flexible Surface Loop Modulate the Isozyme-specific Properties of Mammalian Alkaline Phosphatases," Journal of Biological Chemistry 34:25409-25416, American Society for Biochemistry and Molecular Biology, United States (1993).

Boulain, J., et al., Patent Abstracts of Japan, English language Abstract of Japanese Patent Publication No. 09-098780, "Modified Baterium Alkaline Phosphatase and Its Use," Japanese Patent Office, Patent & Utility Model Gazette DB (1997).

Brennan, C.A., et al., "A Molecular Sensor System Based on Genetically Engineered Alkaline Phosphatase," Proceedings of the National Academy of Sciences of the United States of America 92: 5783-5787, National Academy of Sciences, United States (1995).

Engle, M.J., et al., "Two Rat Intestinal Alkaline Phosphatase Isoforms with Different Carboxyl-terminal Peptides are Both Membrane-bound by a Glycan Phosphatidylinositol Linkage," Journal of Biological Chemistry 20:11935-11940, American Society for Biochemistry and Molecular Biology, United States (1995).

English language Abstract and machine translation of Japanese Patent Publication No. 09-172962 A, Japanese Patent Office, Jul. 8, 1997.

English Language Abstract for CN1425766, Published Jun. 25, 2003. .

Eriksson H.J., et al., "Investigations into the Stabilization of Drugs by Sugar Glasses: Delivery of an Insulin-stabilised Alkaline Phosphatase in the Intestinal Lumen Via the Oral Route" International Journal of Pharmaceutics 257:273-281, Elsevier/North-Holland Biomedical Press, Netherlands (2003).

Gayle, R.B., III., et al., "Identification of Regions in Interleukin-1α Important for Activity," The Journal of Biological Chemistry 268(29):22105-22111, The American Society for Biochemistry and Molecular Biology, Inc., United States (1993).

Harms, G., et al., "Immunopathology of Alkaline Phosphatase-induced Granulomatous Hepatitis in Rats," Virchows Archiv. B, Cell Pathology Including Molecular Pathology 62(1):35-43, Springer-Verlag, Germany (1992).

Henthorn, P., et al., "Nucleotide and Amino Acid Sequences of Human Intestinal Alkaline Phosphatase: Close Homology to Placental Alkaline Phosphatase," Proceedings of the National Academy of Sciences USA 84(12):4088, National Academy of Sciences, United States (1987).

Henthorn, P., et al., "Nucleotide and Amino Acid Sequences of Human Intestinal Alkaline Phosphatase: Close Homology to Placental Alkaline Phosphatase," Proceedings of the National Academy of Sciences USA 84:1234-1238, National Academy of Sciences, United States (1987).

Henthorn, P.S., et al., "Sequence and Characterization of the Human Intestinal Alkaline Phosphatase Gene," The Journal of Biological Chemistry 263:12011-12019, American Society for Biochemistry and Molecular Biology, United States (1988).

International Search Report for International Application No. PCT/NL2008/050249, European Patent Office, Netherlands, dated Jan. 15, 2009, 6 pages.

International Search Report for International Application No. PCT/NL2012/050400, European Patent Office, Netherlands, dated Jan. 15, 2013, 5 pages.

International Search Report for International Application No. PCT/NL2015/050046, European Patent Office, Netherlands, dated Jun. 29, 2015, 7 pages.

Jacob, S., et al., "Pharmacotherapy of Atrial Fibrillation: A Pathophysiological Perspective and Review," American Journal of Therapeutics 18(3):241-260, Lippincott Williams & Wilkins, United States (2011).

Kodama, H., et al., "Expression of a Heterodimeric (placental-intestinal) Hybrid Alkaline Phosphatase in KB Cells" Biochimica et Biophysica Acta 1218:163-172, Elsevier Pub. Co., Netherlands (1994).

Koyama, I., et al., "Alkaline Phosphatases Reduce Toxicity of Lipopolysaccharides in Vivo and in Vitro through Dephosphorylation," Clinical Biochemistry 35(6):455-461, Elsevier Science, United States (2002).

Labrou, N.E., "Dye-ligand Affinity Adsorbents for Enzyme Purification," Molecular Biotechnology 20(1):77-84, Humana Press, United States (2002).

Le Du, M.H, and Millian, J.L., "Structural Evidence of Functional Divergence in Human Alkaline Phosphatases." Journal of Biological Chemistry 277(51):49808-49814, American Society for Biochemistry and Molecular Biology, United States (2002).

Leibovitch, I., et al., "Increased Serum Alkaline Phosphatase Activity: A Possible Indicator of Renal Damage," Journal of Clinical Laboratory Analysis 5(6):406-409, Wiley-Liss, Inc., United States (1991).

Lindner, N.M., et al., "Design and Applications of Biomimetic Anthraquinone Dyes. Purification of Calf Intestinal Alkaline Phosphatase With Immobilised Terminal Ring Analogues of C.I. Reactive Blue 2," Journal of Chromatography 473(1):227-240, Elsevier, Netherlands (1989).

Mandecki, W., et al., Patent Abstracts of Japan, English language Abstract of Japanese Patent Publication No. 04-349881, "Synthe-

(56) References Cited

OTHER PUBLICATIONS sized Alkaline Phosphatase Enzyme Having Improved Specific Activity," Japanese Patent Office, Patent & Utility Model Gazette DB (1992).
Mayo Clinic Staff, "Diseases and Conditions Acute kidney failure," accessed at http://www.mayoclinic.org/diseases-conditions/kidney-failure/basics/prevention/con-20024029?p=1 accessed on Jul. 24, 2015, 7 pages (2015).
Millan, Jose Luis, "Alkaline Phosphatases: Structure, Substrate Specificity and Functional Relatedness to Other Members of a Large Superfamily of Enzymes," Purinergic Signaling 2:335-341, Springer, Netherlands (2006).
Mornet, E., et al., "Structural Evidence for a Functional Role of Human Tissue Nonspecific Alkaline Phosphatase in Bone Mineralization," Journal of biological chemistry 26:31171-31178, American Society for Biochemistry and Molecular Biology, United States (2001).
Naber, T.H., et al., "Serum Alkaline Phosphatase Activity During Zinc Deficiency and Long-term Inflammatory Stress," Clinica Chimica Acta 249:109-127, Elsevier, Netherlands (1996).
NCBI Acct#NP_001622.2 versus Bossi et al., USPTO in house alignment Feb. 22, 2012.
Nugent, S.G., et al., "Review: Intestinal Luminal pH in Inflammatory Bowel Disease: Possible Determinants and Implications for Therapy with Aminosalicylates and Other Drugs," Gut 48:571-577, British Medical Association, England (2001).
Okamoto, M., et al., Patent Abstracts of Japan, English language Abstract of Japanese Patent Publication No. 2000-350596, "Selective Assay of Secreted Alkaline Phosphatase Activity," Japanese Patent Office, Patent & Utility Model Gazette DB (2000).
Poelstra, K., et al., "Dephosphorylation of Endotoxin by Alkaline Phosphatase in Vivo," American Journal of Pathology 151(4):1163-1169, Elsevier, United States (1997).
Riordan, W.T., et al., "Salt Tolerant Membrane Adsorbers for Robust Impurity Clearance," Biotechnology Progress 25(6):1695-1702, Wiley-Blackwell, United States (2009).
Sanchez De Medina F., et al., "Induction of Alkaline Phosphatase in the Inflamed Intestine: A Novel Pharmacological Target for Inflammatory Bowel Disease," Biochemical Pharmacology, 68:2317-2326, Elsevier Science, England (2004).
Shahani, K.M., et al., "Enzymes in Bovine Milk: A Review," Journal of Dairy Science 56(5):531-543, American Dairy Science Association, United States (1973).
Shukla, A.A., et al., "Preparative Purification of a Recombinant Protein by Hydrophobic Interaction Chromatography: Modulation of Selectivity by the Use of Chaotropic Additives," Biotechnology Progress 18(3):556-564, Wiley-Blackwell, United States (2002).
Shulka, et al., "Host Cell Protein Clearance During Protein a Chromatography: Development of an Improved Column Wash Step," Biotechnology Progress 24(5):1115-1121, American Institute of Chemical Engineers (2008).
Szuster-Ciesielska, et al., "The Inhibitory Effect of Zinc on Cadmium-induced Cell Apoptosis and Reactive Oxygen Species (ROS) Production in Cell Cultures," Toxicology 145(2-3):159-171, Elsevier, Ireland (2000).
The New York Times, "Chronic Kidney Disease Overview," accessed at http://nytimes.com/health/guides/disease/chronic-renal-failure/overview.html?print=1, accessed on Jul. 24, 2015, 3 pages (2015).
Tuin, et al., "Oral Administration of Alkaline Phosphatase Ameliorates Colitis." Gastroenterology 132:A231, Abstract #51611 (2007).
Udenfriend, S., et al., "Prediction of Omega Site in Nascent Precursor of Glycosylphophatidylinositol Protein," Methods Enzymology, 250:571-582, Academic Press, United States (1995).
Ueda, Hiroshi, Patent Abstract of Japan, English language Abstract of Japanese Patent Publication No. 2005-065564, "Sensor Protein," Japanese Patent Office, Patent & Utility Model Gazette DB (2005).
Unknown Author, "Chronic Kidney Disease—information Prescription," accessed at http://nhs.uk.Pages/Preview.aspx?site=Kidney-disease-chronic&print=63573354618, accessed on Jul. 24, 2015, 3 pages (2013).
Van Veen, S.Q., et al., "Alkaline Phosphatase Reduces Hepatic and Pulmonary Injury in Liver Ischaemia-reperfusion Combined with Partial Resection," The British Journal of Surgery 93: 448-456, Wiley, England (2006).
Van Veen, S.Q., et al., "Bovine Intestinal Phosphatase Attenuates the Inflammatory Response in Secondary Peritonitis in Mice," Infection and Immunity 73: 4309-4315, American Society for Microbiology, United States (2005).
Verweij, W.R., et. al., "Protection Against an *Escherichia coli*-induced Sepsis by Alkaline Phosphatase in Mice," Shock 22: 174-179, Lippincott Williams & Wilkins, United States (2004).
Wang, E., et al., "Crystal Structure of Alkaline Phosphatase from the Antarctic Bacterium TAB5," Journal of Molecular Biology 366:1318-1331, Elsevier Ltd., England (2007).
Wang, X., et al., "Host Cell Proteins in Biologics Development: Identification, Quantitation and Risk Assessment," Biotechnology and Bioengineering 103(3):446-458, Wiley, United States (2009).
Whisstock, et al., "Prediction of Protein Function From Protein Sequence and Structure," Quarterly Reviews of Biophysics 3:307-340 (2003).
Wray, L., and Harris H., "Demonstration Using Monoclonal Antibodies of Inter-Locus Heteromeric Isozymes of Human Alkaline Phosphatase" Journal of Immunological Methods 55:13-18, Elsevier, Netherlands (1982).
Wuhl, E., et al., "Antihypertensive and Antiproteinuric Efficacy of Ramipril in Children with Chronic Renal Failure," Kidney International 66:768-776, International Society of Nephrology, United States (2004).
Xu, et al., "Directed Evolution of *E. coli* Alkaline Phosphatase Towards Higher Catalytic Activity," Biocatalysis and Biotransformation 21: 41-47, United Kingdom (2003).
Zarbock, A., and Milles, K., "Novel Therapy for Renal Protection," Current Opinion in Anesthesiology 28(4):431-438, Lippincott Williams & Wilkins, United States (2015).

\* cited by examiner

| Label | ID | Test Wash Condition | Raw HCP (ppm) | Normalized HCP | recAP Yield (%) |
|---|---|---|---|---|---|
| | Assaymethod | | ELISA/ RPHPLC | | RP-Titer |
| | 1x15L CCH Load | N/A | 1,059,844 | N/A | N/A |
| 10 = ● | Run 10 (Baseline) | N/A | 554,979 | 1.00 | 87 |
| 2 = ● | Run 2 | 20 mM Tris, 0.1M NaCl, 0.2M L-Arg, pH 8.0 | 288,414 | 0.52 | 82 |
| 3 = ● | Run 3 | 20 mM sodium phosphate, 0.1M NaCl, pH 7.0 | 440,017 | 0.79 | 94 |
| 4 = ● | Run 4 | 20 mM Tris, 1M Urea, pH 8.0 | 376,044 | 0.68 | 97 |
| 5 = ● | Run 5 | 20 mM Tris, 1M Urea, 0.1M NaCl, pH 8.0 | 454,348 | 0.82 | 79 |
| 6 = ● | Run 6 | 20 mM sodium phosphate, 0.1M NaCl, 0.2M L-Arg, pH 7.0 | 570,808 | 1.03 | 63 |
| 7 = ○ | Run 7 | 20 mM Tris, 0.5M AmSO$_4$, pH 8.0 | 381,564 | 0.69 | 82 |
| 8 = ● | Run 8 | 20 mM Tris, 10% ethylene glycol, pH 8.0 | 462,249 | 0.83 | 107 |
| 9 = ● | Run 9 | 20 mM Tris, 10% ethylene glycol, 0.1M NaCl, pH 8.0 | 456,278 | 0.82 | 95 |
| 11 = ● | Run 11 | 20 mM Tris, 5% glycerol, 0.1M NaCl, pH 8.0 | 536,661 | 0.97 | 93 |

FIG. 5B

| Gel Lane | Test Wash ID | Sample Matrix | Raw HCP (ppm) | Normalized HCP | Eluate recAP Yield (%) |
|---|---|---|---|---|---|
| 1 | MWM | N/A | N/A | N/A | N/A |
| 2 | Capto Run 2 Eluate | 0.1M NaCl, 0.55M L-Arg, pH 8.0 | 288,414 | 0.52 | 82 |
| 3 | Capto Run 7 Intermediate Wash | 0.5M AmSO$_4$, pH 8.0 | N/A | N/A | N/A |
| 4 | Capto Run 7 Eluate | 0.1M NaCl, 0.55M L-Arg, pH 8.0 | 381,564 | 0.69 | 82 |
| 5 | Capto Run 10 Eluate (Baseline) | 0.1M NaCl, 0.55M L-Arg, pH 8.0 | 554,979 | 1.00 | 87 |

FIG. 6B

| ID | Test Wash Condition | Load Material | Raw HCP (ppm) ELISA/RPHPLC | Normalized HCP ELISA/RPHPLC | recAP Yield (%) RP-Titer |
|---|---|---|---|---|---|
| Assaymethod | | | | | |
| 1x15L CCH Load | N/A | N/A | 1,059,844 | N/A | N/A |
| 200L PD CCH Load | N/A | N/A | 952,724 | N/A | N/A |
| Baseline Control Runs | | | | | |
| Run 10 (Baseline) | N/A | 1x15L CCH Load | 554,979 | 1.00 | 87 |
| Run 23 (Baseline) | N/A | 200L PD CCH Load | 402,669 | 1.00 | 98 |
| Sequential Washes | | | | | |
| Run 12 | 1) 0.5M AmSO$_4$, pH 8.0  2) 0.1M NaCl, 0.2M L-Arg, pH 8.0 | 1x15L CCH Load | 291,665 | 0.53 | 76 |
| Run 18 | 1) 0.1M NaCl, 0.2M L-Arg, pH 8.0  2) 0.5M AmSO$_4$, pH 8.0 | 1x15L CCH Load | 220,244 | 0.40 | 99 |
| Run 22 | 1) 0.1M NaCl, 0.2M L-Arg, pH 8.0  2) 0.05M NaSCN, pH 8.0 | 200L PD CCH Load | 277,232 | 0.69 | 108 |
| Modulators in the Load | | | | | |
| Run 19 | Adjusted 0.05M NaCl, 0.1M L-Arg, pH 8.0 Load; 20mM Tris, 0.1M NaCl, 0.2M L-Arg, pH 8.0 Wash | 200L PD CCH Load | 293,413 | 0.73 | 105 |
| Combination Washes with Modulators | | | | | |
| Run 14 | 0.1M NaCl, 0.2M L-Arg, 0.5M AmSO$_4$, pH 8.0 | 1x15L CCH Load | 379,902 | 0.68 | 79 |
| Run 15 | 0.1M NaCl, 0.2M L-Arg, 1M urea, pH 8.0 | 1x15L CCH Load | 197,747 | 0.36 | 45 |
| Run 16 | 0.1M NaCl, 0.2M L-Arg, 10% ethylene glycol, pH 8.0 | 1x15L CCH Load | 255,905 | 0.46 | 74 |
| Run 17 | 0.1M NaCl, 0.2M L-Arg, 5% glycerol, pH 8.0 | 1x15L CCH Load | 193,135 | 0.35 | 104 |
| Run 20 | 0.1M NaCl, 0.25M Urea, 0.2M L-Arg, pH 8.0 | 200L PD CCH Load | 317,491 | 0.79 | 97 |
| Run 21 | 0.1M NaCl, 0.1M AmSO$_4$, 0.2M L-Arg, pH 8.0 | 200L PD CCH Load | 267,252 | 0.66 | 63 |
| Altered pH Washes | | | | | |
| Run 24 (Repeat) | 0.1M NaCl, 0.2M L-Arg, pH 8.0 | 200L PD CCH Load | 302,694 | 0.75 | 116 |
| Run 25 | 0.1M NaCl, 0.2M L-Arg, pH 8.5 | 200L PD CCH Load | 296,208 | 0.74 | 102 |
| Run 26 | 0.1M NaCl, 0.2M L-Arg, pH 9.0 | 200L PD CCH Load | 209,510 | 0.52 | 86 |

The HCP values for each eluate were normalized to the corresponding baseline eluate using the same load material.

FIG. 7B

| Gel Lane | Sample ID | Sample Matrix | Raw HCP (ppm) | Normalized HCP | Eluate recAP Yield (%) | Blot Load (µg) | Silver Load (µg) |
|---|---|---|---|---|---|---|---|
| 1 | MWM | N/A | N/A | N/A | N/A | N/A | N/A |
| 2 | 1x15L CCH Load | Media Components | 1,059,844 | N/A | N/A | 6.50 | 3.3 |
| 3 | Run 10 Baseline Eluate | 0.1M NaCl, 0.55M L-Arg, pH 8.0 | 554,979 | 1.00 | 87 | 10 | 5.0 |
| 4 | Run 2 Intermediate Wash | 0.1M NaCl, 0.2M L-Arg, pH 8.0 | N/A | N/A | N/A | 0.10 | 0.1 |
| 5 | Run 2 Eluate | 0.1M NaCl, 0.55M L-Arg, pH 8.0 | 288,414 | 0.54 | 82 | 10 | 5.0 |
| 6 | Run 17 Intermediate Wash | 0.1M NaCl, 0.2M L-Arg, 5% glycerol, pH 8.0 | N/A | N/A | N/A | 1.30 | 0.7 |
| 7 | Run 17 Eluate | 0.1M NaCl, 0.55M L-Arg, pH 8.0 | 193,135 | 0.35 | 104 | 10 | 5.0 |
| 8 | Buffer Blank | 1X LDS Sample Buffer | N/A | N/A | N/A | N/A | N/A |

FIG. 8C

| Label | ID | Test Wash Condition | HCP (ppm) | Normailized HCP | recAP Yield (%) |
|---|---|---|---|---|---|
| N/A | Poros Eluate | N/A | 95,591 | N/A | N/A |
| X= | Baseline | N/A | 2047 | 1.00 | 103 |
| 2= | Run 2 | 20mM Tris, 2mM MgCl₂, 50µM ZnCl₂, 200mM NaCl, pH 8.0 | 4767 | 2.32 | 10 |
| N/A | Run 3 | 20mM Tris, 2mM MgCl₂, 50µM ZnCl₂, 100 mM NaCl, pH 8.0 | Eluate not collected; approx 40% yield | | |
| 4= | Run 4 | 20mM Tris, 2mM MgCl₂, 50µM ZnCl₂, 1M Urea, pH 8.0 | 1066 | 0.52 | 90 |
| 5= | Run 5 | 20mM Tris, 2mM MgCl₂, 50µM ZnCl₂, 5% glycerol, pH 8.0 | 1981 | 0.97 | 100 |
| N/A | Run 6 | 20mM Tris, 2mM MgCl₂, 50µM ZnCl₂, 0.2M NaSCN, pH 8.0 | Product eluted in wash | | 0 |
| N/A | Run 7 | 20mM Tris, 2mM MgCl₂, 50µM ZnCl₂, 200mM Arginine, pH 8.0 | Product eluted in wash | | 0 |
| 8= | Run 8 | 20mM Tris, 2mM MgCl₂, 50µM ZnCl₂, 10% ethylene glycol, pH 8.0 | 1878 | 0.92 | 88 |

FIG. 9B

| Lane | Sample ID | Mass (µg) |
|---|---|---|
| 1 | MWM | N/A |
| 2 | Capto Adhere Eluate | 10.0 |
| 3 | Mimetic Blue Load | 10.0 |
| 4 | Run 1: Eluate | 10.0 |
| 5 | Run 4: Intermediate wash with 1M Urea | 1.8 |
| 6 | Run 4: Eluate | 10.0 |

| Label | ID | Capto Adhere run # | Test Wash Condition (+ 20mM Tris, 2mM MgCl², 50µM ZnCl²) | Elution buffer NaCl conc. | HCP (ppm) | Normalized HCP | recAP Yield (%) |
|---|---|---|---|---|---|---|---|
| 1 = | Baseline (run 1) | 1 | N/A | 130 mM | 2047 | 1.00 | 103 |
| 9 = | Run 9 | 1 | 1M urea + 20, 40, 60 mM NaCl steps, pH 8.0 | 130 mM | 323 | 0.16 | 15 |
| 10 = | Run 10 | 1 | none (elution buffer control) | none | 862 | 0.42 | 99 |
| 11 = | Run 11 | 1 | (1) 1M urea, pH 8.0<br>(2) 20, 40, 60 mM NaCl steps, pH 8.0 | none | 314 | 0.15 | 26 |
| 12 = | Run 12 | 1 | 20, 40, 60, 80mM arginine steps | none | <40* | 0.02 | 37 |
| 14 = | Run 14 | 2 | none (control for new Capto Adhere wash step) | none | 667 | 0.33 | 88 |
| 16 = | Run 16 | 2 | 20, 40, 60 mM NaCl steps, pH 8.0 | none | 547 | 0.27 | 41 |
| 17 = | Run 17 | 2 | 1M urea + 20, 40, 60 mM NaCl steps, pH 8.0 | none | 212 | 0.10 | 37 |
| 18 = | Run 18 | 2 | 20, 40, 60 mM NaCl steps, pH 7.0 | none | 1042 | 0.51 | 84 |
| 20 = | Run 20 | 2 | 10% ethylene glycol + 20, 40, 60 mM NaCl steps, pH 8.0 | none | 128 | 0.06 | 77 |

* Below LOQ

FIG. 11B

| Gel Lane | Study | Sample ID | Test Condition | recAP conc. (mg/mL) | HCP (ng/mL) | HCP (ppm) |
|---|---|---|---|---|---|---|
| 1 | MVVM | | | | | |
| 2 | 2X diluted Poros Eluate | Load | Baseline | 1.27 | 111,125 | 87,500 |
| 3 | MB run#1 | Eluate | Baseline | 3.38 | 7,389 | 2,047 |
| 4 | MB run#8 | Eluate | 10% eth. Glycol wash | 2.83 | 5,654 | 1,878 |
| 5 | MB run#10 | Eluate | phos only elution | 3.02 | 2,499 | 862 |
| 6 | MB run#10 | Strip | phos only elution | 0.02 | 106,133 | >1,000,000 |
| 7 | MB run#12 | Wash 1 | 20mM arginine step | 0.07 | 4,631 | 62,030 |
| 8 | MB run#12 | Wash 2 | 40mM arginine step | 0.04 | 6,688 | 168,560 |
| 9 | MB run#12 | Wash 3 | 60mM arginine step | 0.10 | 6,540 | 64,303 |
| 10 | MB run#12 | Wash 4 | 80mM arginine step | 0.23 | 14,015 | 61,875 |

FIG. 12A

Anti cat A western blot (10μg)

Silver stain gel (5μg)

| Label | ID | Capto Adhere run # | Test Wash Condition (+ 20mM Tris, 2mM MgCl$^2$, 50µM ZnCl$^2$) | Load density (g recAP/ L resin) | Elution buffer NaCl conc. | HCP (ppm) | Normalized HCP | recAP Yield (%) |
|---|---|---|---|---|---|---|---|---|
| 10= ● | Run 10 | 1 | none (elution buffer control) | 2.2 | none | 862 | 0.42 | 99 |
| 14= ● | Run 14 | 2 | none (control for new Capto Adhere wash step) | 1.8 | none | 667 | 0.33 | 88 |
| 21= | Run 21 | 2 | 1M urea | 1.8 | none | 59 | 0.03 | 83 |
| 22= ● | Run 22 | 2 | 2M urea | 1.8 | none | 299 | 0.15 | 85 |
| 23= | Run 23 | 2 | 40 mM arginine | 1.8 | none | 54 | 0.03 | 83 |
| 24= | Run 24 | 3 | none (control for new load lot) | 2.3 | none | 1145 | 0.56 | 93 |
| 25= | Run 25 | 3 | 10% ethylene glycol + 1M urea | 2.3 | none | 777 | 0.38 | 86 |
| 26= | Run 26 | 3 | 40mM arginine + 1M urea | 2.3 | none | 46 | 0.02 | 71 |
| 27= | Run 27 | 3 | 1M urea | 3.0 | none | 371 | 0.18 | 94 |
| 28= ● | Run 28 | 3 | 40mM arginine | 3.0 | none | 59 | 0.03 | 88 |
| 29= | Run 29 | 3 | 40mM arginine + 1M urea | 3.0 | none | 68 | 0.03 | 66 |

FIG. 13B

Anti cat A western blot (10μg)

Silver stain gel (5μg)

| Gel Lane | Sample ID | Western Load (ug) | Silver Load (ug) |
| --- | --- | --- | --- |
| 1 | MWM | | 0.8 |
| 2 | Capto Adhere catA wash | 1.5 | 5.0 |
| 3 | Capto Adhere Eluate | 10.0 | 2.6 |
| 4 | Poros Load | 5.1 | 5.0 |
| 5 | Poros Eluate | 10.0 | 0.2 |
| 6 | Mimetic Blue catA Wash | 0.5 | 5.0 |
| 7 | Mimetic Blue Eluate | 10.0 | 3.4 |
| 8 | Butyl Eluate | 6.8 | 4.3 |
| 9 | Butyl Strip | 8.6 | 5.0 |
| 10 | UF/DF Retentate | 10.0 | |

FIG. 14C

|  | Product-Related Tests | | Impurity Tests |
| --- | --- | --- | --- |
| ID | Specific Activity (U/mg) | recAP Yield (% recovered) | HCP (ppm) |
| Assay Method | Activity / RP-HPLC |  | ELISA / RP-HPLC |
| CCH Load | 559 | 100 | 952,724 |
| Capto Adhere Eluate | 516 | 93 | 307,976 |
| Poros Eluate | 559 | 61 | 85,484 |
| Mimetic Blue Eluate | 533 | 84 | 34 |
| 3X Diluted HIC Eluate | 502 | 86 | <11 |
| UF/DF Retentate | 543 | 82 | <2 |

\* To prevent dilution of the UF retentate, the membrane buffer flush was not added to the retentate. LVL-RecAP titer of flush was determined but was not analysed for activity.

FIG. 15

|  | Product-Related Tests | | Impurity Tests |
| --- | --- | --- | --- |
| ID | Specific Activity (U/mg) | LVL-RecAP Yield (% recovered) | HCP (ppm) |
| Assay Method | Activity / RP-HPLC |  | ELISA / RP-HPLC |
| 200L PD CCH | 497 | 100 | 837,175 |
| Capto Adhere Eluate | 499 | 99 | 220,191 |
| Poros Eluate | 534 | 63 | 68,454 |
| Mimetic Blue Eluate | 532 | 92 | 36 |
| 3X Diluted HIC Eluate | 484 | 87 | <3 |
| UF/DF Retentate | 548 | 70 | <1 |
| Viral Filtrate | 539 | 98 | <1 |
| BDS | 586 | 98 | <1 |

FIG. 16

FIG. 17

| Demo 6 Stability – Physical Appearance | | | | | | | |
|---|---|---|---|---|---|---|---|
| | T=0 | T = 2 weeks | | | T = 4 weeks | | |
| temperature | n/a | -75°C | 5°C | 25°C | -75°C | 5°C | 25°C |
| Formulation 1 Histidine/ Sorbitol pH 7 | Clear, colorless and free of visible particles | Clear, colorless and free of visible particles | Clear, colorless and free of visible particles | Clear, colorless and free of visible particles | Clear, colorless and free of visible particles | Clear, colorless and free of visible particles | Clear, colorless and free of visible particles |
| Formulation 1 Citrate/ Sorbitol pH 7 | Clear, colorless and free of visible particles | Clear, colorless and free of visible particles | Clear, colorless and free of visible particles | Clear, colorless and free of visible particles | Clear, colorless and free of visible particles | Clear, colorless and free of visible particles | Clear, colorless and free of visible particles |

| | T = 2 Months | | | T = 3 Months | | |
|---|---|---|---|---|---|---|
| temperature | -75°C | 5°C | 25°C | -75°C | 5°C | 25°C |
| Formulation 1 Histidine/ Sorbitol pH 7 | Clear, colorless and free of visible particles | Clear, colorless and free of visible particles | Clear, colorless and free of visible particles | Clear, colorless and free of visible particles | Clear, colorless and free of visible particles | Clear, colorless and free of visible particles |
| Formulation 1 Citrate/ Sorbitol pH 7 | Clear, colorless and free of visible particles | Clear, colorless and free of visible particles | Clear, colorless and free of visible particles | Clear, colorless and free of visible particles | Clear, colorless and free of visible particles | Clear, colorless and free of visible particles |

SEQUENCE OF RECAP    (SEQ ID NO: 1)

1 VIPAEEENPAFWNRQAAEALDAAKKLQPIQKVAKNLILFLGDLGVPTVTATRILKGQKNGKLGPETPLAMDRFPYLALSKTYNVDRQVPDSAATATAYL
101 CGVKANFQTIGLSAAARFNQCNTTRGNEVISVMNRAKQAGKSVGVVTTRVQHASPAGTYAHTVNRNWYSDADMPASARQEGCQDIATQLISNMDIDVIL
201 GGGRKYMFPMGTPDPEYPADASQNGIRLDGKNLVQEWLAKHQGAWYVWNRTELMQASLDQSVTHLMGLFEPGDTKYEILRDPTLDPSLMEMTEAALRLLS
301 RNPRGFYLFVEGGRIDHGHHEGVAYQAVTEAVMFDDAIERAGQLTSEEDTLTLVTADHSHVFSFGGYPLRGSSIFGLAPGKARDRKAYTVLLYGNGPGYV
401 LKDGARPDVTESESGSPEYRQQSAVPLDEETHGGEDVAVFARGPQAHLVHGVQEQSFVAHVMAFAACLEPYTACDLALPACTTD

FIG. 18

SEQUENCE LISTING

```
<160> NUMBER OF SEQ ID NOS: 1

<210> SEQ ID NO 1
<211> LENGTH: 484
<212> TYPE: PRT
<213> ORGANISM: Artificial Sequence
<220> FEATURE:
<223> OTHER INFORMATION: improved recombinant alkaline phosphatase.

<400> SEQUENCE: 1

Val Ile Pro Ala Glu Glu Glu Asn Pro Ala Phe Trp Asn Arg Gln Ala
1               5                   10                  15

Ala Glu Ala Leu Asp Ala Ala Lys Lys Leu Gln Pro Ile Gln Lys Val
            20                  25                  30

Ala Lys Asn Leu Ile Leu Phe Leu Gly Asp Gly Leu Gly Val Pro Thr
        35                  40                  45

Val Thr Ala Thr Arg Ile Leu Lys Gly Gln Lys Asn Gly Lys Leu Gly
    50                  55                  60

Pro Glu Thr Pro Leu Ala Met Asp Arg Phe Pro Tyr Leu Ala Leu Ser
65                  70                  75                  80

Lys Thr Tyr Asn Val Asp Arg Gln Val Pro Asp Ser Ala Ala Thr Ala
                85                  90                  95

Thr Ala Tyr Leu Cys Gly Val Lys Ala Asn Phe Gln Thr Ile Gly Leu
            100                 105                 110

Ser Ala Ala Ala Arg Phe Asn Gln Cys Asn Thr Thr Arg Gly Asn Glu
        115                 120                 125

Val Ile Ser Val Met Asn Arg Ala Lys Gln Ala Gly Lys Ser Val Gly
```

```
            130                 135                 140
Val Val Thr Thr Thr Arg Val Gln His Ala Ser Pro Ala Gly Thr Tyr
145                 150                 155                 160

Ala His Thr Val Asn Arg Asn Trp Tyr Ser Asp Ala Asp Met Pro Ala
                165                 170                 175

Ser Ala Arg Gln Glu Gly Cys Gln Asp Ile Ala Thr Gln Leu Ile Ser
                180                 185                 190

Asn Met Asp Ile Asp Val Ile Leu Gly Gly Arg Lys Tyr Met Phe
                195                 200                 205

Pro Met Gly Thr Pro Asp Pro Glu Tyr Pro Ala Asp Ala Ser Gln Asn
    210                 215                 220

Gly Ile Arg Leu Asp Gly Lys Asn Leu Val Gln Glu Trp Leu Ala Lys
225                 230                 235                 240

His Gln Gly Ala Trp Tyr Val Trp Asn Arg Thr Glu Leu Met Gln Ala
                245                 250                 255

Ser Leu Asp Gln Ser Val Thr His Leu Met Gly Leu Phe Glu Pro Gly
                260                 265                 270

Asp Thr Lys Tyr Glu Ile Leu Arg Asp Pro Thr Leu Asp Pro Ser Leu
    275                 280                 285

Met Glu Met Thr Glu Ala Ala Leu Arg Leu Leu Ser Arg Asn Pro Arg
    290                 295                 300

Gly Phe Tyr Leu Phe Val Gly Gly Arg Ile Asp His Gly His His
305                 310                 315                 320

Glu Gly Val Ala Tyr Gln Ala Val Thr Glu Ala Val Met Phe Asp Asp
                325                 330                 335

Ala Ile Glu Arg Ala Gly Gln Leu Thr Ser Glu Glu Asp Thr Leu Thr
                340                 345                 350

Leu Val Thr Ala Asp His Ser His Val Phe Ser Phe Gly Gly Tyr Pro
                355                 360                 365

Leu Arg Gly Ser Ser Ile Phe Gly Leu Ala Pro Gly Lys Ala Arg Asp
                370                 375                 380

Arg Lys Ala Tyr Thr Val Leu Leu Tyr Gly Asn Gly Pro Gly Tyr Val
385                 390                 395                 400

Leu Lys Asp Gly Ala Arg Pro Asp Val Thr Glu Ser Glu Ser Gly Ser
                405                 410                 415

Pro Glu Tyr Arg Gln Gln Ser Ala Val Pro Leu Asp Glu Glu Thr His
                420                 425                 430

Gly Gly Glu Asp Val Ala Val Phe Ala Arg Gly Pro Gln Ala His Leu
                435                 440                 445

Val His Gly Val Gln Glu Gln Ser Phe Val Ala His Val Met Ala Phe
                450                 455                 460

Ala Ala Cys Leu Glu Pro Tyr Thr Ala Cys Asp Leu Ala Leu Pro Ala
465                 470                 475                 480

Cys Thr Thr Asp
```

DOWNSTREAM PROCESSING OF AN ALKALINE PHOSPHATASE

REFERENCE TO A SEQUENCE LISTING SUBMITTED ELECTRONICALLY VIA EFS-WEB

This application includes a Sequence Listing submitted electronically via EFS-Web (name: "3151_0090001_Seq-Listing_.txt"; size: 4,559 bytes; and created on: Jul. 14, 2016), which is hereby incorporated by reference in its entirety.

FIELD

The invention relates to the field of downstream processing (DSP) of an alkaline phosphatase (AP). More specifically, it relates to a method for reducing host cell protein content in a composition comprising AP. The invention further relates to a composition comprising an AP and a reduced content of a host cell protein.

INTRODUCTION

Alkaline Phosphatase (AP)

AP; EC 3.1.3.1 according to IUBMB Enzyme nomenclature, the common name is alkaline phosphatase (AP), is an enzyme that catalyzes the reaction of a phosphatase monoester and $H_2O$ to an alcohol and phosphate. Other name(s) for AP are alkaline phosphomonoesterase; phosphomonoesterase; glycerophosphatase; alkaline phosphohydrolase; alkaline phenyl phosphatase; orthophosphoric-monoester phosphohydrolase (alkaline optimum). The systemic name of AP is phosphate-monoester phosphohydrolase (alkaline optimum).

AP is a broad specificity enzyme, it also catalyses transphosphorylations. In humans and other mammals at least four distinct, but related alkaline phosphatases are known. These are intestinal (ALPI), placental (ALPP; only in human and primates), placental-like (GCAP), and liver/bone/kidney (or tissue non-specific) alkaline phosphatase (TNAP). The first three are located together on chromosome 2 while the tissue non-specific form is located on chromosome 1.

The amino acid sequence of alkaline phosphatases and the relative positions of the catalytic and crown domains are known by the skilled person. As an example, reference is made to the textbook on mammalian alkaline phosphatases by Millán (Mammalian Alkaline Phosphatases, Wiley-VCH (2006), ISBN-13: 978-3-527-31079-1) which shows, amongst others, the amino acid sequence of the four human alkaline phosphatases.

AP for Pharmaceutical Use

Previously it has been shown that AP is beneficial as a medicament in a wide range of diseases (Acute Kidney Injury (AKI), Sepsis, Inflammatory Bowel Disease (IBD), etc.). These studies have used naturally occurring APs, such as isolated bovine as well as isolated and recombinant human AP. In some animal models, a recombinant chimeric alkaline phosphatase has been used that comprises the catalytic domain of a human intestinal AP and a crown domain of a human placental AP (described in WO2008133511). At present, a pharmaceutical composition comprising a novel and improved recombinant chimeric alkaline phosphatase having a sequence as depicted in FIG. 18 (SEQ ID NO: 1) is being developed for use as a medicament.

During development of the pharmaceutical composition, use was made of standard (DSP) processes for protein, and in particular AP, such as affinity (Mimetic Blue AP®), anion exchange (Poros 50 HQ®), and mixed mode (Capto-Adhere®) chromatography. After the DSP steps were optimized and the pharmaceutical composition complied with the specifications that were previously laid down and required by regulatory authorities, preparations were made for clinical batch production. However, during final stage stability testing, particle formation was observed.

This was an unforeseen problem and because particle formation is an unwanted aspect in pharmaceutical compositions, a solution had to be found.

It was unclear what the identity of the particles was and upon collection of the particulates by centrifugation and analysis, a non-AP band on silver stained non-reducing SDS-PAGE gels was enriched. Mass spec analysis of enzymatic digests of this band revealed the presence of host cell protein (HCP) but not AP. This was in particular not foreseen because, according to the previous tests for host cell protein, there was too little amount of HCP (<100 ppm) in the composition to explain the relatively large amount of particles.

Host Cell Proteins (HCP)

HCP are proteins that are produced or encoded by cells or organisms that are used in the production process and are unrelated to the intended product. Some are necessary for growth, survival, and normal cellular processing whereas others may be non-essential. Like the intended product, HCPs may also be modified by the host with a number of post-translational modifications. Regardless of the utility, or lack thereof, HCPs are generally undesirable in a final drug substance. Though commonly present in small quantities (parts per million expressed as nanograms per milligrams of the intended protein) much effort and cost is expended by industry to remove them. (Wang et al; Biotechnology and Bioengineering, Vol. 103, No. 3, Jun. 15, 2009).

Prior to the approval of a biological product for therapeutic use, the level of residual HCP in the product must be quantitatively measured, according to the "Points to Consider" documents issued by the U.S. Food and Drug Administration or the European Commission's "Notes for Guidance". Thus, HCP must be typically eliminated and elimination must be demonstrated during DSP. Current analytical methods to assay for the presence of contaminant HCPs in recombinant biological products include SDS-PAGE, immunoblotting techniques and ELISA. There are many publications on the removal of HCP contamination and removal, for instance using for instance hydrophobic interaction chromatography (Shukla et al, Biotechnol. Prog. 2002, 18, 556-564), Protein A chromatography (Shukla et al, Biotechnol. Prog. 2008, 24, 11151121), or salt tolerant anion exchange ligands (Riordan et al, Biotechnol. Prog. 2009, Vol. 25, No. 6).

There is thus a need for an optimized DSP and formulation in order to provide a pharmaceutical composition comprising an alkaline phosphatase with reduced HCP content and improved physical stability.

The present inventors have adapted both the DSP and final drug formulation in order to a) reduce the content of HCP and b) reduce the particle formation observed. The primary objective of the DSP adaptation is decreasing HCP content whereas the primary objective of the formulation adaptation is decreasing the formation of (visible) particles, due to any remaining HCP. Both, DSP adaptation as well as the formulation adaptation, synergize in decreasing particle formation during stability testing, thus improving physical stability of the pharmaceutical composition. At least when combined, the improved DSP and the new formulation results in a pharmaceutical composition, wherein the composition is reduced in HCP content and wherein no visible particle formation occurs during stability testing.

In a first embodiment, the invention provides a method for producing a composition comprising an isolated alkaline phosphatase and comprising a reduced content of host cell protein (HCP), preferably less than 100 ppm HCP, the method comprising a first purification step comprising the steps of:
providing a solid phase comprising a ligand having the formula:

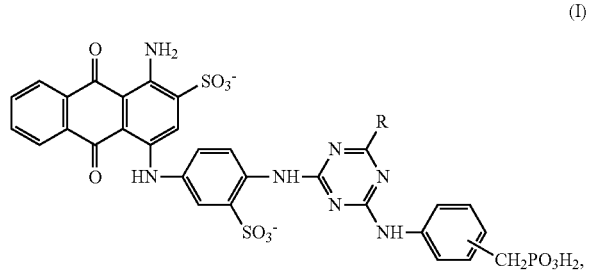

(I)

wherein R denotes a spacer which links the ligand to the solid phase,
contacting said ligand with a composition comprising an isolated AP having at least 90% sequence identity with SEQ ID NO: 1 and a HCP,
performing several wash steps, wherein at least one wash step is performed using a wash buffer capable of detaching at least part of the HCP from the ligand while retaining at least part of the AP bound to the ligand, and
obtaining AP using an elution buffer capable of detaching at least part of said AP from the ligand. Preferably, at least part of the HCP is retained bound to the ligand or at the solid phase, while performing this last step.

The percentage of identity of an amino acid or nucleic acid sequence, or the term "% sequence identity", is defined herein as the percentage of residues in a candidate amino acid or nucleic acid sequence that is identical with the residues in a reference sequence after aligning the two sequences and introducing gaps, if necessary, to achieve the maximum percent identity. In a preferred embodiment, the calculation of said at least percentage of sequence identity is carried out without introducing gaps. Methods and computer programs for the alignment are well known in the art, for example "Align 2" or the BLAST service of the National Center for Biotechnology Information (NCBI).

The DSP comprises a purification step involving affinity purification, using a known ligand for an alkaline phosphatase having the formula:

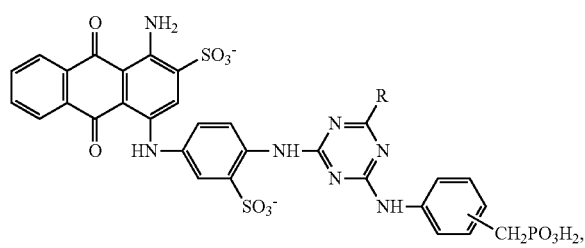

(I)

wherein R is either a reactive group or a spacer that is linked to a solid phase, wherein the washing steps have been optimized to achieve high purity and yield with reduced HCP content in order to optimize the physical stability of the resulting AP containing composition. The ligand of formula (I) is, in the form of a column, commercially available under the trademark Mimetic Blue AP™ (MMBAP; Prometic, UK), wherein R is a spacer molecule that serves to create a distance between the solid phase matrix of the column and the ligand. This distance enables the efficient binding of the large AP molecule to the ligand.

The ligand of formula I is known in the art, and is for instance described in Lindner et al (J Chromatography, 473 (1989) 227-240; FIG. 1, compound IV) for the purification of calf intestinal alkaline phosphatase (CIAP). Lindner et all have shown that the ligand is useful in the DSP of intestinal alkaline phosphatase (ALPI). However, Lindner does not describe reduction of HCP, amongst others while Lindner was not faced with the problem of HCP contamination because they did not purify the AP for therapeutical use. Using standard wash and elution buffers for purification, Lindner et al achieved a 330 fold purification of CIAP. As the inventors found out, the conditions recited in Lindner, however, do not resolve the problem of particle formation and HCP contamination observed during DSP for pharmaceutical manufacturing.

For the present application, with "host cell" is meant an animal or human cell containing an active (optionally modified) AP gene and this AP gene is transcribed and translated in the cell, either in vivo (e.g. in a non-human animal) or in vitro (cell culture). The AP gene can be introduced into this host cell as an exogenous gene, preferably with regulatory elements, already be present in the host cell as an active endogenous gene or become activated as an endogenous non-active gene. Such an activation of endogenous genes can for example be achieved by the specific introduction of regulation elements into the genome for example by homologous recombination.

Mammalian cells are usually used as host cells. If an exogenous AP gene is introduced, Chinese Hamster Ovary (CHO) or Human Embryonic Kidney (HEK) cells can for example be used as host cells. HCPs can be present in a preparation obtained from an (unmodified) animal cell expressing an endogenous AP, in which case the AP protein obtained is typically designated "purified" or "isolated". In contrast, a "recombinant" protein is generally considered a protein expressed by a cell comprising an exogenous, optionally modified, AP gene, or by a cell expressing AP through homologous recombination, as defined above. A recombinant protein can also be designated "isolated", e.g., when it is purified. It is to be understood that the method according to the invention can be used for both endogenously expressed, as well as recombinantly expressed AP. It should be noted that the term "isolated" and "purified" may be used in the course of DSP of a recombinant protein to denote the different purification steps, such as the isolation from the cells and the purification of the protein to remove contaminants. As used in the present application, the term isolated and purified can have the latter meaning, depending on the context of the use of these terms.

For a composition comprising a novel and improved recombinant alkaline phosphatase, however, the standard purification methods did not lead to sufficient HCP removal. In addition, commercial tests that were used for HCP measurement underestimated the HCP content, especially because of the fact that the AP co-purified with the HCP, amongst others because both have a similar isoelectric point and possibly because the HCP was bound to AP during purification. The presence of the HCP in the composition further resulted in particle formation that is also an unwanted occurrence in a pharmaceutical composition, amongst other because particles may comprise insoluble protein aggregates, which are more immunogenic than soluble protein.

The inventors, now faced with the problems, that the composition intended for pharmaceutical use contained a relatively high concentration of HCP, and formed particles upon storage, sought for a solution.

One problem to be solved is, therefore, the provision of a composition comprising a particular recombinant alkaline phosphatase, which composition comprises a low content of HCP and preferably does not show visible particle formation during stability testing at 2-8° C. for 2 months. With visible particle formation is meant that particle(s) can be observed with the naked eye by a person skilled in the art, optionally using a means for magnification, such as a magnifying glass. In the regulatory world, there is a distinction between visible and non-visible particulate matter. Visible particulate is loosely defined as any particulate that can be detected with the unaided eye. Typically, visible objects are defined as objects that are 0.05 mm or larger. With the term "visible particles", as used in the present invention, is meant: particles that are 0.05 mm or larger, preferably 0.1 mm or larger, more preferably 0.2 mm or larger, more preferably 0.5 mm or larger, most preferably 1 mm or larger.

It is also possible to detect visible particle formation with equipment designed to detect such visible particles. The most common approach to automating the inspection for particulate in a clear solution, as is with the composition (obtained by a method) according to the invention, is to agitate the solution and image the solution over time. The imaging system generally consists of a machine vision camera, illumination (in this case backlighting) and a vision processor to analyze the images. Once the images have been acquired, they are then analyzed in sequence for image-to-image differences. The differences can be interpreted as objects moving inside the solution such as gas bubbles and particulate. In the case of larger, denser particulate, detection is achieved by filtering out the gas bubbles from the analysis, as they will rise up while the particulate sinks.

If the goal is to find particulate, smaller than about 1 mm in diameter, a more careful approach to agitation must be used to remove gas bubbles from the field of view. This can be done by agitating the solution through spinning, with careful attention to acceleration and deceleration rates.

For the purpose of the present invention, however, the method of detection is not important for defining "visible particles" as long as the particles have a diameter as defined above.

As described above, the standard DSP and formulation for the recombinant alkaline phosphatase did not result in such composition as the HCP content exceeded the generally used norm of 100 ppm by far and during stability test, particle formation was observed.

To meet regulatory norms, a method according to the invention preferably results in a composition comprising less than 100 ppm HCP, relative to the alkaline phosphase content.

In a preferred embodiment, the washing buffer further comprises $MgCl_2$, $ZnCl_2$ and Tris. These components are not required for removing HCP during the novel and inventive washing step, but are beneficial for the stability properties of alkaline phosphatase in general, for AP being a pH sensitive metal-binding enzyme. Preferably, Mg is present at a concentration above 0.1 mM. Preferably the Mg concentration does not exceed 100 mM. The Mg concentration is preferably between 0.1-100 mM, more preferably between 0.5-20 mM, more preferably between 1-5 mM, most preferably about 2 mM. Zn is preferably present in a concentration above 10 µm. Preferably the Zn concentration does not exceed 1 mM. The Zn concentration is preferably between 10-1000 µM, more preferably between 20-100 µM, more preferably between 40-60 µM, most preferably about 50 µM.

The solid phase may for instance be a resin and is typically in the form of a column, which is as such commercially available. Use of a column in a method according to the invention is preferred as it is easily upscalable in a DSP setting. A column suitable in a method of the invention is, e.g., Mimetic Blue AP®. It is however also possible to use a for instance beads comprising said ligand and perform the steps of contacting and washing through centrifugation, decanting and dissolution. It is also possible to use magnetic beads and magnetic separation during the washing steps. A person skilled in the art is familiar with the different processes for affinity purification and can easily adapt such processes for use in a method according to the invention.

Typically, the ligand is attached to the solid phase using a spacer, represented by R in formula (I). Such spacers are known in the art and any suitable spacer, such as hexamethyl diamine (1,6-diaminohexane) (Dye-Ligand Affinity Absorbents for Enzyme Purification N.E. Labrou Molecular Biotechnology Vol 20, 2002 p 77-84) or 3',3'-diaminodipropylamine.

In a preferred embodiment, the invention provides a method according to the invention, wherein the wash buffer comprises between 20-100 mM Arg, preferably between 30-50 mM Arg, most preferably about 40 mM Arg.

The inventors have surprisingly shown that by incorporating the above washing step in the standard DSP process for AP, it is now possible to decrease the HCP content to a value below 100 ppm in the final composition. The described washing step thus enables the provision of a composition that complies with the rules laid down for pharmaceutical composition in this respect and as such has a content of less than 100 ppm HCP. Such composition could not be obtained before the present invention, because standard (optimized) DSP steps that did not make use of the novel and inventive DSP steps of the present invention, did not result in a composition comprising less than 100 ppm HCP. Further, such composition, when stored at 2-8° C. for 2 months, does not show visible particle formation, whereas compositions prepared by standard optimized DPS steps did.

The inventors have further shown that a washing buffer comprising between 0.5-2 M urea, preferably between 1-2 M urea, more preferably about 1 M urea, when used in a method according to the invention resulted in reduced HCP content as well. A washing buffer comprising both urea and Arg also gave very good results. Further provided is therefore, a method according to the invention, wherein the washing buffer comprises between 0.5-2 M urea, preferably between 1-2 M urea, more preferably about 1 M urea. Preferably, the washing buffer comprises both Arg and urea in a concentration as described above.

The addition of 5-15%, preferably about 10% ethylene glycol, to the washing buffer provided good results as well. Therefore, the invention provides a method according to the invention, wherein the washing buffer comprises between 5-15% ethylene glycol, preferably about 10% ethylene glycol.

The invention further shows that in order to increase HCP reduction and/or improve yield of the AP, the washing buffer is preferably free of NaCl. In a preferred embodiment, therefore a method according to the invention is provided, wherein the washing buffer, preferably comprising Arg, urea, ethylene glycol or any combination thereof in a concentration as described above, is substantially free of NaCl. With substantially free of NaCl is meant that the washing buffer preferably comprises less 1 mM, more preferably less than 100 µM more preferably less than 10 µM, more preferably less than 1 µM, more preferably less than 100 nM, more preferably less than 10 nM, most preferably less than 1 nM NaCl.

With reduced content is meant that, the ratio HCP:AP is lower after employing a method according to the invention when compared with a similar method wherein no Arg, urea or ethylene glycol is used during washing and wherein NaCl is present in a substantial amount (e.g. more than 1 mM) in the washing buffer. Preferably, a method according to the invention, when incorporated in the complete set of DSP steps results in a HCP content, relative to AP content, of less than 100 ppm, more preferably less than 50 ppm, more preferably less than 20 ppm, more preferably less than 10 ppm, more preferably less than 5 ppm, more preferably less than 2 ppm, more preferably less than 1 ppm.

Similarly, with improved yield is meant that the yield of AP, measured in percentage $AP_{out}$ vs $AP_{in}$ is higher, relative to a method that does not use a washing step according to the invention, wherein $AP_{out}$ is the amount of AP that is obtained after the process step and $AP_{in}$ is the amount of AP which is contacted with the ligand before washing.

Next to the washing step in a method according to the invention, the eluting step has also been improved over the methods known in the art prior to the present invention. According to the invention, the elution buffer used in a method according to invention, preferably comprises less than 100 mM NaCl in order to efficiently detach at least part of the AP from the ligand having structure formula (I). The best results have been achieved by using the combination of a washing buffer comprising about 40 mM Arg, having a pH of about 8 and is substantially free of NaCl, and an elution buffer which is preferably substantially free of NaCl. In a preferred embodiment, therefore, a method according to the invention is provided, wherein the washing buffer comprises about 40 mM Arg and has a pH of about 8, and wherein both the washing buffer and the elution buffer are substantially free of NaCl. With substantially free of NaCl is meant that the washing buffer and/or elution buffer preferably comprise less than 1 mM, more preferably less than 100 µM, more preferably less than 10 µM, more preferably less than 1 µM, more preferably less than 100 nM, more preferably less than 10 nM, most preferably less than 1 nM NaCl.

Next to the affinity DSP step described above, the complete DSP for (an) alkaline phosphatase typically comprises further steps for purification. One such step is a so called mixed mode purification step using a ligand as described by structural formula (II) below. The ligand is known in the art as "Capto Adhere" and combines both hydrophobic interaction as well as ion-exchange purification. The present inventors have adapted the washing conditions while performing the mixed mode purification step in order to further decrease the HCP content with optimal yield.

In a preferred embodiment, the invention thus provides a method according to the invention, the method further comprising a second purification step, comprising the steps of:
  providing a second solid phase comprising a second ligand having the formula:

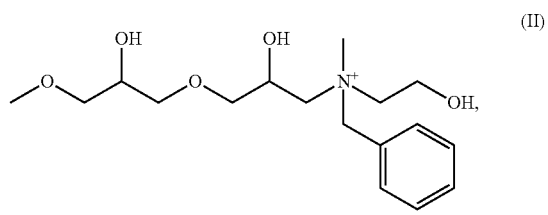 [SMILES: COCC(O)COCC(O)C[N+](C)(CCO)Cc1ccccc1]

contacting said second ligand with a composition comprising an isolated AP and a HCP, and
  performing several wash steps, wherein at least one wash step is performed using a second washing buffer having a pH between 7.5-8.5, preferably between 7.8 and 8.2, more preferably about 8.0, and comprising between 0.05 and 0.2 M NaCl, preferably about 0.1 M NaCl and between 0.1 and 0.5 M L-Arg, preferably between 0.15 and 0.3 M L-Arg, more preferably about 0.2 M L-Arg. In a preferred embodiment, said second washing buffer further comprises between 1-20%, preferably between 2-10%, more preferably between 4-6%, most preferably about 5% glycerol.

The solid phase may, again, for instance be a resin and is typically in the form of a column, which are as such commercially available. Use of a column in a method according to the invention is preferred as it is easily upscalable in a DSP setting. A resin suitable in a method of the invention is, e.g., Capto-Adhere®, which can be used in the form of a column. It is however also possible to use for instance beads comprising said ligand and perform the steps of contacting and washing through centrifugation, decanting and dissolution. It is also possible to use magnetic beads and magnetic separation during the washing steps. A person skilled in the art is familiar with the different processes for affinity purification and can easily adapt such processes for use in a method according to the invention.

Although the sequence of DSP steps may be varied to adapt to efficiently process the composition, in a preferred embodiment, said second purification step precedes, i.e. is performed before, said first purification step. The complete DSP for the alkaline phosphatase can and preferably does include other purification steps, known in the art, such as anion exchange chromatography, ultrafiltration/diafiltration, viral filtration, size exclusion chromatography, affinity chromatography and hydrophobic interaction chromatography, and any combination thereof.

In a preferred embodiment, the method according to the invention comprises at least three, preferably at least 5, more preferably all of the following steps, preferably in the order as listed below:
  Mixed Mode Chromatography (e.g. Capto Adhere (formula II))
  Detergent-based Viral inactivation (e.g. Triton X-100)
  Anion Exchange Chromatography (e.g. Poros 50 HQ)
  Affinity Chromatography (e.g. Mimetic Blue AP (formula I))
  Hydrophobic Interaction Chromatography (e.g. Butyl 650 M)
  Ultrafiltration/Diafiltration
  Virus Filtration
  Bulk Fill In one embodiment, the invention further provides a formulation step that results in improved physical stability of an isolated AP composition, preferably already having reduced HCP content, such that reduced particle formation, preferably no visible particle formation, occurs during stability testing. Preferably, a method according to the invention for producing a composition comprising an isolated alkaline HCP phosphatase and comprising a reduced content of HCP precedes said formulation step according to the invention.

In a preferred embodiment said formulation step comprises the dissolution or dilution of the eluted AP in a buffer such that the resulting composition has a pH of between 6.5 and 7.5, preferably between 6.8 and 7.2, more preferably about 7.0, preferably comprising between 200-300 mM sorbitol, more preferably between 225-275 mM sorbitol, most preferably about 250 mM sorbitol, and/or comprising between 10-40% glycerol, more preferably between 20-30% glycerol, most preferably about 25% glycerol. In a preferred embodiment, the composition comprises between 10-40 mM citrate, more preferably between 15-30 mM citrate, most preferably about 20 mM citrate. In another preferred embodiment, the composition comprises between 5-40 mM histidine, more preferably between 10-30 mM histidine, more preferably between 15-25 mM histidine, most preferably about 20 mM histidine.

The invention thus provides a method for producing a physically stable composition comprising an isolated alkaline phosphatase (AP), the method comprising dissolving or diluting AP in a buffer, resulting in a composition having a pH of between 6.5 and 7.5 and preferably comprising between 200-300 mM sorbitol and/or between 10-40% glycerol. Preferably said composition comprises between 5-40 mM histidine and/or between 10-40 mM citrate.

In a preferred embodiment, the composition comprising AP comprises less than 100 ppm HCP. Preferably, said composition comprises the eluted AP obtained by a method according to the invention for producing a composition comprising an isolated alkaline phosphatase and comprising a reduced content of HCP.

In a preferred embodiment, therefore, the invention provides a method according to the invention for producing a composition comprising an isolated or recombinant alkaline phosphatase and comprising a reduced content of HCP, further comprising the step of dissolving or diluting the AP obtained therein in a buffer, resulting in a composition having a pH of between 6.5 and 7.5, preferably between 6.8 and 7.2, more preferably about 7.0, and preferably comprising between 200-300 mM sorbitol, more preferably between 225-275 mM sorbitol, most preferably about 250 mM sorbitol and/or between 10-40% glycerol, more preferably between 20-30% glycerol, most preferably about 25% glycerol. In a preferred embodiment, the composition comprises between 10-40 mM citrate, more preferably between 15-30 mM citrate, more preferably about 20 mM citrate, and/or between 5-40 mM histidine, more preferably between 10-30 mM histidine, more preferably between 15-25 mM histidine, most preferably about 20 mM histidine.

Preferably, the buffer wherein the AP is dissolved or diluted to obtain the composition comprises a magnesium (Mg) salt, such as $MgCl_2$ and/or a zinc (Zn) salt, such as $ZnCl_2$. Preferably, Mg is present in the composition at a concentration of more than 0.1 mM. Preferably the Mg concentration does not exceed 100 mM. The Mg concentration is preferably between 0.1-100 mM, more preferably between 0.5-20 mM, more preferably between 1-5 mM, most preferably about 2 mM. Zn is preferably present in a concentration above 10 µm. Preferably the Zn concentration does not exceed 1 mM. The Zn concentration is preferably between 10-1000 µM, more preferably between 20-100 µM, more preferably between 40-60 µM, most preferably about 50 µM. As discussed previously, the Mg and Zn salts do not necessarily influence the physical stability of the composition in terms of visible particle formation but, being a metal-coordinating enzyme, AP is in general more stable when Zn and Mg ions are present. The composition may further comprise NaCl, preferably in a physiologic concentration, i.e. about 0.9% w/v NaCl. This is especially useful when the composition is for use as a medicament, in particular when used for intravenous administration.

Although the method according to the invention may be applied to other recombinant proteins as well, a method according to the invention is preferably performed using a composition comprising an alkaline phosphatase having an amino acid sequence having at least 90% sequence identity, preferably having at least 95% sequence identity, more preferably having at least 98% sequence identity, more preferably having at least 99% sequence identity, most preferably having 100% sequence identity with the amino acid sequence of SEQ ID NO: 1. In a preferred embodiment, the host cell protein is a mammalian host cell protein, preferably a cathepsin-like protein (catA), more preferably a hamster homologue of Cathepsin A, and/or the recombinant alkaline phosphatase is expressed in a cell-based expression system, preferably comprising a mammalian host cell, more preferably a CHO host cell.

Now that the invention provides a method for producing a composition comprising an isolated alkaline phosphatase and comprising a reduced content of host cell protein, the invention further provides such composition, obtainable by a method according to the invention.

In one embodiment, therefore, the invention provides a composition comprising an isolated alkaline phosphatase and a pharmaceutically acceptable excipient, characterized in that the composition comprises less than 100 ppm of a host cell protein, more preferably less than 50 ppm, more preferably less than 20 ppm, more preferably less than 10 ppm, more preferably less than 5 ppm, more preferably less than 2 ppm, most preferably less than 1 ppm or lower. Preferably the composition does not show substantial visible particle formation during stability testing at 2-8° C., preferably at about 5° C. for 2 months, more preferably for 3 months. With no substantial visible particle formation is meant that the <20 visible particles are formed in 1 mL of composition. Preferably, 15 or less particles, more preferably 10 or less, more preferably 5 or less, most preferably less than 1 particles per 1 mL composition are formed during stability testing at the conditions specified for storage of the composition.

Preferably, the composition according to the invention is obtained or obtainable by a method according to the invention. Preferably, the composition has a pH of between 6.5-7.5, preferably about 7 and preferably comprises between 10-40 mM, preferably between 15-30 mM, more preferably about 20 mM citrate and/or between 10-40%, preferably between 20-30, more preferably about 25% glycerol, and/or between 200-300 mM, preferably between 225-275 mM, more preferably about 250 mM sorbitol, and/or between 5-40 mM histidine, preferably between 10-30, most preferably about 20 mM histidine. In a preferred embodiment, the composition has a pH of between 6.5-7.5, preferably about 7 and comprises between 10-40 mM citrate, preferably about 20 mM or between 5-40 mM histidine, preferably about 20 mM. The inventors have observed excellent physical stability, i.e. no substantial visible particle formation during stability testing at 2-8° C. for 2 months using such formulated composition. As described above, the term "visible particle" as used herein denotes particles that are 50 μm in diameter or more, preferably 100 μm or more, more preferably 500 μm or more, most preferably 1 mm or more. The particles can be either observed by the naked eye, optionally using magnifying means or by an automated process, such as for instance a film camera and suitable means for analyzing the film material, as described before.

In a preferred embodiment, the composition according to the invention comprises an isolated alkaline phosphatase that has been expressed in a cell-based expression system, preferably comprising a mammalian host cell, more preferably comprising a CHO host cell. In a preferred embodiment, the HCP is a cathepsin-like protein, more preferably a hamster homologue of Cathepsin A.

Preferably, the alkaline phosphatase has a sequence having at least 90% sequence identity, more preferably at least 95% sequence identity, more preferably at least 98% sequence identity, more preferably at least 99% sequence identity, most preferably 100% sequence identity with the amino acid sequence of SEQ ID NO: 1. Now that the invention provides a method for reducing HCP and a composition comprising an isolated alkaline phosphatase and comprising less than 100 ppm HCP, the invention further provides a composition according to the invention for use as a medicament.

A composition according to the invention for use as a medicament is preferably for use in the treatment of alkaline phosphatase related diseases. With alkaline phosphatase related diseases is meant, a disease or condition that is related to a deficiency in alkaline phosphatase, or a disease or condition that can be improved by the exogenous administration of alkaline phosphatase. In particular, an alkaline phosphatase related disease can be any one of the following diseases: sepsis or septic shock, inflammatory bowel disease or other inflammatory diseases of the gastro-intestinal tract, (acute) kidney injury or other renal diseases, ischemic reperfusion conditions, (surgical) traumata, and hypophosphotasia.

The invention will be explained in more detail in the following, non-limiting examples.

FIGURES LEGENDS

FIG. 1. Particle formation in alkaline phosphatase composition formulated in the indicated buffer on days 0-7. y-Axis depicts the qualitative particle formation wherein: 1=~10 particles/mL; 2=10-15 particles/mL AND/OR larger particles; 3=~15 particles/mL AND/OR mostly larger particles; 4=15-20 particles/mL AND/OR much larger particles; 5=~20 particles/mL AND/OR much larger particles; 6=~30 particles/mL AND/OR much larger particles; 7=30-40 particles/mL AND/OR much larger particles; 8=40-50 particles/mL AND/OR much larger particles. Within each set of bars (for each set within A, within B, within C, etc) the order (from left to right) as indicated in the legend, i.e. first bar=day 0, second bar=day 1, etc. A, B, C, etc denote the different excipients, as explained in Table 2.

Figure 2:
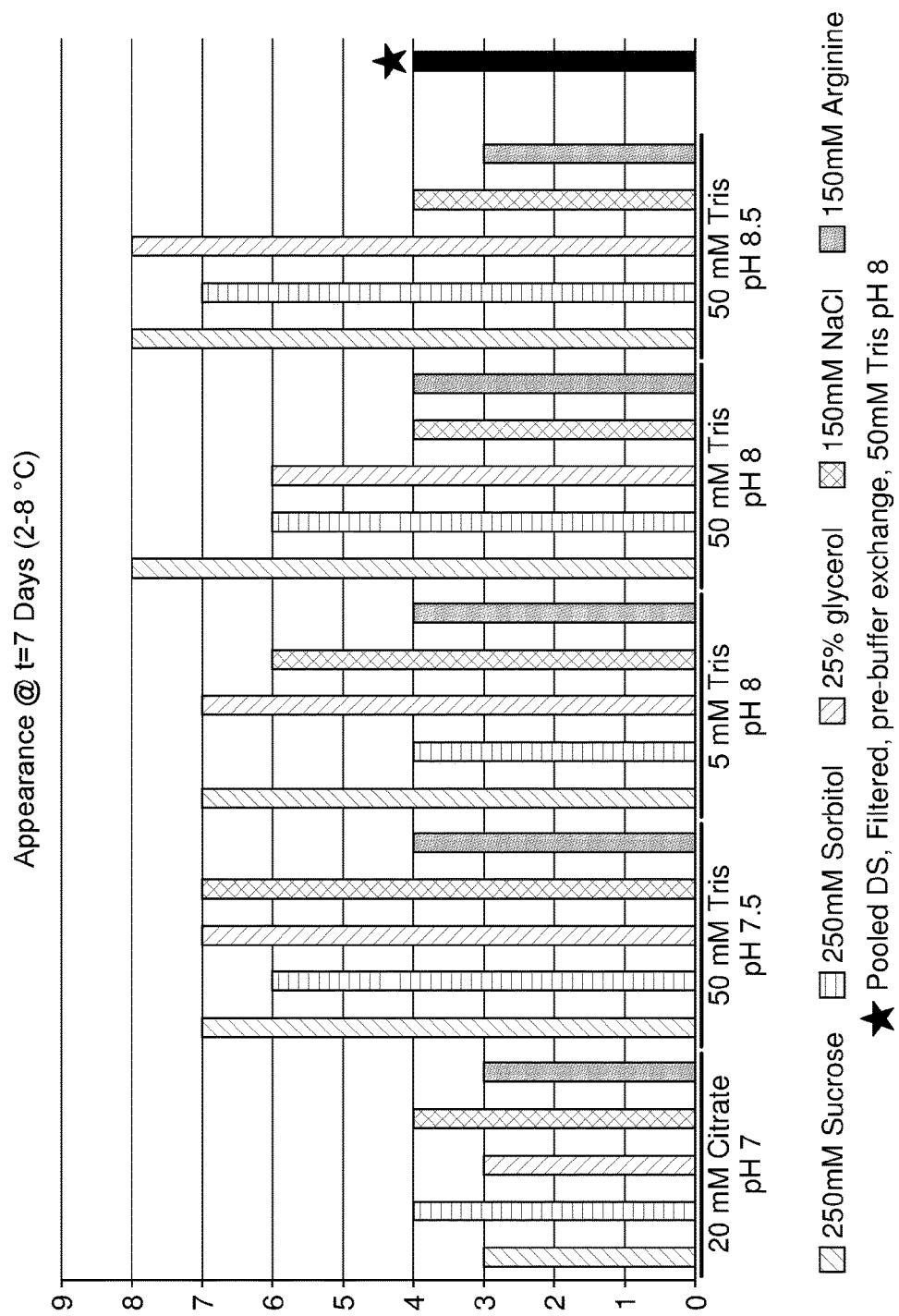

FIG. 2. Particle formation in alkaline phosphatase composition formulated in the indicated buffer on day 7. y-Axis depicts the qualitative particle formation wherein: 1=~10 particles/mL; 2=10-15 particles/mL AND/OR larger particles; 3=~15 particles/mL AND/OR mostly larger particles; 4=15-20 particles/mL AND/OR much larger particles; 5=~20 particles/mL AND/OR much larger particles; 6=~30 particles/mL AND/OR much larger particles; 7=30-40 particles/mL AND/OR much larger particles; 8=40-50 particles/mL AND/OR much larger particles.

Figure 3:
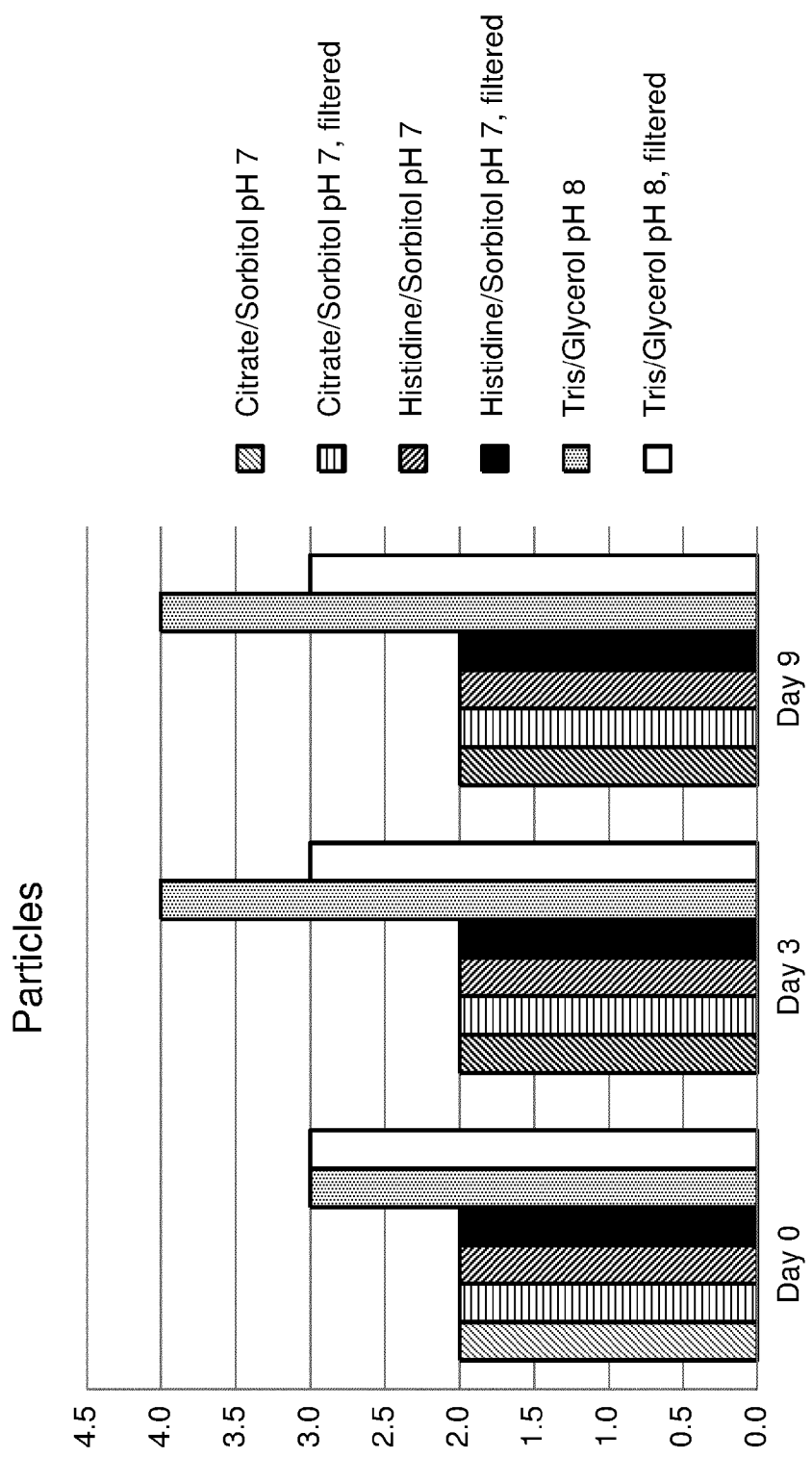

FIG. 3. Particle formation in alkaline phosphatase composition formulated in the indicated buffers. y-Axis depicts the qualitative particle formation wherein: 1=no visible particles; 2=1-5 small particles/mL; 3=6-15 small particles/mL; and 4=16-25 small particles/mL.

Figure 4:
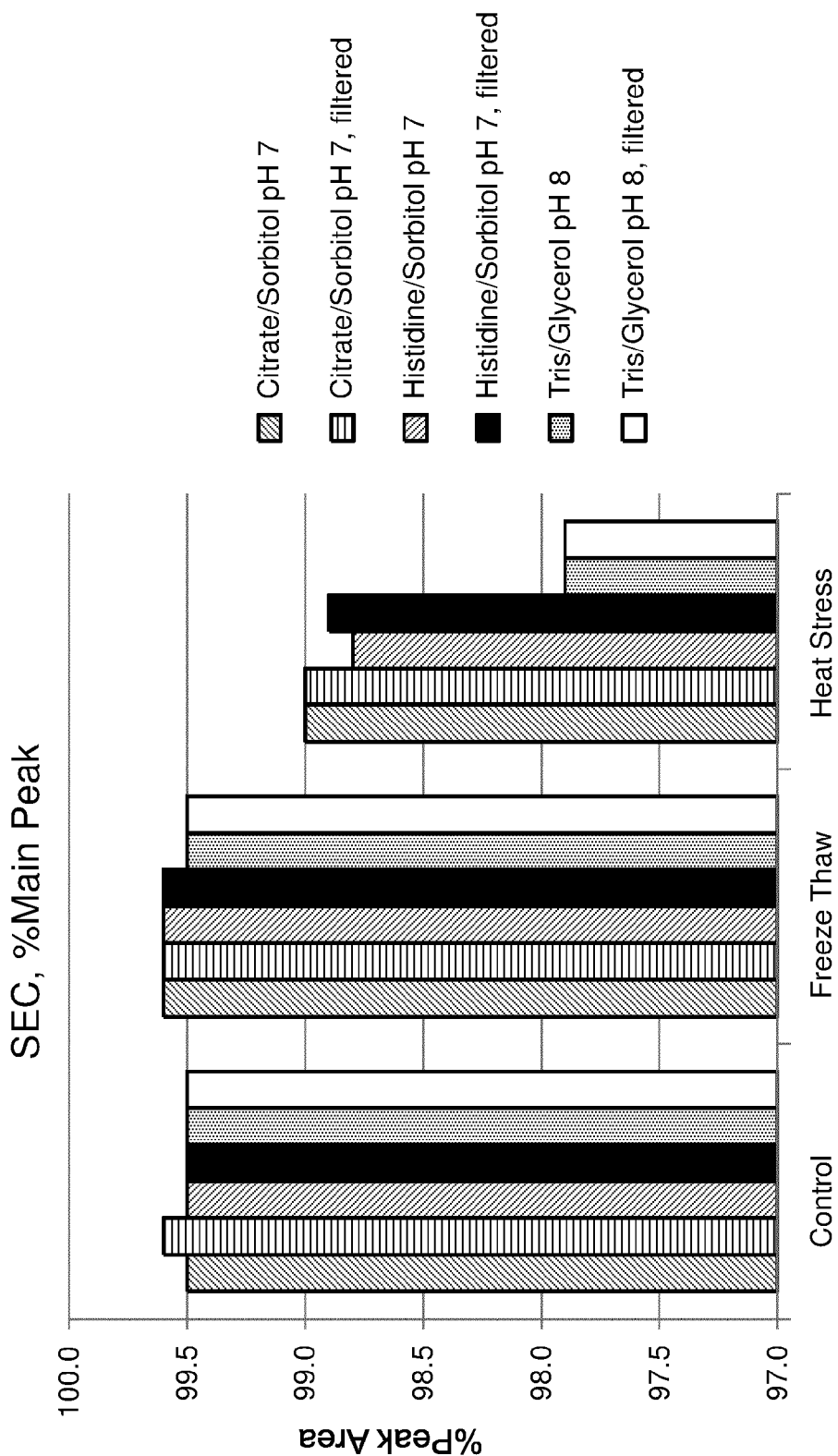

FIG. 4. Effect of physical stress conditions on formation of High Molecular Weight (HMW) species of recAP in different formulations. Graphical representation of percentage main peak and percentage HMW of recAP protein as determined by Size Exclusion Chromatography.

Figure 5A:
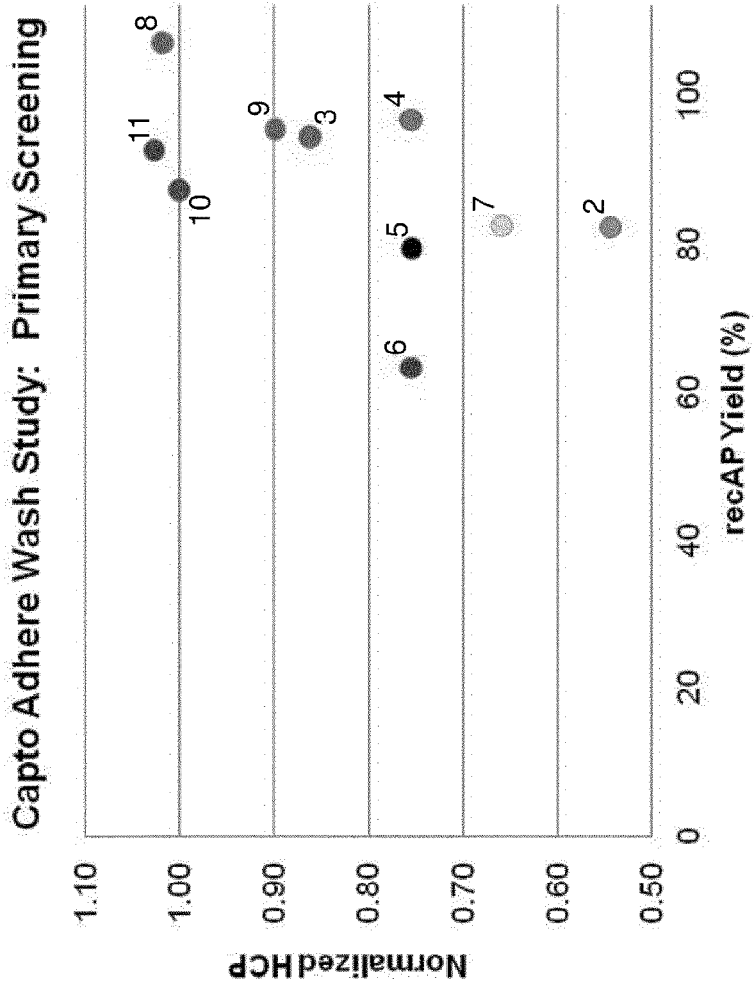

FIG. 5. Effects of Capto Adhere intermediate washes on HCP clearance and product yield for the primary screen. (A) Graphical representation of normalized HCP (normalized to baseline eluate) versus product yield for each eluate. The intermediate wash tested in each run is labeled with a colored circle corresponding to those presented in the graph. (B) Table of the residual HCP levels and yield for each completed experiment. The formulation of each intermediate wash tested as well as the results of the raw residual HCP data, normalized HCP, and product yield are listed for each run. The colored circles presented in the table correspond to the labels in (A). All buffer formulations contained 2 mM $MgCl_2$ and 50 μM $ZnCl_2$.

Figure 6A:
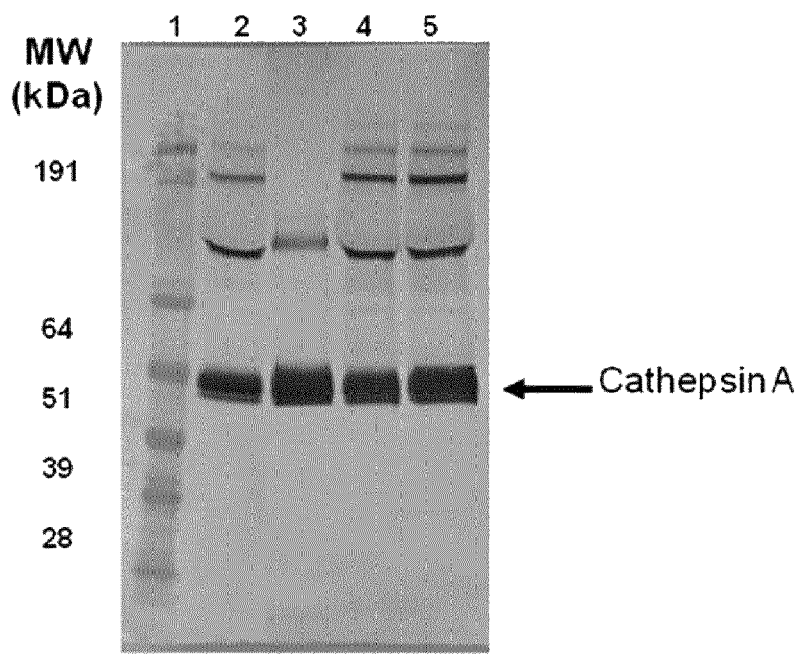

FIG. 6. Western blot analysis for the detection of catA within in-process samples. (A) A western blot was performed under non-reducing conditions using catA antibody detection for approximately 10 μg of each in-process sample. The identification, including residual HCP and yield, for each sample analyzed is listed in (B). The baseline control experiment eluate (Lane 5) contained more catA than the eluates where an intermediate wash was included (Lanes 2 & 4). Lane 3 depicts catA removed during the intermediate wash step containing 0.5M $AmSO_4$, pH 8.0. All buffer formulations contained 20 mM Tris, 2 mM $MgCl_2$ and 50 μM $ZnCl_2$.

FIG. 7. Effects of Capto Adhere intermediate washes from the secondary screen on HCP clearance and product yield. (A) Graphical representation of normalized HCP versus product yield for each eluate. The HCP values were normalized to the baseline eluate using the same load material. The intermediate wash tested in each run is labeled with a colored circle corresponding to those presented in the graph. (B) Table outlining data presented in the graph. The intermediate test wash conditions and load material for each of the experimental runs are listed. The raw HCP data, normalized HCP values, and product yield for each eluate are also listed. The colored circles presented in the table correspond to the labels in (A). All intermediate buffer formulations also contained 20 mM Tris, 2 mM $MgCl_2$ and 50 μM $ZnCl_2$.

Figures 8A, 8B:
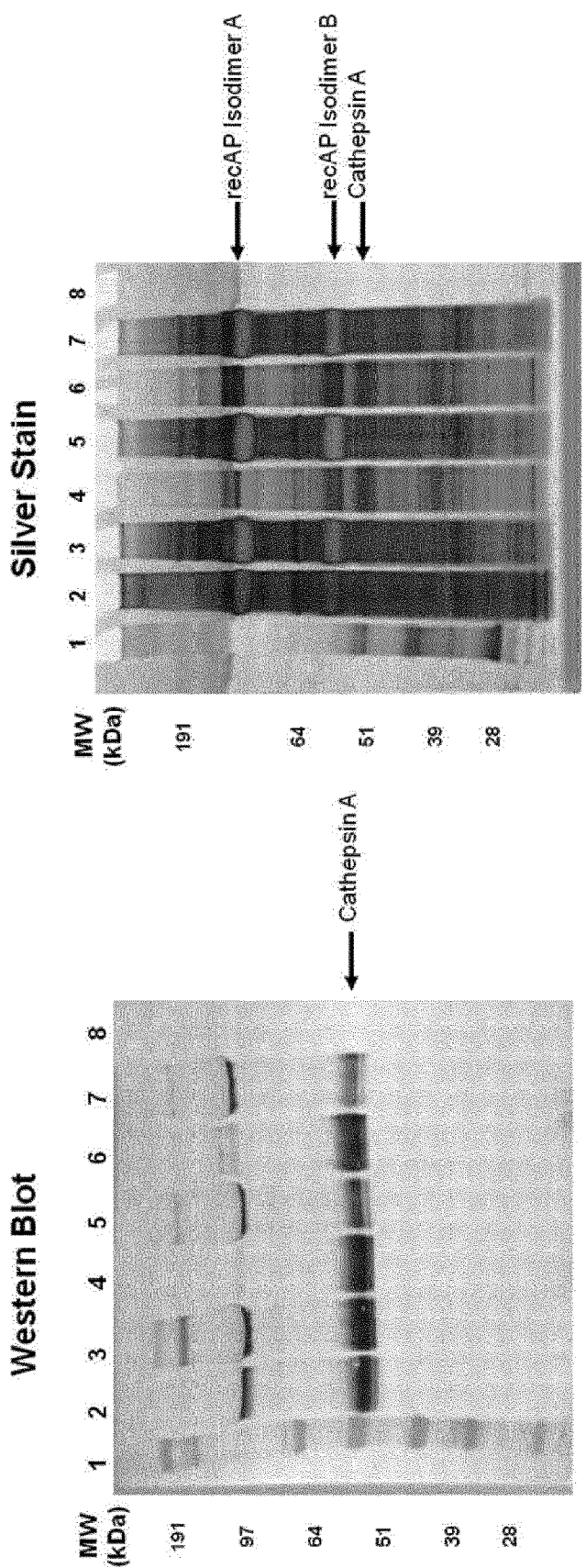

FIG. 8. Anti-catA western blot analysis comparing promising candidates from the initial and secondary screening studies. (A) Western blot with an antibody against the catA HCP. (B) Silver stain of the in-process samples. (C) Sample identification for each lane in the western blot. The amounts of product loaded per lane are indicated. The resultant HCP values for the eluates are also listed. The baseline control experiment eluate (Lane 3) contained more catA than the eluates where an intermediate wash of 0.1M NaCl, 0.2M L-Arg, pH 8.0 with (Lane 7) or without (Lane 5) 5% glycerol was included. Lanes 4 and 6 depict catA removed during the various intermediate wash steps containing 0.1M NaCl, 0.2M L-Arg, pH 8.0 in the presence (Lane 6) or absence (Lane 4) of 5% glycerol. All buffer formulations also contained 20 mM Tris, 2 mM $MgCl_2$ and 50 μM $ZnCl_2$.

Figure 9A:
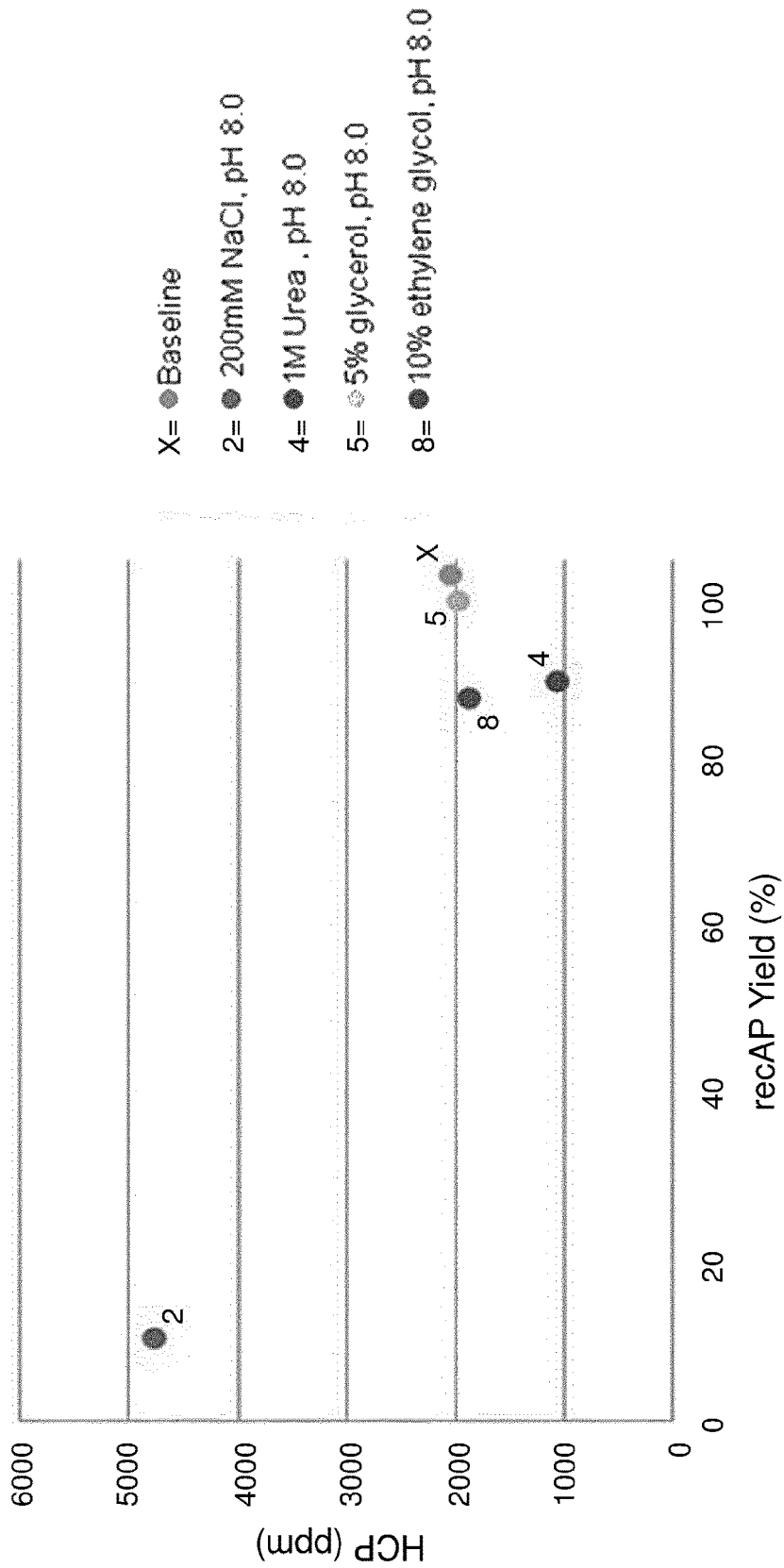

FIG. 9. Effects of MBAP intermediate washes on HCP clearance and product yield for the primary screen. (A)

Graphical representation of HCP concentration versus product yield for each eluate. (B) Table of the HCP levels and yield for each completed experiment. The formulation of each intermediate wash buffer, raw HCP data, normalized HCP, and product yield are listed for each run. The colored circles presented in the table correspond to the labels in (A). Only the 1M urea wash significantly reduced HCP while maintaining a high yield.

Figure 10A:
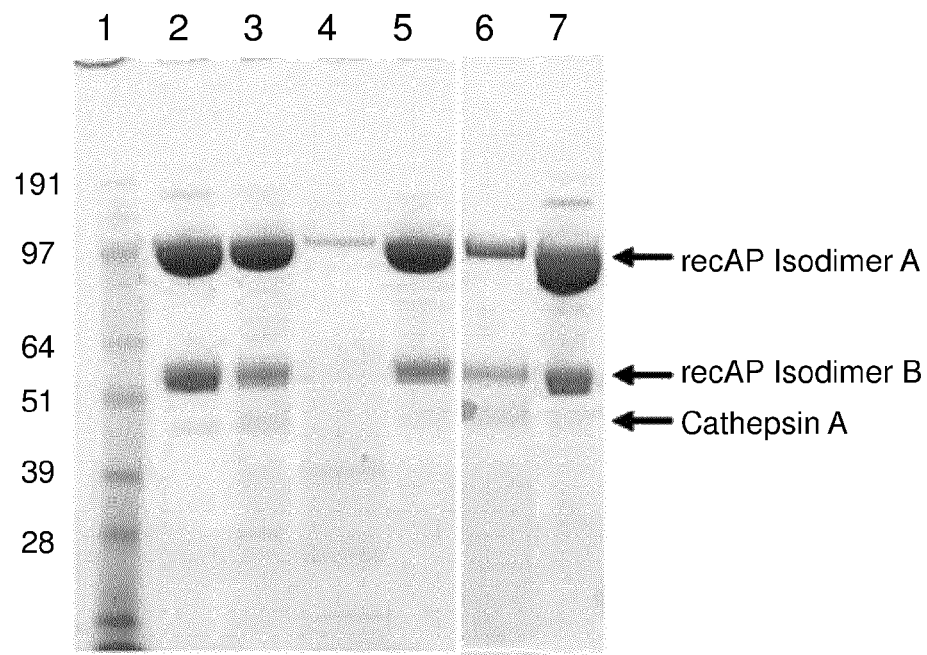

FIG. 10: SDS-PAGE and western blot analysis; MBAP Run 1 (baseline) and Run 4 (1M Urea wash) from the primary screen. (A) SDS-PAGE analysis with Gelcode Blue stain. Run 1 and Run 4 eluates displayed equivalent banding patterns. (B) Western blot with catA antibody detection. The baseline control eluate (Lane 4) contained more catA than the Run 4 eluate (Lane 6). Lane 5 depicts catA removed during the intermediate wash step containing 1M urea, pH 8.0.

Figure 11A:
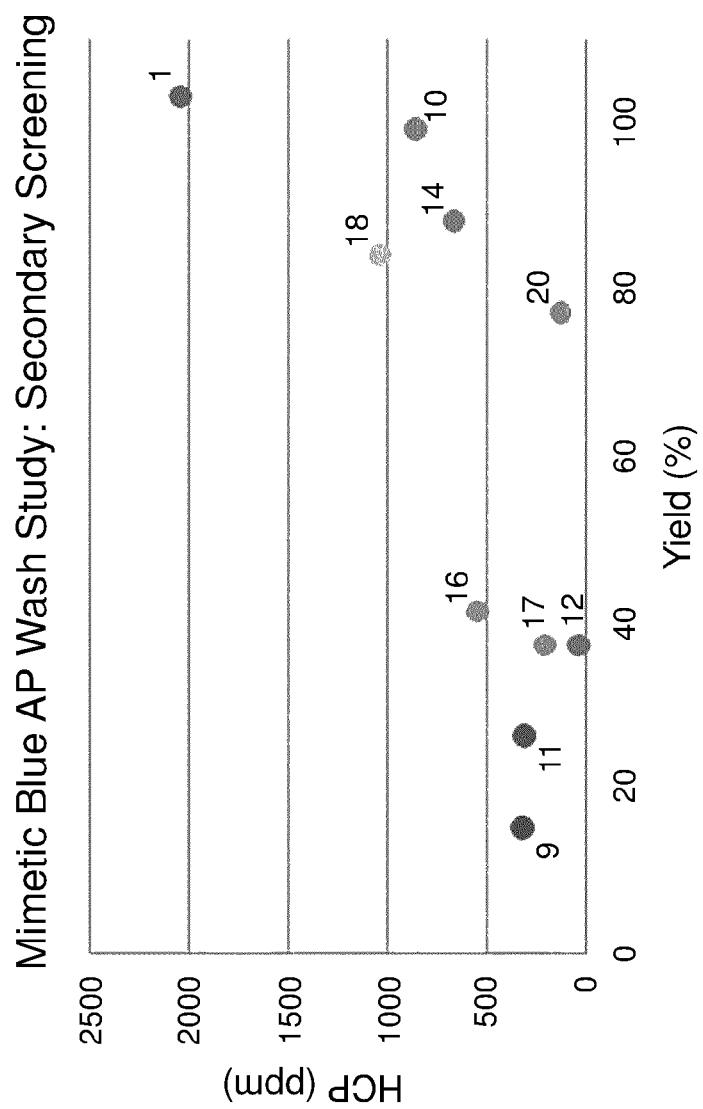

FIG. 11: Effects of MBAP intermediate washes on HCP clearance and product yield for the primary screen. (A) Graphical representation of HCP concentration versus product yield for each eluate. (B) Table of the residual HCP levels and yield for each completed experiment. The formulation of each intermediate wash tested, the eluate buffer NaCl concentration, HCP result, normalized HCP, and product yield are listed for each run. The colored circles presented in the table correspond to the labels in (A). All prepared intermediate buffer formulations contained 20 mM Tris, 2 mM $MgCl_2$ and 50 µM $ZnCl_2$.

Figure 12B:
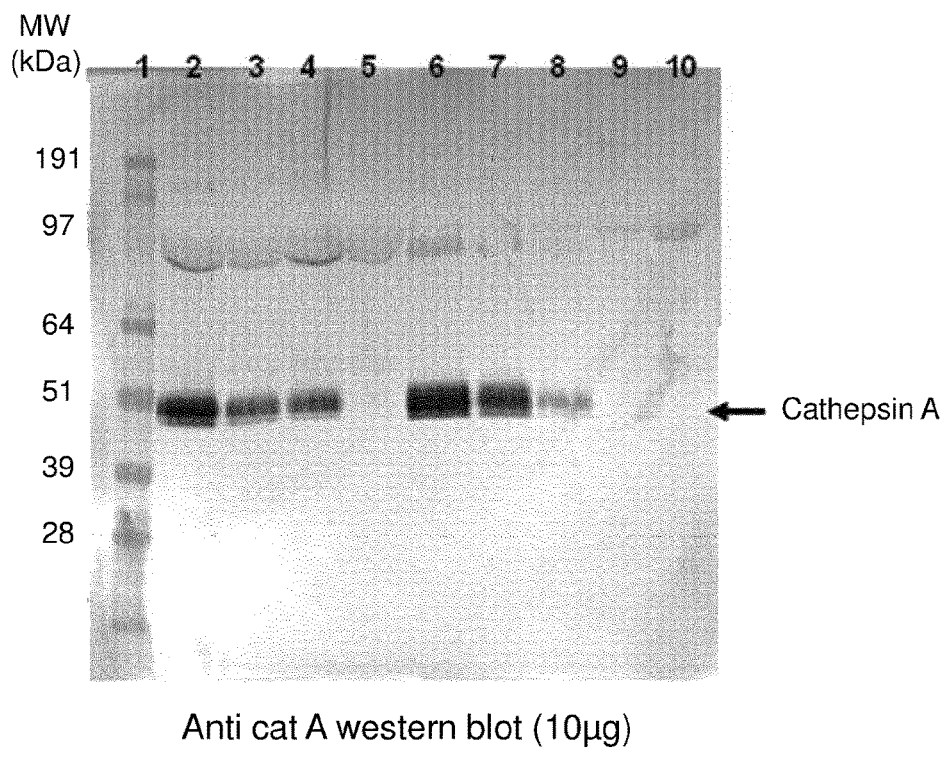
Figure 12C:
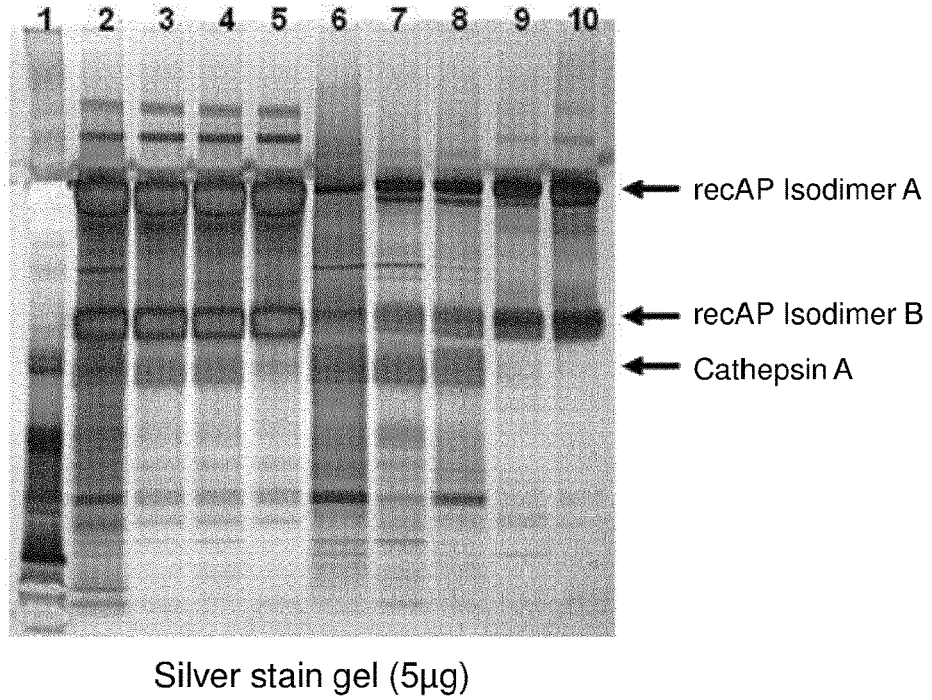

FIG. 12: SDS-PAGE and Western blot analysis of multiple HCP removal wash screening runs (A) Gel load table with sample concentration and HCP ELISA data. (B) Western blot with catA antibody detection. (C) SDS-PAGE analysis with silver stain.

Figure 13A:
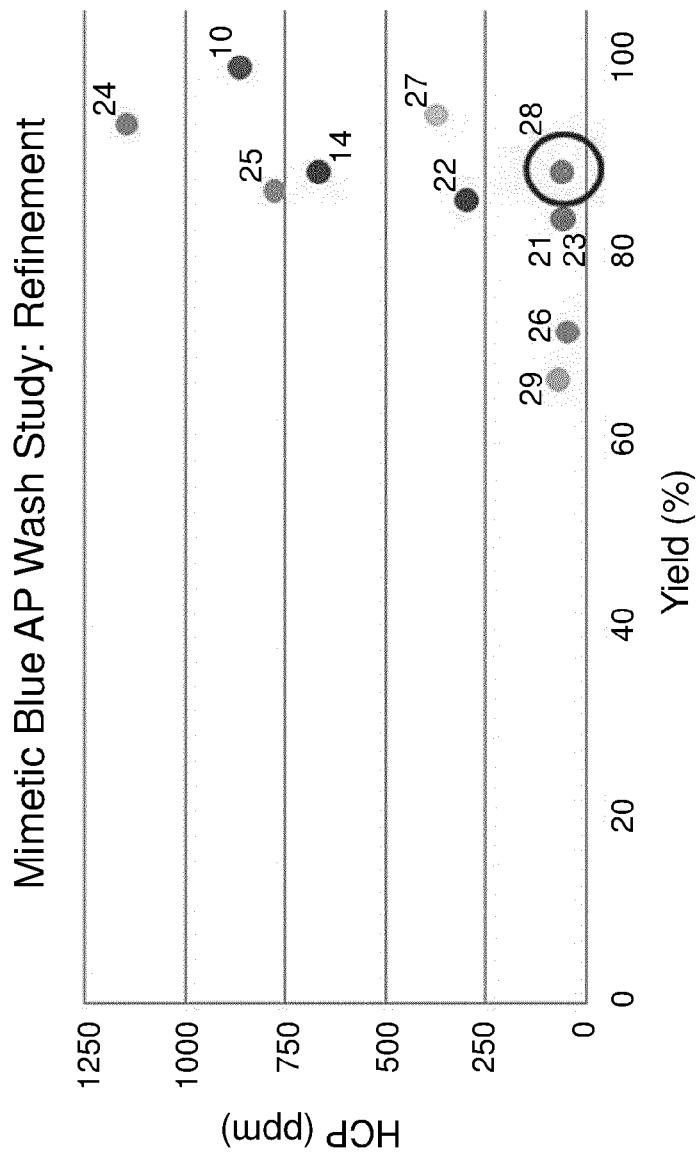

FIG. 13: Effects of MBAP intermediate washes on HCP clearance and product yield for the final wash step refinement runs. (A) Graphical representation of HCP concentration versus product yield for each eluate. The red circle highlights the run 28 result. (B) Table of the HCP levels and yield for each completed experiment. The formulation of each intermediate wash buffer is listed as well as the results of the raw HCP data, normalized HCP, and product yield for each run. The colored circles presented in the table correspond to the labels in (A). The 40 mM arginine wash buffer showed the greatest HCP clearance with high recAP recovery at load of 3 g recAP/L resin (Run 28, highlighted in yellow).

Figure 14A:
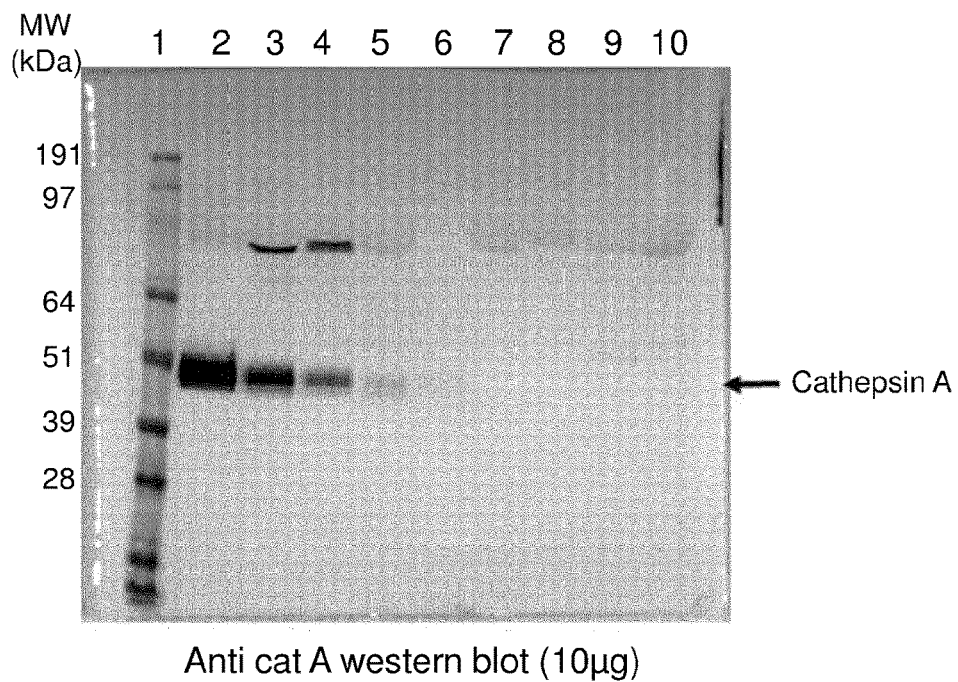
Figure 14B:
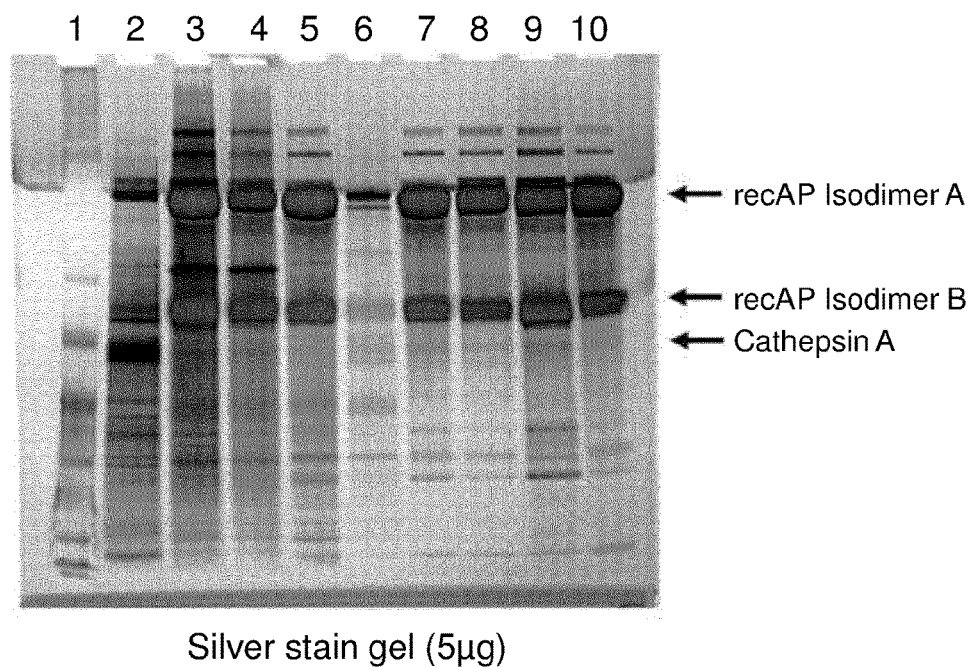

FIG. 14. Anti-catA western blot analysis of Confirmation Run process intermediates. (A) Western blot with an antibody against the catA HCP. (B) Silver Stain of the in-process samples. (C) Sample identification for each lane in the western blot. The sample loading for the western blot and silver stain are included.

FIG. 15: Analytical results of HCP reduction Confirmation Run process intermediates and BDS.

FIG. 16. Summary of the analytical testing for each downstream process intermediate for the demonstration run. Analytical results for the process intermediates from the demonstration run.

FIG. 17. Stability testing for up to 3 months of formulations obtained in Example 3 formulated in histidine buffer and citrate buffer FIG. 18. Amino acid sequence of an improved recombinant alkaline phosphatase.

EXAMPLES

Definitions Used in the Examples $AmSO_4$: Ammonium Sulfate; AP: Alkaline Phosphatase; AU: Absorbance Units; BDS: Bulk Drug Substance; BH: Bed Height; BPC: Bioprocess container; catA: Cathepsin-like protein; CCH: Cell Culture Harvest; CHO: Chinese Hamster Ovary; CV: Column Volume; ELISA: Enzyme-Linked Immunosorbent Assay; EQ: Equilibration; HCP: Host Cell Protein; HIC: Hydrophobic Interaction Chromatography; HMW: High molecular weight species; ID: Internal Diameter; L-Arg: L-Arginine; LOD: Limit of Detection; LOQ: Limit of Quantification; MBAP: Mimetic Blue Alkaline Phosphatase resin; NaSCN: Sodium Thiocyanate; PD: Process Development; PES: Polyethersulfone; ppm: Parts Per Million; PSI: Pounds per Square Inch; qPCR: Quantitative Polymerase Chain Reaction; recAP: Recombinant Alkaline Phosphatase; RP-HPLC: Reverse-Phase High Performance Liquid Chromatography; SEC-HPLC: Size Exclusion Chromatography HPLC; SDS-PAGE: Sodium Dodecyl Sulfate Polyacrylamide Gel Electrophoresis; TMP: Trans-membrane Pressure; UFDF: Ultrafiltration/diafiltration; v/v: Volume to Volume; WFI: Water for injection;

Equipment Used in the Examples

AKTA Avant; AKTA Bioprocess skid (GE Healthcare); AKTA Process; AKTA Purifier; BioPhotometer Plus UV-Vis Spectrophotometer (Eppendorf); BPG 10 cm and 14 cm diameter chromatography columns (GE Healthcare); Eppendorf Plus UV-Vis Spectrophotometer; Fisher Scientific Mini Centrifuge; Floor scale (Ohaus); Invitrogen Novex Mini Cell; Mettler Toledo Seven Multi pH and Conductivity Meter; Millipore Vantage-L Columns; Peristaltic pump (Millipore); Swinging bucket centrifuge;

Materials Used in the Examples

10 L BPC (Hyclone); 20 L BPC (Hyclone); 100 L BPC (Hyclone) Invitrogen 4-12% Bis-Tris SDS gels; 15N Planova hollow fiber filter (Asahi Kasei) 5 L BPC (Hyclone); Acetic Acid; Butyl 650M resin (Tosoh Bioscience); Capto Adhere resin (GE Healthcare); D-sorbitol; Ethanol; L-Arginine; L-Arginine Hydrochloride; L-histidine; Magnesium Chloride Hexahydrate; Mimetic Blue AP resin (Pro-Metic Biosciences, Ltd.); Pellicon 2 Ultrafiltration Biomax 10 kDa 0.1 $m^2$ (Millipore); Pellicon Biomax 10 kDa 50 $cm^2$ UF/DF cassette (Millipore); Planova 15N Viral Filter (Asahi Kasei); Poros 50 HQ resin (Applied Biosystems); Sodium Chloride; Sodium Hydroxide, 50%; Sodium Phosphate; Tris Hydrochloride; Tromethamine; Tris Base; Tris Hydrochloride; WFI (Hyclone); Zinc Chloride Example 1

Formulation Stability Studies

A number of formulation studies for recAP have been performed by KBI BioPharma, US, the CMO contracted by AM-Pharma for process development and manufacture. An initial formulation was based on that used for BIAP a form of AP that has been developed previously by AM-Pharma. BIAP was shown to be extremely stable in a Tris buffer containing a high level of glycerol (25-40%). The composition of the initial buffer was as follows:

5 mM Tris-HCl, 2 mM $MgCl_2$, 50 µm $ZnCl_2$, 25% (w/v) glycerol pH 8.

recAP is formulated in this buffer at 10 mg/mL. The maximal solubility of recAP in this buffer has not been established. However, concentrations of recAP up to 35 mg/mL have been achieved in 5 mM Tris-HCl, 2 mM $MgCl_2$, 50 µm $ZnCl_2$, pH 8.2.

Robustness Studies

A first formulation stability was conducted with a focus on pH robustness (7.5-8.5) and Tris buffer concentration 5 vs 50 mM Excipient type and concentration (glycerol 25%, 2% vs 250 mM Sorbitol)
Syringeability
Samples were analysed by pH, DSC, DLS, osmolality, viscosity.

A slight decrease in physical stability of recAP was observed by DLS with decreasing pH in 25% glycerol formulation. The Z-average diameter increased from 10 to 12 nm. Sample homogeneity decreased with pH (PdI from 0.12 to 0.33) and the peak width of the particle size distribution increased from No trends observed in 2% glycerol or 250 mM sorbitol formulations.

The pH robustness of the 5 mM formulations was considered inadequate but no significant issues were observed otherwise.

Upon these studies the formulation buffer for recAP was changed to:
50 mM Tris-HCL 2 mM $MgCl_2$, 50 μm $ZnCl_2$, 25% (w/v) glycerol pH 8
  Forced degradation studies
  Heat Stress: incubation at 50° C. for 1 week.
  Freeze/Thaw stress:
  2.5 mL mL Frozen directly in −75° C. freezer in 24 hours, then thawed at room temperature.
  2.5 mL frozen at 0.05° C./minute in a lyophilizer to −65° C., then thawed at 0.05° C./minute to 25° C.
  Exposure to 1, 3, or 5 freeze/thaw cycles
  Agitation stress: By rotary rack and orbital shaking at room temperature for 5 days.
  Deamidation/Base hydrolysis: Sample to pH≥10 with 1M Tris base, incubation at 37° C. for five days.
  Deamidation/Acid Hydrolysis: Sample to pH≤4 with 1N HCl, incubation at 37° C. for five days
  Oxidation: Exposure to 0.04% (v/v) hydrogen peroxide for 4 hours at 37° C.
  Photostability: Exposure to 8.00 klux of cool light for 150 hours followed by 10.0 watt hours/square meter of UV light for 20 hours
All samples are analysed by:
  SEC
  RP-HPLC
  Activity (kinetic)
  cIEF
  A280
  SDS-CGE
  PepMap w/LC/MS.
Accelerated Stability Studies An accelerated stability study is ongoing (see Table 1) using bulk drug substance from 10 L/5-10 gram scale production run. recAP samples are stored at −75° C., 2-8° C. and 25° C. and samples are tested monthly.

On t=2 months no effects were visible on pH and activity. Some evaporation in the 25° C. is evident from a increase in protein content and a concomitant increase in volumetric activity. The data set from the testing of the T=2 months samples is not complete yet. However, it has become clear that particulate formation continues in these samples.

TABLE 1

Stability data T = 1 months

| Method | Time Zero | 1 M, −75° C. | 1 M, 5° C. | 1 M, 25° C. |
|---|---|---|---|---|
| SEC | % HMW: 0.3% | % HMW: 0.4% | % HMW: 0.4% | % HMW: 0.9% |

TABLE 1-continued

Stability data T = 1 months

| Method | Time Zero | 1 M, −75° C. | 1 M, 5° C. | 1 M, 25° C. |
|---|---|---|---|---|
| | % Main: 99.7% | % Main: 99.6% | % Main: 99.6% | % Main: 99.1% |
| A280 | 9.87 g/L recAP | 9.67 g/L recAP | 9.83 g/L recAP | 10.46 g/L recAP |
| Appearance | Clear, colorless liquid. Free of visible particulates | Clear, colorless liquid with approximately 5-10 small white visible particulates per mL | Clear, colorless liquid with approximately 5-10 small white visible particulates per mL | Clear, colorless liquid with approximately 5-10 small white visible particulates per mL |
| pH | 8.01 | 7.88 | 7.87 | 7.83 |
| Activity (kinetic) | 4351 U/mL | 5250 U/mL | 5324 U/mL | 5508 U/mL |

Investigations into Particulate Formation and Characterization

Recently particulate formation was observed in batches of recAP that were produced at 10 gram scale. Particulates re-appear within days after 0.22 μm filtration. Visually the particulates appear proteinaceous in nature.

Size distribution analysis indicate a broad size distribution. Filtration results in a 100-fold reduction of larger particles but only a 10 fold reduction in smaller particles.

A first reformulation study has been conducted where pH (7.0-8.5), buffer type (citrate vs Tris), buffer strength (5 vs 50 mM Tris), and additives (sorbitol, sucrose, glycerol, NaCl, and Arginine) were tested (see Table 2). None of the 26 formulations prevent the formation of particulates after filtration. However there seems to be trend towards more rapid particulates formation and higher pH.

TABLE 2

Particle Evaluation Update - Visual Evaluation Completed Formulations:

| # | Buffer | Excipient | Target pH |
|---|---|---|---|
| A | 20 mM Citrate, 2 mM $MgCl_2$, 50 μM $ZnCl_2$ | 250 mM Sucrose | 7 |
| B | | 250 mM Sorbitol | |
| C | | 25% glycerol | |
| D | | 150 mM NaCl | |
| E | | 150 mM Arginine | |
| F | 50 mM Tris, 2 mM $MgCl_2$, 50 μM $ZnCl_2$ | 250 mM Sucrose | 7.5 |
| G | | 250 mM Sorbitol | |
| H | | 25% glycerol | |
| I | | 150 mM NaCl | |
| J | | 150 mM Arginine | |
| K | 5 mM Tris, 2 mM $MgCl_2$, 50 μM $ZnCl_2$ | 250 mM Sucrose | 8 |
| L | | 250 mM Sorbitol | |
| M | | 25% glycerol | |
| N | | 150 mM NaCl | |
| O | | 150 mM Arginine | |
| P | 50 mM Tris, 2 mM $MgCl_2$, 50 μM $ZnCl_2$ | 250 mM Sucrose | 8 |
| Q | | 250 mM Sorbitol | |
| R | | 25% glycerol | |
| S | | 150 mM NaCl | |
| T | | 150 mM Arginine | |
| U | 50 mM Tris, 2 mM $MgCl_2$, 50 μM $ZnCl_2$ | 250 mM Sucrose | 8.5 |
| V | | 250 mM Sorbitol | |
| W | | 25% glycerol | |
| X | | 150 mM NaCl | |
| Y | | 150 mM Arginine | |
| Z | Pooled DS, Filtered, pre- buffer exchange | | 8 |

The appearances of the formulation screening samples were assigned a ranking of 1 to 8 over the course of 7 days based on particle content (Table 3) and the results depicted in FIGS. 1 and 2.

TABLE 3

| Ranking score of visible particles | |
| --- | --- |
| ~10 particles/mL | 1 |
| 10-15 particles/mL AND/OR larger particles | 2 |
| ~15 particles/mL AND/OR mostly larger particles | 3 |
| 15-20 particles/mL, AND/OR much larger particles | 4 |
| ~20 particles/mL, AND/OR much larger particles | 5 |
| ~30 particles/mL, AND/OR much larger particles | 6 |
| 30-40 particles/mL, AND/OR much larger particles | 7 |
| 40-50 particles/mL, AND/OR much larger particles | 8 |

Example 2 recAP Formulation Development

Three formulations were evaluated to assess particle formation and stability/aggregation of recAP during freeze-thaw and heat stress. The formulations that were evaluated are listed below:

20 mM Histidine, 250 mM sorbitol, 50 µM $ZnCl_2$, 2 mM $MgCl_2$, pH 7.0 20 mM Citrate, 250 mM sorbitol, 50 µM $ZnCl_2$, 2 mM $MgCl_2$, pH 7.0

50 mM Tris, 25% glycerol, 50 µM $ZnCl_2$, 2 mM $MgCl_2$, pH 8.0

The target protein concentration for the study was 10 mg/mL. The study was performed using unfiltered and filtered (through a 0.2 µm PES membrane) Demo 4 DS, as two separate sets of samples. Protein samples were buffer-exchanged into the formulation buffers using Amicon Ultra 15, 10 k MWCO Regenerated Cellulose filters. The filters were rinsed with the appropriate buffer prior to the addition of protein. A total of 2 mL of recAP was added to each UF/DF device. A volume of 10 mL of the specified buffer was added to the sample and the total volume was reduced to ~2 mL. The process was repeated for a total of 4 cycles. The formulated samples were split into three aliquots. Aliquots of 1 mL were placed at 2-8° C. and monitored for particle formation at Time Zero, 3 days and 1 week. Two 0.5 mL aliquots were stressed—1 was placed on at 50° C. for 1 week and 1 was exposed to 5 freeze-thaw cycles. At the conclusion of the study, the 2-8° C. and stressed samples were analyzed together by SEC, RP-HPLC and activity.

Appearance Results

At all time points, all samples appeared clear and colorless.

Prior to buffer exchange, unfiltered Demo 4 DS appeared clear and colorless, with ~50 small particles per mL at Time Zero, and at the end of the study.

Prior to buffer exchange, filtered Demo 4 DS appeared clear and colorless, with no visible particles at Time Zero, and 4 small particles per mL by the end of the study.

In formulated samples, the presence of particles ranged from 1-5 small visible particles to ~20 visible particles, with a higher number of particles observed in the Tris/Glycerol formulations, from both filtered and unfiltered starting material (FIG. 3).

TABLE 4

Percentage main peak and percentage HMW of recAP protein as determined by Size Exclusion Chromatography. SEC Results

| Condition | Formulation | MP Area Percent | HMW Area Percent |
| --- | --- | --- | --- |
| Control | Citrate/Sorbitol pH 7 | 99.5 | 0.5 |
| Control | Citrate/Sorbitol pH 7, filtered | 99.6 | 0.4 |
| Control | Histidine/Sorbitol pH 7 | 99.5 | 0.5 |
| Control | Histidine/Sorbitol pH 7, filtered | 99.5 | 0.5 |
| Control | Tris/Glycerol pH 8 | 99.5 | 0.5 |
| Control | Tris/Glycerol pH 8, filtered | 99.5 | 0.5 |
| Freeze Thaw | Citrate/Sorbitol pH 7 | 99.6 | 0.4 |
| Freeze Thaw | Citrate/Sorbitol pH 7, filtered | 99.6 | 0.4 |
| Freeze Thaw | Histidine/Sorbitol pH 7 | 99.6 | 0.4 |
| Freeze Thaw | Histidine/Sorbitol pH 7, filtered | 99.6 | 0.4 |
| Freeze Thaw | Tris/Glycerol pH 8 | 99.5 | 0.5 |
| Freeze Thaw | Tris/Glycerol pH 8, filtered | 99.5 | 0.5 |
| Heat Stress | Citrate/Sorbitol pH 7 | 99.0 | 1.0 |
| Heat Stress | Citrate/Sorbitol pH 7, filtered | 99.0 | 1.0 |
| Heat Stress | Histidine/Sorbitol pH 7 | 98.8 | 1.2 |
| Heat Stress | Histidine/Sorbitol pH 7, filtered | 98.9 | 1.1 |
| Heat Stress | Tris/Glycerol pH 8 | 97.9 | 2.1 |
| Heat Stress | Tris/Glycerol pH 8, filtered | 97.9 | 2.1 |

Multiple rounds of freeze thaw do not induce HMW formation. Heat stress causes limited HMW formation in Citrate/Sorbitol and Histidine/Sorbitol based formulations. Significant HMW formation is induced by heat stress in Tris/Glycerol based formulations (Table 4 and FIG. 4).

Example 3

Intermediate Wash Screening Strategy

Two column steps were selected for the development of specific intermediate washes to provide host cell protein clearance. The washes focused on preserving product yield while significantly decreasing HCP levels in the column eluates. The intermediate washes were initially selected based on the current elution mechanism for either the mixed mode Capto Adhere resin or the affinity Mimetic Blue resin.

Upon identification of promising conditions in the primary screen, a series of washes containing specific mobile phase modulators were examined to identify wash formulations that could disrupt potential interactions between the cathepsin-like HCP and the resin ligand, interactions between the HCP and product, or both. The mobile phase modulators indicated in Table 5 were investigated singularly, sequentially and in combination.

TABLE 5

List of modulators and their potential effects on interactions between HCP and resin ligand, HCP and product, or both.

| Modulator | Modulator Effect |
| --- | --- |
| NaSCN | Decreases hydrophobic interactions |
| Urea | Weakens hydrogen bonding, chaotrope |
| Glycerol | Weakens hydrophobic interactions |
| Ethylene Glycol | Weakens hydrophobic interactions and hydrogen bonding |

TABLE 5-continued

List of modulators and their potential effects on interactions
between HCP and resin ligand, HCP and product, or both.

| Modulator | Modulator Effect |
|---|---|
| L-Arginine | Weakens hydrophobic interactions, chaotrope |
| NaCl | Decreases electrostatic interactions |

The top three wash conditions for each column step were further refined followed by testing the column steps in series to demonstrate additive effects. A bench scale run of the entire purification process was then performed to confirm that the refined process steps produced bulk drug substance that met the HCP specification without reducing the recAP specific activity or severely impacting the overall process yield. Throughout the investigations, the HCP ELISA and western blot with catA detection were routinely utilized to monitor the level of HCP clearance with the incorporation of the various intermediate washes for comparison to a baseline run.

Capto Adhere Chromatography Refinement
Primary Intermediate Wash Screen

The objective of this study was to identify an intermediate wash for the Capto Adhere column step capable of disrupting potential interactions between the product and the known HCP impurity, interactions between the HCP impurity and resin ligand or both without interfering with the product:ligand interface. Disrupting the interactions with the HCP impurity would ultimately result in enhanced product purity. Therefore, an initial screen was employed to test various intermediate washes for the Capto Adhere capture step and examine their ability to heighten HCP clearance. The intermediate washes utilized in the primary screen were selected based on the existing elution mechanisms for mixed mode chromatography which include a combination of disrupting electrostatic interactions, hydrophobic interactions or a combination of the two. The inclusion of an intermediate wash step containing a modulator (i.e. chaotropic agent, hydrophobic modifier, salt, or alkyl glycol) could reduce any existing interactions with the HCP impurity while leaving the product:ligand interaction unscathed. In addition to screening modulator effects, pH 7.0 and 8.0 were assessed.

The load material for the primary screen was clarified cell culture harvest B02-14 Oct. 2012 (i.e. 1×15 L CCH Load). This cell culture harvest incorporated the revised feeding strategy/supplementation adopted in October 2012 (1). A baseline control experiment was performed following the established process, where the column was washed with 7.5 CV of a high salt buffer (20 mM Tris, 0.25M NaCl, 2 mM $MgCl_2$, 50 µM $ZnCl_2$, pH 8.0) followed by a 3.0 CV wash with equilibration buffer (20 mM Tris, 0.1M NaCl, 2 mM $MgCl_2$, 50 µM $ZnCl_2$, pH 8.0) (2). The residual HCP levels from the control run were compared to a series of experiments incorporating intermediate wash buffers, listed in FIG. 3 for a total of 5.0 CV immediately following the 7.5 CV high salt post-load wash and prior to the 3.0 CV wash with equilibration buffer. The product for each screening experiment was eluted in upflow once the UV280 absorbance reached the start condition of ≥1.75 AU/cm followed by collection for 2.0 CV.

FIG. 5 outlines the formulations of the intermediate washes tested as well as the HCP levels and product yields. The residual HCP values presented in the graph were normalized to the baseline eluate. The product yield (determined using RP-titer) and level of HCP clearance (determined using the HCP ELISA) were the key responses analyzed throughout these screening studies. The intermediate washes which produced eluates with higher HCP clearance than the baseline were selected as promising wash candidates. Based on this strategy, the results of the primary screen revealed three likely intermediate wash candidates: (1) 0.1M NaCl, 0.2M L-Arg, pH 8.0, (2) 1M urea, pH 8.0, and (3) 0.5M $AmSO_4$, pH 8.0. All other intermediate wash formulations tested failed to reduce residual HCP levels more than 20% compared to the baseline control. The incorporation of the intermediate wash step negatively impacted product yield in several instances, including the experiment with the highest HCP clearance (FIG. 5). However, a slight sacrifice in product yield can be justified by a significant impact on HCP clearance. A secondary screen of additional buffer formulations was planned to identify an intermediate wash capable of balancing product yield and HCP clearance for this column step.

The amount of the specific residual HCP, cathepsin-like protein, was monitored by western blot under non-reducing conditions. FIG. 6 depicts the effect of incorporating two of the promising intermediate washes containing either 0.1M NaCl, 0.2M L-Arg, pH 8.0 or 0.5M $AmSO_4$, pH 8.0. Comparison of the eluate from the control experiment (Lane 5) with the eluates of the experiments including the intermediate washes (Lanes 2 & 4) confirmed the reduction of the catA impurity. Lane 3 represented the cathepsin-like protein impurity that eluted from the column during the intermediate wash with 0.5M $AmSO_4$, pH 8.0. The 0.1M NaCl, 0.2M L-Arg, pH 8.0 intermediate wash also demonstrated catA removal however the wash sample was not included in this specific western blot. Upon comparison to the baseline eluate, there was approximately 30% reduction of cathepsin-like protein for the eluate incorporating the 0.5M $AmSO_4$, pH 8.0 wash (Lane 4) and approximately 50% reduction for the eluate having received the 0.1M NaCl, 0.2M L-Arg, pH 8.0 intermediate wash (Lane 2). The results of the western blot were consistent with the HCP ELISA data presented in FIG. 5, confirming the reliability of both assays to guide the screening study.

Based on the compiled results of the product yield and HCP clearance (as was determined by western blot and HCP ELISA), the top intermediate wash candidate identified from the primary screen was the 0.1M NaCl, 0.2M L-Arg, pH 8.0.

Secondary Intermediate Wash Screen

The primary screen revealed one intermediate wash (0.1M NaCl, 0.2M L-Arg, pH 8.0) that was capable of providing at least a 50% reduction in residual HCP. The product yield was negatively impacted by this particular wash, therefore intermediate wash buffers possessing modulators that could potentially strengthen protein:ligand interactions were incorporated into a secondary screen. The most effective intermediate wash buffers from the primary screen were also tested in sequence and in combination to assess their additive effects as well as varying pH values (FIG. 7).

Using the above process conditions, a baseline control experiment was performed and the HCP levels were compared to a series of experiments incorporating the intermediate wash buffers outlined in FIG. 7. All experiments assessing the effectiveness of an intermediate wash included four wash blocks: (1) a 7.5 CV wash with high salt buffer (20 mM Tris, 0.25M NaCl, 2 mM $MgCl_2$, 50 µM $ZnCl_2$, pH 8.0), (2) a 1.5 CV wash with equilibration buffer (20 mM Tris, 0.1M NaCl, 2 mM $MgCl_2$, 50 µM $ZnCl_2$, pH 8.0), (3) a 5.0 CV intermediate wash using one of the buffer formulations listed in FIG. 7 and (4) a 3.0 CV wash with equilibration buffer (20 mM Tris, 0.1M NaCl, 2 mM $MgCl_2$, 50 µM ZnCl$_2$, pH 8.0) before product elution. For experiments possessing sequential intermediate wash steps, the column wash blocks were altered to include two 5.0 CV intermediate wash phases that were separated by a 1.5 CV wash with equilibration buffer to prevent mixing of the intermediate wash buffers. An experiment was also completed that included a low concentration of modulator in the harvest load material to identify the potential for increased product: ligand binding. The product from each screening experiment was eluted in upflow once the UV280 absorbance reached the start condition of ≥1.75 AU/cm followed by collection for 2.0 CV (2).

Figure 7A:
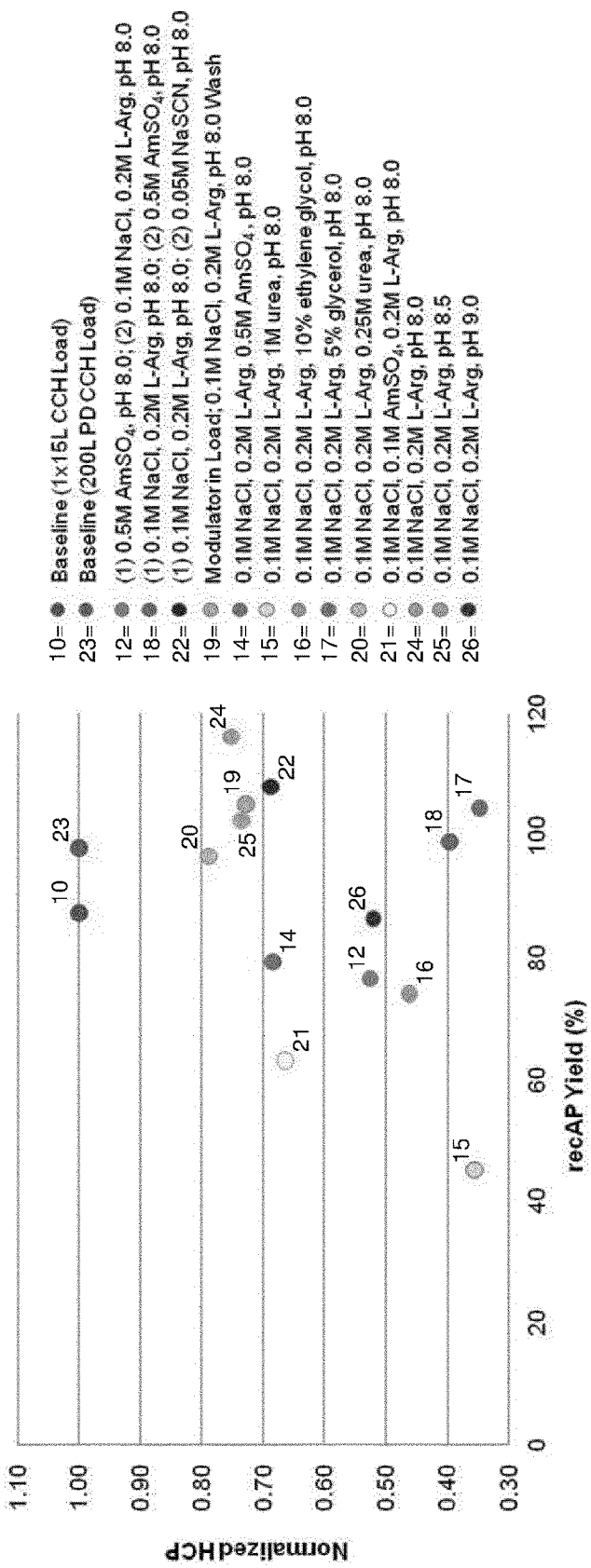

The formulations of the intermediate washes tested as well as the normalized HCP levels and yield values are presented in FIG. 7. The normalized HCP levels were included in the graph (FIG. 7A) as two different lots of harvest load material were utilized throughout the secondary screen. The residual HCP levels were normalized to the baseline control run using the same harvest load material (i.e. 1×15 L or 200 L PD CCH Load) (1). Several of the intermediate wash conditions reduced the residual HCP levels while maintaining product recovery yet the greatest result came from the intermediate wash containing 0.1M NaCl, 0.2M L-Arg, 5% glycerol, pH 8.0. The incorporation of this intermediate wash reduced the residual HCP concentration 2.9-fold when compared to the baseline control experiment. The eluate incorporating sequential washes with 0.1M NaCl, 0.2M L-Arg, pH 8.0 followed by 0.5M AMSO$_4$, pH 8.0 also exhibited significant HCP clearance up to 2.5-fold compared to the baseline eluate.

As with the primary screen, the amount of the cathepsin-like protein residual HCP was monitored by western blot under non-reducing conditions. FIG. 8 depicts the effect of incorporating the 0.1M NaCl, 0.2M L-Arg, pH 8.0 intermediate wash with and without 5% glycerol. The 0.1M NaCl, 0.2M L-Arg, pH 8.0 intermediate wash had been identified during the primary screen. Comparison of the eluate from the control experiment (Lane 3) with the eluates of the experiments including intermediate washes (Lanes 5 & 7) confirmed the reduction of the catA impurity. Lanes 4 and 6 represented the catA impurity that eluted from the column during the intermediate wash with the 0.1M NaCl, 0.2M L-Arg, pH 8.0 in the absence or presence of 5% glycerol respectively. Upon comparison to the baseline eluate, the inclusion of glycerol in the 0.1M NaCl, 0.2M L-Arg, pH 8.0 intermediate wash demonstrated slightly higher catA removal at approximately 65% compared to approximately 50% for the eluate incorporating the intermediate wash without glycerol. These results demonstrated the additive effects of combining various modulators (i.e. glycerol, salt, and arginine) into a single intermediate wash.

Selection of the Capto Adhere Intermediate Wash

Upon completion of the Capto Adhere intermediate wash screening study, the compiled analytical data, specifically the HCP ELISA and western blot results, were utilized for selection of the intermediate wash for the Capto Adhere capture step (FIG. 5, FIG. 7 and FIG. 8). Throughout the screening study, two intermediate washes clearly demonstrated significant HCP reduction compared to the baseline control run. The two intermediate washes were: (1) 0.1M NaCl, 0.2M L-Arg, pH 8.0 and (2) 0.1M NaCl, 0.2M L-Arg, 5% glycerol, pH 8.0. The western blot in FIG. 8 provided a direct comparison of the eluates from the runs incorporating these intermediate washes. Both intermediate washes provided significantly higher reduction in the specific HCP, cathepsin-like protein, compared to the baseline run, however the level of reduction was slightly higher in the eluate receiving the 0.1M NaCl, 0.2M L-Arg, 5% glycerol, pH 8.0 intermediate wash. Based on the HCP ELISA data, the eluate receiving the 0.1M NaCl, 0.2M L-Arg, 5% glycerol, pH 8.0 intermediate wash was reduced approximately 65% versus approximately 46% with the 0.1M NaCl, 0.2M L-Arg, pH 8.0 wash when compared to the baseline eluate. In addition to higher HCP clearance, the product yield was higher for the eluate receiving the 0.1M NaCl, 0.2M L-Arg, 5% glycerol, pH 8.0 intermediate wash. Given the higher HCP clearance and product yield, the intermediate wash selected for the Capto Adhere column step was 0.1M NaCl, 0.2M L-Arg, 5% glycerol, pH 8.0.

The screening study for the Capto Adhere column step was successful in identifying an intermediate wash capable of an appreciable level of HCP reduction above the baseline process. The wash selected for the removal of the cathepsin-like protein impurity during the capture step was 20 mM Tris, 0.1M NaCl, 0.2M L-Arg, 5% glycerol, 2 mM MgCl$_2$, 50 μM ZnCl$_2$, pH 8.0 and will be incorporated into the refined process containing 17.0 CV in total column wash volume. The refined Capto Adhere conditions will be integrated into a small scale process run to confirm that the optimized conditions achieve significantly reduced HCP levels in the process sequence.

Mimetic Blue AP Chromatography Refinement

Primary Intermediate Wash Screen

The objective of this study was to identify an intermediate wash for the Mimetic Blue AP column step capable of disrupting potential interactions between the product and the known HCP impurity, interactions between the HCP impurity and resin ligand or both without interfering with the product:ligand interface. Mimetic Blue AP (MBAP) is a synthetic affinity adsorbent developed specifically for the purification of alkaline phosphatase. The ligand consists of a blue chromophore linked to a functional phosphonic acid group. Binding between recAP and the ligand occurs in the absence of phosphate. Elution is achieved when phosphate is introduced into the mobile phase. The specificity of this binding mechanism suggested that a wash buffer could be formulated to disrupt recAP-HCP interaction and/or resin-HCP interaction and remove HCP in the mobile phase while maintaining recAP immobilization on the resin until elution with phosphate.

The initial wash screening experiment consisted of eight chromatography runs, each of which included a different intermediate wash step. One limitation of the method was discovered during development, namely that the presence of a high NaCl concentration (130 mM) in the feed stream and wash buffers reduced the resin capacity. This observation indicated that electrostatic attraction is also involved in the MBAP binding mechanism, suggesting that this is a pseudo-affinity resin. In order to maintain high yield, the ionic strength of the intermediate wash buffer would be limited by the electrostatic interactions occurring in this chromatography mode.

The Mimetic Blue AP column load material was generated from clarified cell culture harvest B02-14 Oct. 2012. This cell culture harvest incorporated the revised feeding strategy/supplementation adopted in October 2012 (1). The harvest was purified through the Capto Adhere capture and Poros HQ chromatography steps according to the established purification methods (2). The Capto Adhere and Poros HQ eluates were analyzed for titer, activity and residual HCP. The resultant Poros HQ eluate was assessed as representative of the process and was used as the load material for the first twelve Mimetic Blue AP runs of this investigation.

A baseline control experiment was performed according to the established MBAP purification method. Mimetic Blue AP resin lot FA0345 was packed in a 2.2 cm diameter column to a bed height of 16.2 cm, yielding a 61.6 mL column. At the time the baseline MBAP run was performed, the titer of the load (2× diluted Poros HQ eluate) was undetermined. Therefore UV280 analysis was used to approximate the concentration of the load. Using this approximate value, it was calculated that 108 mL of load provided a recAP loading density of 2 to 3 g recAP/L resin.

The column was sanitized in 0.5M NaOH and equilibrated. 108 mL of 2× diluted Poros HQ eluate was loaded onto the column. For the primary screening test runs, the post-load EQ wash step was followed by a ≥3 CV intermediate wash step utilizing the test buffers listed in FIG. 9 for each run. The run was monitored for protein elution during the wash step. After the intermediate wash, the column was again washed with EQ buffer to remove the test wash buffer components. The product was eluted with 20 mM Tris, 25 mM phosphate, 130 mM NaCl, 2 mM $MgCl_2$, 50 µM $ZnCl_2$, pH 8.0. Eluate collection was by UV gate as the peak rose to 25 mAU, until it descended to 50 mAU. The column was stripped and sanitized between runs. The eluates were analyzed for titer (RP-HPLC), activity and residual HCP (HCP ELISA and Western Blot). Any wash condition that reduced the residual HCP concentration in the eluate without significantly impacting yield would be carried forward to the secondary screening phase of this study.

Figure 10B:
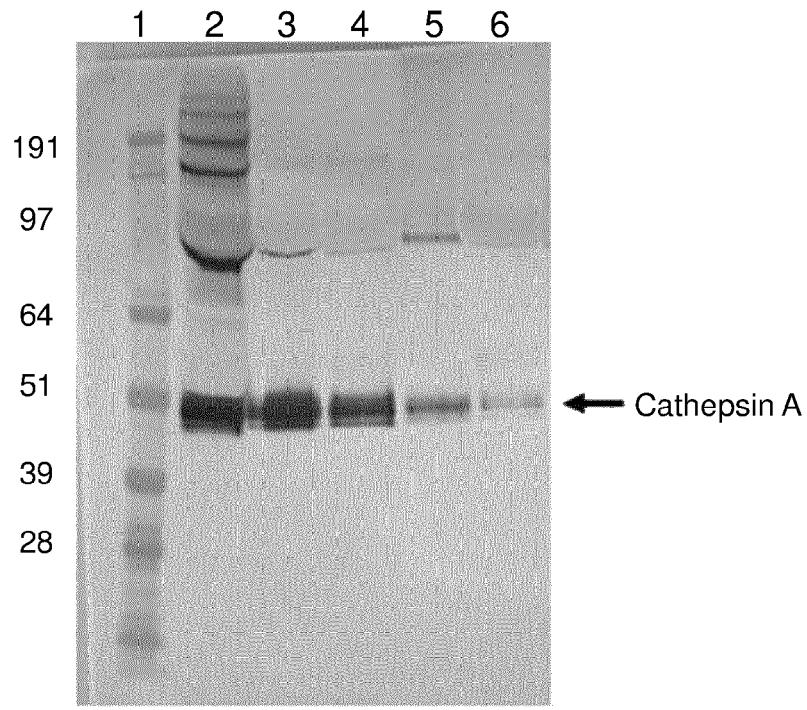

The results of the primary screening runs are presented in FIG. 9 and FIG. 10. The baseline run conditions achieved 100% yield of recAP, and the residual HCP concentration was 2047 ppm. Four intermediate wash conditions (100 mM NaCl, 200 mM NaCl, 0.2M NaSCN and 200 mM arginine) caused considerable product loss during the wash step. The 5% glycerol and 10% ethylene glycol washes did not adversely affect yield but also did not show significant HCP clearance as compared to the baseline run. The only condition which met the criteria of high yield (90%) and significant HCP reduction (1066 ppm) was the 1M urea wash step (Run 4). The western blot with cathepsin-like protein detection (FIG. 10B) demonstrated that the eluate from Run 4 showed a reduced catA band compared to the baseline run. The blot also detected catA in the 1M urea wash, indicating that the wash was effective in disrupting the association between recAP and this HCP species, and/or resin and HCP. This result confirmed the findings of the HCP ELISA analysis.

Secondary Intermediate Wash Screen

The secondary screening study introduced new wash conditions in an attempt to improve upon the HCP clearance seen in the primary screening runs. Sodium chloride and L-arginine were again tested but at lower concentrations than in the primary screening runs. Arginine had shown selective HCP removal in the Capto Adhere primary screening runs, so we wanted to further investigate the use of arginine in this mode of chromatography. The chaotrope urea demonstrated moderate HCP clearance in the MBAP primary screening runs, so urea was tested in combination and in series with sodium chloride. 10% ethylene glycol had also shown a small reduction in HCP, so it also was tested in combination with NaCl to attempt to increase the separation between HCP and recAP or HCP and column matrix. Finally, the wash buffers were tested at both pH 7.0 and 8.0 to detect pH dependent interactions.

In addition to testing the effect of intermediate wash steps on HCP clearance, we tested the effect of eliminating NaCl in the elution buffer. In the primary screening experiment, we observed that 100 mM NaCl caused approximately 60% product breakthrough during the intermediate wash, and 200 mM NaCl had caused complete product breakthrough, without the presence of phosphate. It was theorized that at high ionic strength, electrostatic mechanisms dominated the binding kinetics and caused the ligand to release proteins into the mobile phase. The selectivity of the resin could be enhanced by elution with a low phosphate concentration and no NaCl, favoring only the dissociation of recAP and the ligand's phosphonate group, and leaving HCPs electrostatically bound on the resin until the 1M NaCl+0.5 M phosphate strip.

A new lot of load material was prepared after the twelfth MBAP test run. Concurrent investigation of the Capto Adhere purification method had indicated that a 0.1M NaCl, 0.2M L-arginine, pH 8.0 intermediate wash step reduced HCP in the Capto eluate by 50%. Therefore, the new lot of load material for the MBAP secondary screening runs was prepared with the inclusion of the 0.1M NaCl, 0.2M L-Arg, pH 8.0 intermediate wash step in the Capto Adhere purification step. The Poros HQ 50 purification method remained unchanged.

A summary of the results of the secondary screening runs is presented in FIG. 11. In Run 10, the only deviation from the baseline method was the exclusion of NaCl in the elution buffer; load material and post-load wash with EQ buffer were equivalent. This change in elution buffer formulation alone reduced the HCP concentration of the MBAP eluate by approximately 40% in comparison to the baseline run. Therefore, the remainder of the runs used elution buffer without NaCl. Runs 14 through 20 were performed with a new lot of MBAP load that was produced from a Capto Adhere eluate that incorporated an intermediate HCP removal wash containing 0.1M NaCl, 0.2M L-arginine, pH 8.0. Run 14 showed that the HCP reduction achieved in the Capto step combined with the removal of NaCl in the MBAP elution buffer reduced the HCP level of the MBAP eluate to 667 ppm, without the inclusion of a wash buffer containing modulators in the MBAP purification method. A number of runs reduced the HCP concentration to less than 500 ppm, but did not generate an acceptable product yield. The wash combination of 10% ethylene glycol and NaCl, pH 8.0 was the only intermediate wash formulation which enhanced HCP clearance (128 ppm) without severely affecting yield (77%). Although this wash was effective for HCP clearance, the inclusion of NaCl in the intermediate wash buffer was considered an unacceptable risk, since many of the runs using NaCl in the wash buffers had shown large recAP product losses.

Western blot analysis of Run 10 fractions, which utilized MBAP elution buffer formulation without NaCl, led to the conclusion that the reduction in eluate HCP concentration was likely due to HCP remaining bound to the resin during the elution step with phosphate (no NaCl), whereas the previous elution buffer containing 130 mM NaCl co-eluted HCP with the recAP. The HCP ELISA results showed that the residual HCP concentration of the Run 10 strip is elevated as compared to the eluate (FIG. 12A). The ELISA results were confirmed by the Western blot (FIG. 12B). A catA band at approximately 50 kDa was seen in the load (Lane 2), Run 1 eluate (Lane 3) and Run 10 strip (Lane 6). The catA band is absent in the Run 10 eluate (Lane 5), indicating that the catA HCP has been reduced below the limit of detection (estimated as <1000 ppm) of the assay in this sample. The same band was more pronounced in the Run 10 strip peak sample.

Run 12, which incorporated 20, 40, 60 and 80 mM L-arginine wash steps, showed the greatest reduction in HCP. The eluate HCP concentration was <40 ppm but the yield was poor at 37%. In this run, the arginine steps were collected separately to determine the arginine concentration at which recAP dissociated from the resin. Analyses on the wash fractions by western blot (FIG. 12B) showed that the catA HCP impurity was present in all of the arginine washes, while significant loss of product did not occur until the 60 and 80 mM arginine steps. This discovery indicated that a 40 mM arginine wash step may be capable of selectively removing a significant amount of HCP from the recAP and/or resin without interfering with the recAP:ligand binding interaction. A 40 mM arginine wash was chosen for further investigation in the third round of MBAP intermediate wash screening experiments.

MBAP Intermediate Wash Step Refinement

Three intermediate wash modulators were chosen from the previous experiments for further refinement. In the primary wash screening study, 1M urea had demonstrated HCP reduction in the eluate without affecting product recovery. In the secondary screening study, ethylene glycol+NaCl had reduced HCP without causing severe product loss. Arginine had shown selective HCP removal, but concentrations above 40 mM adversely affected yield. The next phase of the study expanded on the investigation of these modulators. The use of elution buffer without NaCl was carried forward as well. The final runs tested the top three candidates at 3 g recAP/L resin column loading to test for reduction in column capacity due to the modulator wash.

The specific test wash buffer formulations and summary of the results of the refinement runs are presented in FIG. 13. The 1M urea wash had not been previously tested in combination with the phosphate only elution buffer. Runs 21 and 22 utilized wash buffers with 1M and 2M urea respectively, and were eluted with the new phosphate-only buffer. Run 27 was performed with a 1M urea wash also, but the amount of recAP loaded onto the column was increased to the target load density of 3 g recAP/L resin. Run 21 showed that column loading at 1.8 g recAP/L resin combined with the 1M urea wash buffer produced an eluate with 59 ppm HCP and 83% recAP recovery. Increasing either the urea concentration in the wash buffer or the recAP load density led to a higher residual HCP concentration in the product eluate (299 and 371 ppm HCP respectively).

Intermediate wash buffers that combined 1M urea with either 10% ethylene glycol or 40 mM arginine were also assessed for HCP clearance and product yield. The 10% ethylene glycol/1M urea combination wash generated product with a high residual HCP concentration (777 ppm). The 40 mM arginine/1M urea wash combination was performed at column loadings of 2.3 and 3.0 g recAP/L resin. At the lower product load, the arginine/urea wash produced an eluate with low residual HCP concentration, 46 ppm. The resultant recAP product yield of 71% was below the desired recovery. When the same purification was performed at the higher recAP load density, the HCP clearance was still acceptable (68 ppm) but the recovery was further decreased to 66%.

Runs 23 and 29 were performed using 40 mM arginine, pH 8.0 in the wash step. The column was loaded at both 1.8 and 3 g recAP/L resin for Runs 23 and 29 respectively. Both runs produced eluates with a low residual HCP concentration (54 and 59 ppm) and achieved acceptable yields (83 and 88%). This intermediate wash was the only candidate that maintained HCP clearance capability and high product yield at the maximum column load capacity.

The screening study for the Mimetic Blue AP column step identified two process changes that led to the reduction of the residual HCP concentration in the product pool to approximately 60 ppm. The first process improvement was the addition of an intermediate wash step to the chromatography method for selective clearance of HCP. The wash selected for the removal of the cathepsin-like protein impurity was 20 mM Tris, 40 mM L-Arg, 2 mM $MgCl_2$, 50 μM $ZnCl_2$, pH 8.0. The inclusion of 3.0 CV of this selected intermediate wash buffer will add 20 to 30 minutes to the MBAP process time. The second process improvement was the removal of NaCl from the elution buffer. The combination of these process revisions resulted in greater than 30-fold reduction in residual HCP as measured by HCP ELISA. The refined MBAP conditions were integrated into a small scale process run to confirm these findings.

Process Confirmation Run

After the HCP reduction experiments were concluded, a small scale confirmation run was completed incorporating the revised process conditions. Cell culture harvest (200 L PD 16 Oct. 2012) was processed through all unit operations with the exception of the viral filtration. Final product analysis was performed on filtered UF/DF retentate. One cycle of each chromatography step was performed. Process intermediates were analyzed by RP-HPLC (for titer and % isodimer A), ELISA (activity and HCP), and SDS-PAGE and western blot. A summary of analytical results can be seen in FIG. 15. The new process recovered 53 mg of purified recAP with an overall process yield of 34%.

Capto Adhere Capture Chromatography

The Capto Adhere Run #32 of the HCP reduction experiments was performed using 0.1M NaCl, 0.2M L-Arg, 5% glycerol, pH 8.0 intermediate wash (See Section VI.C). This wash formulation was shown to give the highest HCP clearance, and was chosen for inclusion in the Capto Adhere method. Therefore, the eluate from Run #32 was purified through the remainder of the purification process.

A total of 297 mL of the 200 L PD 16 Oct. 2012 cell culture harvest was processed in the Capto Adhere Run #32. The titer of the harvest was 0.63 g/L recAP by RP-HPLC. The actual loading factor was 7.8 g recAP/L resin. During elution, 187 mg of product was collected. The chromatogram showed a different elution peak profile than had been seen before the new wash step was instituted. In this run, the UV280 elution peak was split, whereas in previous runs the eluate came off in a single peak (2). The reason for this change in peak shape is undetermined but is most likely due to the additional arginine wash step. Although the chromatogram looked different, the overall recAP yield (93%) and activity yield (86%) were equivalent to the previous demo runs. The eluate was filtered through a 0.2 μm PES filter and stored at 2-8° C.

Viral Inactivation & Poros 50 HQ Purification

The Capto Adhere eluate was equilibrated to room temperature. To achieve a concentration of 1.0% Triton X-100, 4.65 mL of 10% Triton X-100 (in WFI) was added to the 41.9 mL of Capto Adhere eluate. The eluate was thoroughly mixed and then incubated static for 60 minutes for complete viral inactivation. After incubation, the material was diluted 12× with 514 mL of WFI. The conductivity target was ≤4.5 mS/cm; the final conductivity of the solution was 4.13 mS/cm and the pH was 7.74.

The Poros HQ 50 resin was packed in a 1.1 cm column to a bed height of 19.6 cm for a final column volume of 18.6 mL. The column asymmetry was 1.16 and the plate height was 0.025 cm. The actual loading factor of this run was 9.1 g recAP/L resin. The chromatography method was unchanged from the Demo Run 5 operating parameters (2). 56 mL of eluate was collected. Analysis showed 61% recAP mass yield and 66% recovery in activity. The eluate was filtered through a 0.2 μm PES filter and stored at 2-8° C. The Poros HQ 50 chromatography performed as expected.

Mimetic Blue AP Purification

The Mimetic Blue AP chromatography step incorporated two method improvements. A 3.0 CV intermediate wash buffer containing 40 mM arginine was added. Also, the elution buffer was altered by eliminating the NaCl in the buffer. Both revisions were implemented to reduce HCP in the process intermediate.

The Mimetic Blue AP (MBAP) resin was packed in a 2.2 cm column to a bed height of 16.0 cm for a final column volume of 60.8 mL. The column was not tested for HETP and asymmetry. The packed column was sanitized in 0.5M NaOH and equilibrated with 20 mM Tris, 2 mM $MgCl_2$, 50 μM $ZnCl_2$, pH 8.0. The actual loading factor of this run was 1.6 g recAP/L resin. The Poros eluate was diluted 1:1 with WFI to reduce the conductivity for binding. The eluate volume was 41 mL. Analysis showed 84% recAP mass yield and 80% recovery in activity, which was slightly below the recoveries seen in Demo Run 5 (2). The HCP concentration of the MBAP eluate was 34 ppm, which was a 2500-fold reduction from the load material. The eluate was filtered through a 0.2 μm PES filter and stored at 2-8° C.

Butyl 650M Purification

The next step in the process included a polishing step using hydrophobic interaction chromatography. The Butyl 650M resin was packed in a 1.1 cm column to a bed height of 8.7 cm for a final column volume of 8.3 mL. The target bed height for the Butyl purification step is 19.5 cm, but the height was reduced in this run in order to load the resin near capacity. The column asymmetry was 1.17 and the plate height was 0.034 cm. The MBAP eluate after sampling was 37.8 mL. The MBAP eluate was adjusted to 1.0M $AmSO_4$ with the addition of 31.9 g of 2.1M $AmSO_4$. The conductivity of the load was 135 mS/cm and the pH was 7.67. The actual load factor in this run was 9.2 g recAP/L resin. The chromatography method was unchanged from the Demo Run 5 operating parameters (2). An eluate volume of 48 mL was collected. For prevention of precipitate formation, the eluate was immediately diluted with 96 mL WFI to lower the $AmSO_4$ concentration to a final diluted volume of 144.5 mL. Analysis showed 86% recAP mass yield and 81% recovery in activity. The eluate was filtered through a 0.2 μm PES filter and stored at 2-8° C. The Butyl 650M chromatography performed as expected.

Ultrafiltration/Diafiltration

A 50 cm2 Pellicon (Millipore) Biomax 10 kDa PES ultrafiltration cassette was used for the UF/DF step, providing a mass to area ratio of 13 g/m2. The cassette was rinsed with WFI then equilibrated with formulation buffer (20 mM histidine, 250 mM D-sorbitol, 2 mM $MgCl_2$, 50 μM $ZnCl_2$, pH 7.0). The 145 mL of diluted Butyl eluate was concentrated approximately 3-fold to 40 mL. Due to the small volume of the product, the retentate was not further concentrated. During the concentration, the TMP across the membrane was maintained at ≤15 psi. After concentration, the product was diafiltered 10× with formulation buffer. The material was collected and filtered through a 0.2 μM PES bottle top filter. After product recovery, 30 mL of formulation buffer was recirculated through the cassette to recover product from the membrane surface. The buffer flush was not added to the retentate but was stored separately. This was done to prevent dilution of the UF/DF retentate. The UF/DF step yield was 67% recAP mass yield in the retentate and 15% in the buffer flush, which equals 82% total recAP recovery. The HCP concentration was below the LOQ of 2 ppm. The product was stored at 2-8° C.

Summary of HCP Reduction Confirmation Run

The purpose of this purification run was to perform the entire purification process from the capture step to UF/DF and final formulation, incorporating process changes made to the Capto Adhere and Mimetic Blue AP chromatography steps. We sought to prove that these changes could reduce the HCP concentration in the BDS to well below the target specification of ≤100 ppm without adversely affecting the activity of the recAP molecule or the overall process yield. The western blot analysis of the process intermediates showed that catA was undetectable after the Mimetic Blue intermediate wash step (FIG. 14). The residual HCP concentration in the BDS produced in this run as determined by HCP ELISA was <2 ppm (below LOQ). The specific activity at 543 U/mg was within specification, and the overall yield was 34%. Product recovery in the UF/DF step was lower than in the Demo runs 4 and 5, but low retentate volume in UF/DF is known to cause poor product recovery. Other than the UF/DF step, step yields were equivalent to Demo runs 4 and 5, demonstrating that the Capto Adhere and MBAP process changes did not significantly reduce the overall yield of the process.

Example 4

Purification Process

The purification process for recAP includes six unit operations. The Capto Adhere chromatography capture step is followed by viral inactivation of the eluate with 1% Triton X-100. Anion exchange chromatography with Poros HQ 50 removes the detergent and partially purifies the feed stream. Two additional chromatography steps (Mimetic Blue AP and Butyl 650M) are performed to reduce impurities (i.e. host cell protein, DNA) to specification. The material is concentrated and buffer exchanged into formulation buffer using a 10 kDa MWCO PES membrane. Finally, the purified recAP is viral filtered using a 15N Planova hollow fiber filter.

Capto Adhere Capture Chromatography

The purpose of the capture step is to separate the target molecule from the cell culture media, to concentrate the product and to partially purify recAP. The mixed mode resin Capto Adhere was chosen as the capture step in the purification process. The capacity of the Capto Adhere column had previously been determined as 8 g recAP/L resin (3).

Clarified cell culture harvests 14 Oct. 2012 B01 and B03 were combined to provide approximately 20 L of harvest for downstream purification. Capto Adhere resin was packed in a sanitized BPG 100 column (GE Healthcare) to a bed height of 23.7 cm for a final column volume of 1.9 L. The column asymmetry was 1.44 and the plate height was 0.049 cm. The packed column was sanitized in 0.5M NaOH and equilibrated. The titer of the combined harvest was 0.7 g/L recAP by RP-HPLC, so all 20 L of harvest was processed. The actual loading factor was 7.3 g/L resin. After loading the harvest on the column, a NaCl salt wash step was performed, followed by EQ buffer wash to reduce the NaCl concentration. Elution was achieved with 0.55M L-arginine+0.1M NaCl. During the elution phase of the method, the flow direction was reversed in order to minimize the eluate volume. The eluate peak collection was initiated when the UV280 rose to 1.75 AU/cm. Two CV of eluate were collected through a 0.2 μM PES filter into a sterile 50 L BPC; the eluate volume was 3.9 L. The conductivity was 38.2 mS/cm and the pH was 7.79. The large volume BPC was chosen to allow for the 13× water dilution that is performed in the next chromatography step. The run performed equivalently to previous demo runs.

Viral Inactivation & Poros 50 HQ Purification

The Capto Adhere eluate was equilibrated to room temperature. 533 mL of 10% Triton X-100 (in WFI) was added to the eluate resulting in a final concentration of 1.2%. (The target of 1.0% concentration was exceeded due to a weight measurement error.) The eluate was thoroughly mixed and then incubated static for 60 minutes. After incubation, the material was diluted 13× with 63.9 L of WFI. The conductivity target was ≤4.5 mS/cm; the final conductivity of the solution was 3.21 mS/cm and the pH was 7.72.

Poros HQ 50 resin was packed in a sanitized BPG 100 column (GE Healthcare) to a bed height of 20.0 cm for a final column volume of 1.6 L. The column asymmetry was 1.63 and the plate height was 0.020 cm. The purification parameters for the Poros HQ 50 step are listed in 10 below. The packed column was sanitized in 0.5M NaOH and equilibrated. The capacity of the Poros HQ 50 column had previously been determined as 10 g recAP/L resin (3). The actual loading factor of this run was 8.0 g recAP/L resin. After loading the column, a 50 mM NaCl salt wash step was performed to remove impurities. Elution was performed in down flow with 130 mM NaCl. The eluate peak collection was initiated when the UV280 rose to 0.5 AU/cm. Three CV of eluate were collected through a 0.2 µM PES filter into a sterile 10 L BPC; the volume was 4.7 L. The conductivity of the eluate was 14.6 mS/cm and the pH was 8.22.

The run performed equivalently to previous demo runs except that the recAP yield (61%) was lower than in Demo run 4 (85%). The reason for the reduced yield is unknown. The conductivity of the elution buffer was checked to determine if incorrect buffer formulation was the cause of the lower yield. The buffer was at 14 mS/cm, which is the target conductivity for the buffer, so low NaCl concentration was eliminated as the cause. The conductivity of the wash buffer also was well within specification, which suggests that the low yield was not due to product loss in the wash buffer. Poros HQ 50 eluate was analyzed by RP-HPLC (titer and % isodimer A), SEC-HPLC (purity) and ELISA (activity and HCP) assays. Analysis showed 61% recAP mass yield and 60% recovery in activity. Comparing the Poros eluate to the load material, the percent isodimer A increased from 82% to 93% and the purity by SEC increased from 36% to 87%. HCP was reduced three-fold. The eluate was stored at 2-8° C.

Mimetic Blue AP Purification

Mimetic Blue AP (MBAP) resin was packed in a sanitized Quickscale 14 cm diameter column (Millipore) to a bed height of 17.0 cm for a final column volume of 2.6 L. The column asymmetry was 1.37 and the plate height was 0.039 cm. The packed column was sanitized in 0.5M NaOH and equilibrated. The capacity of the MBAP column had previously been determined as 3 g recAP/L resin (3). The actual loading factor of this run was 2.9 g recAP/L resin. The Poros eluate was diluted 1:1 with WFI to reduce the conductivity. After loading the diluted Poros eluate onto the column, unbound material was removed with an EQ buffer wash. Elution was performed in down flow with 25 mM NaPO$_4$, 130 mM NaCl. The eluate was collected when UV280 rose above 0.125 AU/cm until it fell to 0.25 AU/cm on the tail end of the peak. The eluate was collected through a 0.2 µM PES filter into a sterile 10 L BPC; the volume was 2.4 L, or 0.9 CV.

The run performed equivalently to previous demo runs. The eluate was analyzed by UV280 (titer), RP-HPLC (% isodimer A), SEC-HPLC (purity) and ELISA (activity and HCP). Analysis showed 92% recAP mass yield and 96% recovery in activity. The product purity by SEC increased from 87% to 99.6%. HCP was reduced approximately 50-fold. The eluate was stored at 2-8° C.

Butyl 650M Purification

Butyl 650M resin was packed in a sanitized BPG 100 column (GE Healthcare) to a bed height of 19.0 cm for a final column volume of 1.5 L. The column asymmetry was 1.37 and the plate height was 0.039 cm. The packed column was sanitized in 0.5M NaOH and equilibrated with 1.0M AmSO$_4$. The 2.4 L MBAP eluate was adjusted to 1.0M AmSO$_4$ with the addition of 2.2 L of 2.1M AmSO$_4$. The conductivity of the load was 125.7 mS/cm and the pH was 7.77. The capacity of the Butyl 650M column had previously been set as 10 g recAP/L resin (4), although the true capacity of the column under the current processing conditions has not been rigorously studied. The actual load in this run was 4.6 g recAP/L resin, approximately half of the target load factor. After loading the column, unbound material was removed with an EQ buffer wash. Elution was achieved with 0.6M AmSO$_4$. The eluate peak was collected between 0.25 AU/cm until the UV fell to 0.25 AU/cm on the peak tail. The eluate was collected through a 0.2 µM PES filter into a into a 20 L BPC; the volume was 4.4 L. For prevention of precipitate formation, the eluate was immediately diluted with 8.8 L WFI to lower the AmSO$_4$ concentration. The run performed equivalently to previous demo runs.

Ultrafiltration/Diafiltration

In Demo Run 5, a new formulation buffer was used in order to enhance solubility of matter prone to particulation. The new formulation was 20 mM histidine, 250 mM D-sorbitol, 2 mM MgCl$_2$, 50 µM ZnCl$_2$, pH 7.0. The post-VF addition of 25% glycerol was eliminated from the process, so the UF/DF final concentration target was changed from ≥13.5 g/L to ≥11.5 g/L.

For Demo Run 5, a 0.1 m2 Pellicon XL (Millipore) Biomax 10 kDa PES ultrafiltration cassette was used, providing a mass to area ratio of 57 g/m2. The cassette was rinsed with WFI then equilibrated with formulation buffer. The diluted HIC eluate was concentrated to 15 g/L. During the concentration the TMP across the membrane was maintained at 8-15 psi. After concentration, the product was diafiltered 10× with formulation buffer. The material was collected into a 1 L PETG bottle. After product recovery, 100 mL of formulation buffer was recirculated through the cassette to recover product from the membrane surface. The buffer flush was added to the retentate and the solution was filtered through a 0.2 µM PES bottle top filter. The final volume was 460 mL. The product was analyzed by UV280 (titer), RP-HPLC (% isodimer A), SEC-HPLC (purity) and ELISA (activity and HCP). The analytical results are shown in Table 6: Analytical results of the Demo run 5 UF/DF. The UF/DF step yield was 105% recAP mass yield and 85% recovery in activity. The HCP concentration was 120 ppm, which was higher than the target of 100 ppm. The eluate was stored at 2-8° C.

TABLE 6

Analytical results of the Demo run 5 UF/DF.

| ID Assay Method | Vol (L) | recAP conc. (g/L) $UV_{280}$ | Total recAP mass (g) $UV_{280}$ | IsoDimer A (%) RP-HPLC | Specific Activity (U/mg) Activity RP-HPLC | Total recAP Purity (%) SEC-HPLC | HCP (ng/mL) ELISA | HCP (ppm) ELISA RPHPLC |
|---|---|---|---|---|---|---|---|---|
| 3X Diluted HIC Eluate | 13.3 | 0.43 | 5.7 | 89.3 | 691 | 100 | | |
| UFDF retentate | 0.5 | 13.0 | 6.0 | 90.1 | 562 | 100 | 1,560 | 120 |
| recAP Yield (% recovered) | | | | | 105 | | | |
| Activity Yield (% recovered) | | | | | 85 | | | |

Viral Filtration & Bulk Fill

A 0.01 m2 Planova 15N hollow fiber viral filter (Asahi) was used for the viral filtration step. The cartridge was drained of storage buffer and equilibrated with formulation buffer using a peristaltic pump. The flow rate was adjusted to 5 mL/min to achieve 15 psi pressure across the membrane. The UF/DF retentate was removed from cold storage to equilibrate to room temperature. It was noted that 5-10 small white particles had formed in the retentate overnight. The retentate was pumped at 5 mL/min through the filter and was collected into a sterile PETG bottle. Filtration was completed in 180 minutes, and the pressure was maintained at 15 psi through the process. Ten mL of formulation buffer was pumped through the cartridge, collected, and added to the product to maximize recovery. The concentration was adjusted to 9.9 g/L with the addition of 96 mL of formulation buffer. The final volume of viral filtrate was 490 mL, yielding 4.8 g of product. Samples were taken for analysis by UV280 (titer), RP-HPLC (% isodimer A), SEC-HPLC (purity) and ELISA (activity and HCP). The step yield for the VF was 95% recAP mass yield and 94% recovery in activity as compared to the UF/DF retentate.

The final step in the process was filtration of the VF product by 0.2.M PES bottle top filter. The final BDS was clear and particle-free immediately after the filtration. Analysis of the BDS (Table 7) showed 97% recAP mass yield and 98% recovery in activity as compared to the viral filtrate. The HCP concentration was unchanged at 123 ppm, which was higher than the target of 100 ppm. The BDS was stored at 2-8° C.

TABLE 7

Analytical results of VF and formulation.

| ID Assay method | Vol (L) | recAP conc. (g/L) $UV_{280}$ | Total recAP mass (g) $UV_{280}$ | IsoDimer A (%) RP-HPLC | Specific Activity (U/mg) Activity RP-HPLC | Total recAP Purity (%) SEC-HPLC | HCP (ng/mL) ELISA | HCP (ppm) ELISA RPHPLC | recAP Yield (%) $UV_{280}$ | Activity Yield (%) ELISA |
|---|---|---|---|---|---|---|---|---|---|---|
| UFDF retentate | 0.40 | 13.0 | 6.0 | 90.1 | 562 | 100.0 | 1,560 | 120 | | |
| Viral filtrate | 0.49 | 10.1 | 4.9 | 90.1 | 554 | 100.0 | 1,244 | 123 | 95 | 94 |
| BDS | 0.49 | 9.9 | 4.8 | 90.0 | 559 | 100.0 | 1,221 | 123 | 97 | 98 |

Summary of Demo Run 5

A summary of the analysis of the Demo Run 5 intermediate process steps and final BDS are presented in Table 8.

TABLE 8 recAP and activity yields for each step as well as the cumulative process yields

| ID | Vol (l) | Total Protein Conc (g/L) | Total Protein (g) | recAP conc. (g/L) | Total recAP mass (g) | Iso-Dimer A (%) | Activity (U/mL) | Total Activity (U) | Specific Activity (U/mg) | HCP (ppm) | Total recAP Purity (%) | DNA (ug/mg) | recAP Yield (%) | Activity Yield (%) |
|---|---|---|---|---|---|---|---|---|---|---|---|---|---|---|
| Assay Method | | UV A200 | UV A200 | RP-HPLC | RP-HPLC | RP-HPLC | | | Activity/ RP-HPLC | ELISA/ RPHPLC | SEC-HPLC | qPCR | | |
| Harvest B01 + B03 | 19.4 | | NA | 0.7 | 13.0 | 81.3 | 368 | 7,139,200 | 518 | 1,042,215 | 3.8 | | | |
| Capto Adhere Eluate | 8.8 | | NA | 3.8 | 12.5 | 82.3 | 1003 | 7,582,000 | 603 | 467,457 | 35.5 | | 91 | 106 |
| Poros Eluate | 4.5 | | NA | 1.7 | 7.0 | 83.3 | 982 | 4,517,200 | 595 | 166,419 | 87.2 | | 91 | 60 |
| Mimetic Blue Eluate | 2.4 | 2.8 | 6.9 | | | 90.2 | 1,776 | 4,333,440 | 630 | 3,191 | 99.6 | | 91 | 96 |
| 3X Diluted HIC Eluate | 13.3 | 0.4 | 5.7 | | | 89.3 | 297 | 3,950,100 | 691 | N.D. | 100.0 | 8.0 | 93 | 91 |
| UF/DF Retentate | 0.40 | 13.0 | 6.0 | | | 90.1 | 7,332 | 3,368,120 | 562 | 120 | 100.0 | 0.3 | 105 | 85 |
| Viral Filtrate | 0.40 | 10.1 | 4.9 | | | 90.1 | 5,500 | 2,744,000 | 554 | 123 | 100.0 | | 95 | 94 |
| BDS | 0.40 | 9.9 | 4.8 | | | 90.0 | 5,500 | 2,687,580 | 559 | 123 | 100.0 | 0.3 | 97 | 98 |

The Demo run 5 scale-up overall cumulative process mass yield was 40% and the activity yield was 43% (Table 9). This yield is slightly lower than the expected yield of 45-50%. Concentration, activity, purity, and residual DNA specifications were met. The HCP concentration in the BDS was 123 ppm, which was higher than the 100 ppm target.

TABLE 9

Product specifications and results for Demo Run 5. All parameters that were tested met specifications except for HCP.

| Test | Method | Specification | Demo run 5 Results |
|---|---|---|---|
| Concentration | A280 | 9.0-11.0 mg/mL | 9.9 mg/mL |
| Specific Activity | Activity Assay | 500-600 U/mg | 559 U/mg |
| Purity | SEC-HPLC | ≥98% Main Peak | 100% |
| Residual Host Cell Protein | | ≤100 ppm | 123 ppm |
| Residual DNA | | ≤35 pg/mg | 0.3 pg/mg |
| Bioburden | | ≤1 cfu/mL | Not determined |
| Endotoxin | | ≤0.5 EU/mg of protein | Not determined | previous demonstration runs. Once the downstream purification process was revised, a small scale confirmation run was performed to confirm the final process conditions (1). The results of the demonstration run presented in this report utilized clarified cell culture harvest (200 L PD production) that was representative of the final upstream process (5). For this demonstration run, the upstream process development team provided approximately 70-liters of clarified cell culture harvest with a reverse phase (RP)-titer of approximately 0.6 g/L recAP. A portion of that harvest material, approximately 24-liters, was utilized for the demonstration run 6.

Approximately 14 grams of product was purified by four chromatography steps using the listed column sizes, column loadings, flow rates, residence times, and modes of elution (Table 10). Once the product was purified by the four chromatography steps, ultrafiltration/diafiltration (UF/DF) was performed to concentrate the product as well as remove ammonium sulfate present within the Butyl 650M process intermediate. The UF/DF retentate was then filtered through a Planova 15N viral filter. Finally, the product was 0.2 micron PES filtered into an appropriate container to achieve the bulk drug substance. It should be noted that this demonstration run incorporated the use of the measured recAP extinction coefficient of 1.01 mL/mg*cm for all concentration calculations relying on UV280.

TABLE 10

Summary of Demonstration Run 6 Column Chromatography Conditions
Demonstration Run 6 Chromatography Conditions

| Resin | Process Stop | Colision Size | Load Material | Load Preparation | Load Residence Time (min) | Loading (g recAP/L resin) | Flow Rate (cm/hr) | Elution Flow Direction | Mode of Elution |
|---|---|---|---|---|---|---|---|---|---|
| Capto Adhere | Capture | 10.0 cm ID × 23.7 cm BH column = 1.85 L | 200L PD Production | None | 5.7 | 7.5 | 250 except 150 during elution and 400 post-elution | Up | Bind & Elute |
| Poros 50 HQ | Purification 1 | 10.0 cm ID × 19.5 cm BH column = 1.53 L | Capto Eluate | (1) Inactivated with 10% with Triton X-100 (2) Diluted 12X (1 + 11) with WFI | 5.3 | 9.0 | 400 except 100 during loading and 250 for elution | Down | Bind & Elute |
| Mimetic Blue AP | Purification 2 | 14.0 cm ID × 17.0 cm BH column = 2.62 L | Poros Eluate | Diluted 2X (1 + 1) with WFI | 4.1 | 3.3 | 100 except 50 during ethanol storage | Down | Bind & Elute |
| Butyl 650M | Polishing | 10.0 cm ID × 18.8 cm BH column = 1.48 L | Mimetic Blue Eluate | Adjusted to 1.0M AmSO$_4$ | 2.8 | 6.5 | 400 except 250 during elution | Down | Bind & Elute |

Example 5

Demonstration Run Results & Discussion
Process Narrative

The parameters for the entire process were initially developed during a series of small scale purifications using varying upstream cell culture harvests. The process parameters for the Capto Adhere and Mimetic Blue chromatography steps were further refined to increase the level of host cell protein clearance following the discovery of particulates, identified as a cathepsin-like host cell protein (more specifically, as confirmed with mass-spectrometry, as the hamster homologue of Cathepsin A), in lots of BDS from the Capto Adhere Capture Step The Capto Adhere column step was used to capture the recAP product within the clarified harvest and concentrate the feed stream. Conditioning of the harvest load material was not necessary for the Capto Adhere resin as this resin can tolerate feed stream with high conductivity. The load material was equilibrated to ambient temperature and loaded onto the 1.86 L packed Capto Adhere column and purified using the conditions listed in Table 11. The maximum amount of product loaded was 14.0 g thus requiring only one cycle at 8 g recAP/L resin loading for the packed Capto Adhere column. The product elution occurred with an initial watch UV command followed by collection for 2.0 column volumes (CV). Following elution, the intermediate was 0.2 micron filtered into a 100 L BPC (Hyclone) to accommodate the viral inactivation and 12-fold dilution to follow. Once collected, the Capto Adhere intermediate was immediately moved to the viral inactivation and dilution step.

TABLE 11

Capto Adhere Capture Chromatography Run Conditions
Capto Adhere 10.0 cmID × 23.7 cmBH = 1.86 L

| Block | Buffer Condition | # CV | Flow Rate (cm/hr) | Flow Direction | Other |
|---|---|---|---|---|---|
| Sanitization | 0.5M NaOH | 3.0 | ≤250 | Down | 60 min hold |
| Condition | 2M NaCl | 3.0 | ≤250 | Down | |
| Equilibration | 20 mM Tris, 0.1M NaCl, 2 mM MgCl$_2$, 50 µM ZnCl$_2$, pH 8.0 | 3.0 | ≤250 | Down | |
| Load | Clarified Harvest | NA | ≤250 | Down | |
| Wash 1 | 20 mM Tris, 0.25M NaCl, 2 mM MgCl$_2$, 50 µM ZnCl$_2$, pH 8.0 | 7.5 | ≤250 | Down | |
| Wash 2 | 20 mM Tris, 0.1M NaCl, 2 mM MgCl$_2$, 50 µM ZnCl$_2$, pH 8.0 | 1.5 | ≤250 | Down | |
| Wash 3 | 20 mM Tris, 0.1M NaCl, 0.2M L-arginine HCl, 5% glycerol, 2 mM MgCl$_2$, 50 µM ZnCl$_2$, pH 8.0 | 5.0 | ≤250 | Down | |
| Wash 4 | 20 mM Tris, 0.1M NaCl, 2 mM MgCl$_2$, 50 µM ZnCl$_2$, pH 8.0 | 3.0 | ≤250 | Down | |
| Step Elution | 20 mM Tris, 0.1M NaCl, 0.55M L-arginine 2 mM MgCl$_2$, 50 µM ZnCl$_2$, pH 8.0 | 4.0 or until end of eluate collection | ≥150 | Up | Start collection at UV$_{280}$ ≥1.75 AU/cm; Stop collection after 2.0 CV |
| Strip 1 | 0.1M acetic acid, 2M NaCl | 3.0 | ≤400 | Up | |
| Strip 2 | WFI | 3.0 | ≤400 | Up | |
| Sanitization | 0.5M NaOH | 3.0 | ≤400 | Up | 60 min hold |
| Rinse | WFI | 3.0 | ≤400 | Up | |
| Store | 20% Ethanol | 3.0 | ≤400 | Up | |

The actual loading onto the Capto Adhere column was 7.5 g recAP/L resin. A high salt wash (250 mM NaCl) was employed to eliminate impurities (i.e. DNA, HCP) bound ionically to the mixed mode resin. Following the high salt wash, a 1.5 CV wash with equilibration buffer was completed to prevent product loss due to potential mixing of the high salt wash buffer and intermediate wash with salt, L-arginine, and glycerol. The intermediate wash (0.1M NaCl, 0.2M L-arg, 5% glycerol) was incorporated into the refined downstream process to increase removal of host cell protein, specifically cathepsin-like protein (catA), being carried throughout the baseline downstream process. To prevent mixing of the intermediate wash and elution buffers, a 3.0 CV equilibration wash was included in the process. The elution of the product was achieved in upflow using a combination of L-arginine and sodium chloride as was established during preliminary development. The maximum eluate volume was 2.0 CV once the UV watch condition occurred. The feed stream reduced from 23.7-liters to approximately 3.7-liters after the Capto Adhere column step.

The results suggested that the incorporation of the intermediate wash (Wash#3) possessing a combination of modulators was beneficial for enhancing the level of HCP clearance for the capture step within the downstream process. Overall, the analytical results for the Capto Adhere process intermediate were highly comparable to the previous demonstration runs but with significantly increased HCP clearance.

Viral Inactivation & Poros 50 HQ Purification

A viral inactivation step was included to effectively inactivate potential enveloped viruses. The Triton X-100 detergent utilized for inactivation must be removed from the product prior to product fill and administration to humans and animals, which can be achieved by the process steps that follow inactivation. The purification step to follow viral inactivation included anion exchange chromatography using Poros HQ resin. This process step would help remove residual Triton X-100 as well as additional impurities (i.e. DNA, HCP) from the product. Approximately 13.8 g of product was recovered after the capture step with a conductivity of 38.8 mS/cm. The maximum loading for the Poros HQ resin is not to exceed 10 g recAP/L resin therefore only one cycle was required for a 1.53-liter Poros HQ column.

The Capto Adhere chromatography and viral inactivation were completed on the same day. For the viral inactivation, a 1:9 v/v of a 10% Triton X-100 stock solution was added to the Capto Adhere eluate to make a 1% Triton X-100 final concentration. The product was thoroughly mixed and then kept static for 1 hour at ambient temperature to allow for complete viral inactivation. Prior to loading onto the packed Poros HQ column, the viral inactivated Capto eluate was diluted 12× (1+11) with WFI to reduce the conductivity to 4.4 mS/cm which is within the specification of ≤4.5 mS/cm. The viral inactivated and diluted Capto Ahdere eluate was loaded onto a 1.53 L Poros HQ column at a loading of approximately 9 g recAP/L resin. The product was purified using the established conditions listed in Table 12. A low salt wash (50 mM NaCl) was performed to remove impurities after the material was loaded. The product elution was achieved using high salt (130 mM NaCl) for a maximum eluate collection of 3.0 CV once the UV watch condition occurred. The eluate was 0.2 micron filtered into a 10 L BPC (Hyclone) prior to storage at 2-8° C.

TABLE 12

Poros HQ Chromatography Run Conditions
Poros 50 HQ 10.0 cmID × 19.5 cmBH = 1.53 L

| Block | Buffer Condition | # CV | Flow Rate (cm/hr) | Flow Direction | Other |
|---|---|---|---|---|---|
| Sanitization | 0.5M NaOH | 3.0 | ≤400 | Down | 60 min hold |
| Condition | 2M NaCl | 3.0 | ≤400 | Down | |
| Equilbration | 20 mM Tris, 2 mM MgCl$_2$, 50 μM ZnCl$_2$, pH 8.0 | 3.0 | ≤400 | Down | |
| Load | Viral Inactivated & Diluted Capto Adhere Eluate | NA | ≤300 | Down | |
| Post-Load Wash | 20 mM Tris, 2 mM MgCl2, 50 μM ZnCl$_2$, 50 mM NaCl pH 8.0 | 5.0 | ≤400 | Down | |
| Step Elution | 20 mM Tris, 2 mM MgCl2, 50 μM ZnCl$_2$, 130 mM NaCl pH 8.0 | 4.0 or until end of eluate collection | ≥250 | Down | Start collection at UV$_{280}$ ≥0.5 AU/cm; End collection after 3.0 CV |
| Strip | 2M NaCl | 3 | ≤400 | Down | |
| Sanitization | 0.5M NaOH | 3 | ≤400 | Down | 60 min hold |
| Store | 20% Ethanol | 3 | ≤400 | Down | |

The chromatography profile for the Poros HQ step was consistent with previous results, giving a slight UV absorbance during loading due to the presence of Triton X-100 in the load material. The chromatogram revealed a sharp eluate peak with a maximum absorbance of 3.2 AU. There was an intense peak during the 2M NaCl strip, which was previously identified to be non-product related impurities.

The Poros HQ eluate was analyzed by the RP-HPLC titer method, endpoint activity assay, HCP ELISA, and SEC-HPLC and compared to the Capto Adhere intermediate. The recAP and activity recoveries for the purification step were similar to demonstration run 5 as well as the bench scale confirmation run at 63% and 68% respectively (1, 2). There was over a 3-fold reduction in residual HCP compared to the load material, suggesting the first two process steps were indeed capable of significant HCP reduction although the additional purification steps were necessary to meet the target HCP specification of ≤100 ppm. The % isodimer A increased within the intermediate, maintaining high recAP purity at 98.6% by SEC-HPLC.

Mimetic Blue Purification

Upon completion of the Poros 50 HQ purification, the subsequent purification step included affinity chromatography using the Mimetic Blue AP resin. There was approximately 9 g of product to be purified by the Mimetic Blue column step. With a 2.6 L packed column, only one cycle was required at approximately 3.3 g recAP/L loading. The Poros HQ eluate was allowed to warm to ambient temperature followed by a 2× (1+1) dilution with WFI to reduce the conductivity prior to loading. Once the aliquot was diluted, it was loaded onto the packed 2.6 L Mimetic Blue column and purified using the revised conditions listed in Table 13. The process conditions were slightly modified from the previously established conditions with the inclusion of an intermediate wash with L-arginine to remove residual HCP followed by a wash with equilibration buffer to prevent product loss due to buffer mixing. In addition to the intermediate wash, the elution conditions were modified from the previous demonstration runs with the use of solely sodium phosphate instead of a combination of sodium phosphate and salt. The refinement studies for the Mimetic Blue column step demonstrated a dramatic decrease in residual HCP for the process intermediate with the exclusion of salt in the elution buffer therefore it was eliminated from the process (1). During the elution, a pre-defined UV gate of ≥0.125 AU/cm to ≤0.25 AU/cm was utilized for collection of the product. The product was 0.2 micron PES filtered into a sterile 5 L BPC (Hyclone) prior to storage at 2-8° C.

TABLE 13

Mimetic Blue Purification Chromatography Run Conditions
Mimetic Blue AP 14.0 cmID × 17.0 cmBH = 2.6 L

| Block | Buffer Condition | # CV | Flow Rate (cm/hr) | Flow Direction | Other |
|---|---|---|---|---|---|
| Sanitization | 0.5M NaOH | 3 | ≤100 | Down | 60 min hold |
| Equilibration | 20 mM Tris, 2 mM MgCl$_2$, 50 μM ZnCl$_2$, pH 8.0 | 3 | ≤100 | Down | |
| Load | 2X (1 + 1) Diluted Poros Eluate Load | NA | ≤100 | Down | |
| Wash # 1 | 20 mM Tris, 2 mM MgCl$_2$, 50 μM ZnCl$_2$, pH 8.0 | 1.5 | ≤100 | Down | |
| Wash # 2 | 20 mM Tris, 40 mM L-Arg HCl, 2 mM MgCl$_2$, 50 μM ZnCl$_2$, pH 8.0 | 3 | ≤100 | Down | |
| Wash # 3 | 20 mM Tris, 2 mM MgCl$_2$, 50 μM ZnCl$_2$, pH 8.0 | 1.5 | ≤100 | Down | |
| Step Elution | 20 mM Tris, 2 mM MgCl$_2$, 50 μM ZnCl$_2$, 25 mM sodium phosphate, pH 8.0 | 4.0 or until end of eluate collection | ≤100 | Down | Start collection at UV$_{280}$ ≥0.125 AU/cm; Stop collection at UV$_{280}$ ≤0.25 AU/cm |
| Strip | 0.1M sodium phosphate, 0.5M NaCl, pH 7.0 | 3 | ≤100 | Down | |

TABLE 13-continued

Mimetic Blue Purification Chromatography Run Conditions
Mimetic Blue AP 14.0 cmID × 17.0 cmBH = 2.6 L

| Block | Buffer Condition | # CV | Flow Rate (cm/hr) | Flow Direction | Other |
|---|---|---|---|---|---|
| Sanitization | 0.5M NaOH | 3 | ≤100 | Down | 60 min hold |
| Store | 20% Ethanol | 3 | ≤50 | Down | |

The chromatography elution profile was very similar to previous demonstration runs. The eluate was analyzed by the analytical group for RP-titer, qPCR for residual DNA, enzymatic activity, residual HCP, and purity by SEC-HPLC. The results of the Mimetic Blue purification step revealed recoveries of 92% for recAP and 91% for activity. The purity by SEC-HPLC increased to approximately 100%, confirming that recAP was the main product present within the intermediate. The level of residual DNA was reduced to <0.5 pg/mg, well below the target specification of ≤35 pg/mg. Consistent with the bench scale confirmation run, the residual HCP present within the Mimetic Blue eluate decreased dramatically by approximately 2000-fold using the refined Mimetic Blue conditions, which was a large improvement over the 50-fold reduction presented in demonstration run 5 (1, 2). The residual HCP was significantly below the ≤100 ppm target specification for the drug substance. The results from the Mimetic Blue purification established that the Mimetic Blue column step was providing the greatest HCP clearance compared to the former column steps.

Butyl 650M Polishing

The final chromatography step within the process included hydrophobic interaction chromatography (HIC) using the Butyl 650M resin. Prior to the HIC chromatography, the Mimetic Blue eluate was allowed to warm to ambient temperature prior to ammonium sulfate addition. The UV280 of the Mimetic Blue eluate was used to calculate the minimum number of Butyl 650M cycles not to exceed 10 g recAP/L resin. For a packed 1.48 L Butyl 650M column, only one cycle was deemed necessary for a maximum loading of 5.5 g recAP/L resin. Just prior to column loading, the Mimetic Blue eluate was diluted with 2.1 M $AmSO_4$ pH 8.0 to a final concentration of 1.0 M $AmSO_4$. The column loading was completed within 1 hour of ammonium sulfate addition to reduce potential precipitate formation. The product was then purified using the established conditions listed in Table 14. The product was eluted with 0.6 M $AmSO_4$ using a pre-defined UV gate of ≥0.25 AU/cm to ≤0.25 AU/cm. Once eluted from the column, the eluate was immediately diluted 3× (1+2) with WFI and 0.2 micron PES filtered into a sterile 20 L BPC (Hyclone) prior to storage at 2-8° C.

TABLE 14

Butyl 650M Polishing Chromatography Run Conditions
Butyl 650M 10.0 cmID × 18.8 cmBH = 1.48 L

| Block | Buffer Condition | # CV | Flow Rate (cm/hr) | Flow Direction | Other |
|---|---|---|---|---|---|
| Sanitization | 0.5M NaOH | 3.0 | ≤400 | Down | 60 min hold |
| Equilibration | 20 mM Tris, 1.0M $AmSO_4$, 2 mM $MgCl_2$, 50 μM $ZnCl_2$, pH 8.0 | 3.0 | ≤400 | Down | |
| Load | Mimetic Blue Eluate adjusted to 1.0M $AmSO_4$ | NA | ≤400 | Down | |
| Post-Load Wash | 20 mM Tris, 1.0M $AmSO_4$, 2 mM $MgCl_2$, 50 μM $ZnCl_2$, pH 8.0 | 3.0 | ≤400 | Down | |
| Elution | 20 mM Tris, 1.0M $AmSO_4$, 2 mM $MgCl_2$, 50 μM $ZnCl_2$, pH 8.0 | 5.0 or until end of flow thru collection | ≥250 | Down | Start collection at $UV_{280}$ ≥0.25 AU/cm; Stop collection at $UV_{280}$ 0.25 AU/cm |
| Strip | WFI | 2.0 | ≤400 | Down | |
| Sanitization | 0.5M NaOH | 3.0 | ≤400 | Down | 60 min hold |
| Store | 20% Ethanol | 3.0 | ≤400 | Down | |

The chromatogram for the HIC step was consistent with previous experiments, resulting in an eluate peak with a maximum absorbance of 1.6 AU. The Butyl 650M process intermediate was analyzed by UV280 for concentration, endpoint activity assay, RP-titer, qPCR for residual DNA, HCP ELISA, and SEC-HPLC for purity and compared to the Mimetic Blue intermediate. The eluate maintained high specific activity as well as recoveries at greater than 80% for recAP and activity. The purity of recAP by SEC-HPLC was maintained at 99.9%. No high molecular weight (HMW) aggregates were seen by SEC-HPLC, suggesting that the addition of ammonium sulfate does not alter product quality or cause aggregation of the product. The residual HCP concentration was below the limit of detection (≤3 ppm) for the HCP ELISA assay. Therefore, the residual HCP concentration was reduced at least 12-fold after the HIC chromatography step, suggesting that the HIC step was necessary for further clearance of HCP through the process.

Ultrafiltration/Diafiltration

The next step within the process included ultrafiltration/diafiltration to buffer exchange as well as concentrate the product. A 0.1 m2 Pellicon 2 Ultrafiltration Biomax cassette with a molecular weight cut off of 10 kDa was utilized to concentrate the product followed by diafiltration to eliminate ammonium sulfate. The membrane was first sanitized with 0.5 M NaOH for 1 hour, rinsed with WFI, and equilibrated with formulation buffer (20 mM L-Histidine, 250 mM D-sorbitol, 2 mM $MgCl_2$, 50 µM $ZnCl_2$, pH 7.0). The diluted HIC eluate was warmed to ambient temperature prior to loading onto the membrane. The product loading on the membrane was 70 g/m2. The TMP was maintained at ≤15 PSI throughout the run using a cross flow rate of 0.5 L per min for the 0.1 m2 membrane. The diluted Butyl 650M eluate was initially concentrated to 14 g/L followed by a 10× diafiltration with formulation buffer. The membrane was then flushed with approximately 31 mL of formulation buffer to reach a target concentration of 11.5 g/L by UV280. Once the target concentration was reached, the retentate was filtered using a 0.2 micron PES filter unit and immediately processed through viral filtration.

The load and UF/DF retentate (with flush) were analyzed for activity, concentration by UV280, residual DNA by qPCR, purity by SEC-HPLC and residual HCP. The purity of recAP was maintained at 100%, indicating no aggregate formation. The recovery for the UF/DF step was approximately 70%, which was lower than that for demonstration run 5 with 100% recovery (2). The same membrane utilized in demonstration run 5 processing was used for this demonstration run and its re-use could attribute to the loss of product. The residual HCP concentration within the UF/DF retentate was below the limit of quantitation of the HCP ELISA.

Viral Filtration & Bulk Fill

Prior to bulk fill, the final step within the process was viral filtration. A 0.001 m2 Planova 15N filter was equilibrated with 50 L/m2 formulation buffer (20 mM L-Histidine, 250 mM D-sorbitol, 2 mM $MgCl_2$, 50 µM $ZnCl_2$, pH 7.0). The UF/DF retentate was applied to the equilibrated viral filter at 430 L/m2 loading, maintaining a differential pressure of ≤15 psi. Once all material was applied, the filter was flushed with 10 L/m2 of formulation buffer to recover protein in the filter housing. The flush was then added to the filtrate to give a final concentration of 10.4 g/L. The target specification for the bulk drug substance was 9.0 to 11.0 mg/mL therefore the final concentration was within the specification range prior to PES filtration. For preparation of the BDS, the viral filtrate was then filtered through a 0.2 micron PES filter system into a 1 L PETG container and stored at 2-8° C.

The load, viral filtrate with flush, and bulk drug substance were analyzed for enzymatic activity, residual DNA by qPCR, RP-titer, purity by SEC-HPLC, concentration by UV280 and residual HCP by ELISA. Approximately 98% of the product was recovered after the viral filtration step. The specific activity and purity were both maintained during filtration. The residual HCP was well below the target specification of ≤100 ppm within the bulk drug substance. This result confirmed that the refined process was capable of greater HCP clearance than the baseline process which teetered around 100 ppm throughout the previous demonstration runs.

Summary of Demonstration Run Results

Upon completion of the demonstration run, the analytical results for each process intermediate were tabulated and presented in FIG. 16. The most important factor for this demonstration run was the dramatic clearance of HCP to <0.5 ppm, well below the target specification of <100 ppm, using the refined conditions that had been further established for the Capto Adhere and Mimetic Blue column steps (1).

Stability Testing

Stability tests were performed with the formulations obtained in Example 3. The results of formulations in histidine buffer and in citrate buffer under the conditions indicated are summarized in FIG. 17.

The invention claimed is:
1. A method for isolating an alkaline phosphatase (AP) comprising:
(a) providing a solid phase comprising a ligand of formula (I):

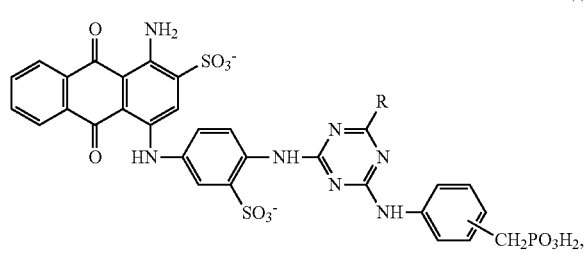

wherein R is a spacer molecule which links the ligand to the solid phase,
(b) contacting said ligand with a composition comprising an AP that comprises an amino acid sequence 100% identical to SEQ ID NO: 1 and a host cell protein (HCP);
(c) performing two or more wash steps, wherein at least one wash step is performed using a wash buffer comprising between 20-100 mM arginine (Arg), between 0.5-2 M Urea, or between 5-15% ethylene glycol, or any combination thereof; and
(d) eluting said AP from the ligand with an elution buffer; wherein said eluate comprises less than 100 ppm HCP.
2. A method according to claim 1, wherein the wash buffer comprises less than 1 mM NaCl.
3. A method according to claim 1, wherein the elution buffer comprises less than 1 mM NaCl.
4. A method according to claim 1, wherein the washing buffer comprises about 40 mM Arg.
5. A method according to claim 1, the method further comprising:
(i) providing a second solid phase comprising a second ligand of formula (II):

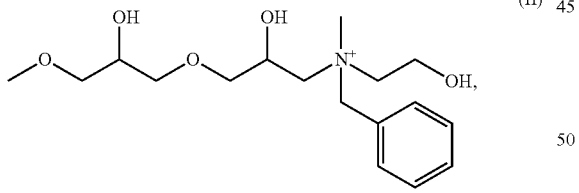

(ii) contacting said second ligand with a composition comprising said AP and a HCP, and
(iii) performing two or more wash steps, wherein at least one wash step is performed using a second washing buffer having a pH between 7.5-8.5 and comprising between 0.05-0.2 M NaCl and between 0.1-0.5 M L-Arg.
6. A method according to claim 5, wherein said second washing buffer comprises between 1-20% glycerol.
7. A method according to claim 5, wherein (i)-(ii) precedes (a)-(d).
8. A method according to claim 1, further comprising at least one further purification step selected from the group consisting of anion exchange chromatography, ultrafiltration/diafiltration, viral filtration, and hydrophobic interaction chromatography, and any combination thereof.
9. A method for producing a composition comprising an isolated alkaline phosphatase (AP) comprising an amino acid sequence that is 100% identical to SEQ ID NO: 1, the method comprising
dissolving or diluting said AP in a buffer, which results in a composition having a pH of between 6.5 and 7.5 and comprising between 200-300 mM sorbitol, and/or between 10-40% glycerol, and/or between 5-40 mM histidine, and/or between 10-40 mM citrate, or any combination thereof;
wherein there is no visible particle formation in said composition, using a stability test at 2-8° C. for 2 months.
10. A method according to claim 9, wherein the composition comprises less than 100 ppm host cell protein (HCP).
11. A composition comprising an isolated alkaline phosphatase obtained from a cell-based expression system, wherein the alkaline phosphatase comprises an amino acid sequence that is 100% identical to SEQ ID NO: 1, wherein the composition comprises less than 100 ppm of a host cell protein (HCP) and wherein the composition does not show visible particle formation during stability testing at 2-8° C. for 2 months.
12. A composition according to claim 11, wherein the composition has a pH of between 6.5-7.5, and comprises between 10-40 mM citrate or between 5-40 mM histidine.
13. A composition according to claim 12, wherein the composition comprises between 200-300 mM sorbitol and/or between 10-40% glycerol.
14. A method according to claim 1, wherein the HCP is a cathepsin-like protein and/or wherein said alkaline phosphatase is obtained from a cell-based expression system.
15. A method for treating a disease or condition that can be improved by the administration of alkaline phosphatase, the method comprising administering to an individual in need thereof a composition according to claim 11.
16. A method according to claim 10, wherein the composition comprises AP obtained by a method comprising:
(a) providing a solid phase comprising a ligand of formula (I):

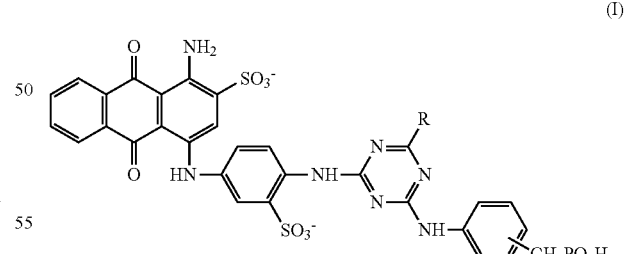

wherein R is a spacer molecule which links the ligand to the solid phase,
(b) contacting said ligand with a composition comprising an AP that comprises an amino acid sequence 100% identical to SEQ ID NO: 1 and a host cell protein (HCP);
(c) performing two or more wash steps, wherein at least one wash step is performed using a wash buffer comprising between 20-100 mM arginine (Arg), between 0.5-2 M Urea, or between 5-15% ethylene glycol, or any combination thereof; and (d) eluting said AP from the ligand with an elution buffer; wherein said eluate comprises less than 100 ppm HCP.

17. A composition according to claim 11, wherein the HCP is a cathepsin-like protein.

18. The composition according to claim 11, wherein the alkaline phosphatase is recombinant.

19. A composition according to claim 12, wherein the pH is about 7.

* * * * *